US012678111B2

(12) United States Patent
Miller et al.

(10) Patent No.: US 12,678,111 B2
(45) Date of Patent: Jul. 14, 2026

(54) METHODS, SYSTEMS, AND COMPUTER-READABLE STORAGE MEDIA FOR ENHANCED PHASE-CONTRAST X-RAY IMAGING

(71) Applicant: Battelle Memorial Institute, Richland, WA (US)

(72) Inventors: Erin A. Miller, Richland, WA (US); Dustin M. Kasparek, Richland, WA (US); Luke W. Campbell, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 253 days.

(21) Appl. No.: 18/655,160

(22) Filed: May 3, 2024

(65) Prior Publication Data

US 2024/0298984 A1 Sep. 12, 2024

Related U.S. Application Data

(63) Continuation-in-part of application No. 18/519,861, filed on Nov. 27, 2023, now abandoned, which is a
(Continued)

(51) Int. Cl.
*A61B 6/42* (2024.01)
*A61B 6/00* (2006.01)
(Continued)

(52) U.S. Cl.
CPC .......... *A61B 6/4291* (2013.01); *A61B 6/4035* (2013.01); *A61B 6/405* (2013.01); *A61B 6/466* (2013.01); *A61B 6/484* (2013.01)

(58) Field of Classification Search
CPC .... A61B 6/00; A61B 6/40; A61B 6/42; A61B 6/46; A61B 6/4035; A61B 6/405; A61B 6/4291; A61B 6/466; A61B 6/484
See application file for complete search history.

(56) References Cited

U.S. PATENT DOCUMENTS 5,812,629 A 9/1998 Clauser
9,357,975 B2 6/2016 Baturin et al.
(Continued)

FOREIGN PATENT DOCUMENTS

WO WO 2011/011014 1/2011
WO WO 2012/029039 3/2012

OTHER PUBLICATIONS

Pfeiffer et al., "Phase retrieval and differential phase-contrast imaging with low-brilliance X-ray sources," *Nature Physics*, 2(4): 258-261 (Mar. 2006).
(Continued)

*Primary Examiner* — Jurie Yun
(74) *Attorney, Agent, or Firm* — Klarquist Sparkman, LLP

(57) ABSTRACT

A system includes an x-ray source configured to emit an x-ray beam along a beam path and through an object arranged for inspection in a field of view of the x-ray source; and an object grating, an analyzer grating, a detector grating, and a detector arranged with respect to each other in the field of view, wherein the object grating includes object grating elements arranged in a first pattern, the detector grating includes detector grating elements arranged in a second pattern that is separable from the first pattern, and the analyzer grating includes analyzer grating elements that are arranged to correspond to a combination of the first pattern and second pattern, wherein the analyzer grating, and/or the object grating and detector grating, are configured to move relative to each other to different phase positions, and wherein the detector is configured to collect indirect moiré image data of the object at the different phase positions.

29 Claims, 30 Drawing Sheets

Related U.S. Application Data continuation of application No. 17/442,340, filed as application No. PCT/US2020/023884 on Mar. 20, 2020, now Pat. No. 11,826,187, which is a continuation of application No. 16/363,989, filed on Mar. 25, 2019, now Pat. No. 11,006,912.

(51) Int. Cl.
| | |
|---|---|
| *A61B 6/40* | (2024.01) |
| *A61B 6/46* | (2024.01) |

(56) References Cited

U.S. PATENT DOCUMENTS

| | | | |
|---|---|---|---|
| 9,761,021 | B2 | 9/2017 | Koehler et al. |
| 10,478,142 | B2 * | 11/2019 | Ning ..................... A61B 6/032 |
| 11,006,912 | B2 | 5/2021 | Miller et al. |
| 11,639,903 | B2 | 5/2023 | Miller et al. |
| 2010/0091947 | A1 | 4/2010 | Niu et al. |
| 2012/0163554 | A1 | 6/2012 | Tada |
| 2012/0201349 | A1 | 8/2012 | Kaneko et al. |
| 2013/0108015 | A1 | 5/2013 | Kottler et al. |
| 2014/0226782 | A1 | 8/2014 | Stutman et al. |
| 2020/0305812 | A1 | 10/2020 | Miller et al. |
| 2021/0349040 | A1 | 11/2021 | Miller et al. |
| 2022/0160315 | A1 | 5/2022 | Miller et al. |

OTHER PUBLICATIONS

Pfeiffer et al., "Hard-X-ray dark-field imaging using a grating interferometer," *Nature Materials*, 7(2): 134-137 (Jan. 2008).

Fitzgerald, "Phase-sensitive x-ray imaging," *Physics Today*, 53(7): 23-26 (Jul. 2000).

Momose et al., "Demonstration of X-ray Talbot interferometry," *Japanese Journal of Applied Physics*, 42(7B): L866-L868 (Jul. 2003).

Olivo et al., "A coded-aperture technique allowing x-ray phase contrast imaging with conventional sources," *Applied Physics Letters*, 91(7), 3 pages (Aug. 2007).

Wen et al, "Spatial harmonic imaging of x-ray scattering—initial results," *IEEE Transactions on Medical Imaging*, 27(8): 997-1002 (Aug. 2008).

Wells et al., "A review of X-ray explosives detection techniques for checked baggage," *Applied Radiation and Isotopes*, 70(8): 1729-1746 (Aug. 2012).

Singh et al., "Explosives detection systems (EDS) for aviation security," *Signal Processing*, 83(1): 31-55 (Jan. 2003).

Alvarez et al., "Energy-selective reconstructions in x-ray computerized tomography," *Physics in Medicine & Biology*, 21(5): 733-744 (Feb. 1976).

Roder, "Explosives detection by dual-energy computed tomography (CT)," *Proc. SPIE 0182, Imaging Applications for Automated Industrial Inspection and Assembly*, pp. 171-178 (Oct. 1979).

Azevedo et al., "System-independent characterization of materials using dual-energy computed tomography," *IEEE Transactions on Nuclear Science*, 63(1): 341-350 (Feb. 2016).

Wang et al., "Quantitative grating-based x-ray dark-field computed tomography," *Applied Physics Letters*, 95(9): 094105 (Aug. 2009).

Bech et al., "Quantitative x-ray dark-field computed tomography," *Physics in Medicine & Biology*, 55(18): 5529-5539 (Aug. 2010).

Pfeiffer et al., "Tomographic reconstruction of three-dimensional objects from hard X-ray differential phase contrast projection images," *Nuclear Instruments and Methods in Physics Research Section A: Accelerators, Spectrometers, Detectors and Associated Equipment*, 580(2): 925-928 (Oct. 2007).

Pfeiffer et al., "Hard x-ray phase tomography with low-brilliance sources," *Physical review letters*, 98(10): 108105 (Mar. 2007).

Lynch et al., "Interpretation of dark-field contrast and particle-size selectivity in grating interferometers," *Applied Optics*, 50(22): 4310-4319 (Jul. 2011).

Pfeiffer et al., "High-resolution brain tumor visualization using three-dimensional x-ray phase contrast tomography," *Physics in Medicine & Biology*, 52(23): 6923-6930 (Nov. 2007).

Arboleda et al., "Sensitivity-based optimization for the design of a grating interferometer for clinical X-ray phase contrast mammography," *Optics Express*, 25(6): 6349-6364 (Mar. 2017).

Huang et al., "Alternative method for differential phase-contrast imaging with weakly coherent hard x rays," *Physical Review A—Atomic, Molecular, and Optical Physics*, 79(1): 013815 (Jan. 2009).

Wen et al., "Fourier X-ray scattering radiography yields bone structural information," *Radiology*, 251(3): 910-918 (Jun. 2009).

Stein et al., "Selective imaging of nano-particle contrast agents by a single-shot x-ray diffraction technique," *Optics express*, 18(12): 13271-13278 (Jun. 2010).

Van der Walt et al., "scikit-image: image processing in Python," *PeerJ*, 2: e453 (Jun. 2014).

Feldkamp et al., "Practical cone-beam algorithm," *Journal of the Optical Society of America A*, 1(6): 612-619 (Jun. 1984).

Van Aarle et al., "The ASTRA Toolbox: A platform for advanced algorithm development in electron tomography," *Ultramicroscopy*, 157: 35-47 (Oct. 2015).

Van Aarle et al., "Fast and flexible X-ray tomography using the ASTRA toolbox," *Optics express*, 24(22): 25129-25147 (Oct. 2016).

Jensen et al., "Directional x-ray dark-field imaging," *Physics in Medicine & Biology*, 55(12): 3317-3323 (May 2010).

Sharma et al., "Design of acquisition schemes and setup geometry for anisotropic X-ray dark-field tomography (AXDT)," *Scientific Reports*, 7(1): 3195 (Jun. 2017).

Sharma et al., "Trochoidal X-ray Vector Radiography: Directional dark-field without grating stepping," *Applied Physics Letters*, 112(11): 111902 (Mar. 2018).

Felsner et al., "A 3-D projection model for x-ray dark-field imaging," *Scientific Reports*, 9(1): 9216 (Jun. 2019).

Graetz et al., "Review and experimental verification of x-ray dark-field signal interpretations with respect to quantitative isotropic and anisotropic dark-field computed tomography," *Physics in Medicine & Biology*, 65(23): 235017 (Nov. 2020).

Berger et al., "XCOM: Photon Cross Sections Database," *National Institute of Standards and Technology*, NBSIR 87-3597, 9 pages (Nov. 2010).

Poludniowski et al., "SpekCalc: a program to calculate photon spectra from tungsten anode x-ray tubes," *Physics in Medicine & Biology*, 54(19): N433 (Sep. 2009).

Willner et al., "Quantitative X-ray phase-contrast computed tomography at 82 keV," *Optics express*, 21(4): 4155-4166 (Feb. 2013).

Birnbacher et al., "Accurate effective atomic No. determination with polychromatic grating-based phase-contrast computed tomography," *Optics express*, 26(12): 15153-15166 (Jun. 2018).

Sarapata et al., "Quantitative imaging using high-energy X-ray phase-contrast CT with a 70 kVp polychromatic X-ray spectrum," *Optics express*, 23(1): 523-535 (Jan. 2015).

Donath et al., "Inverse geometry for grating-based x-ray phase-contrast imaging," *Journal of Applied Physics*, 106(5): 054703 (Sep. 2009).

Kasparek et al., "Gratings-based phase contrast imaging above 160 kVp," *Proc. SPIE 12531, Anomaly Detection and Imaging with X-Rays (ADIX) VIII*, p. 125310H, (May 4, 2023).

Extended EP Search Report for related EP Application No. 20778845.6, 6 pages, mailed Nov. 25, 2022.

International Search Report and Written Opinion for related International Application No. PCT/US2020/23884, 10 pages, mailed Jun. 16, 2020.

Office action for related Canadian Application No. 3133306, 4 pages, dated Jan. 17, 2024.

Yashiro et al., "Effect of beam hardening on a visibility-contrast image obtained by X-ray grating interferometry," *Optics Express*, 23(18), 10 pages (Sep. 7, 2015).

* cited by examiner

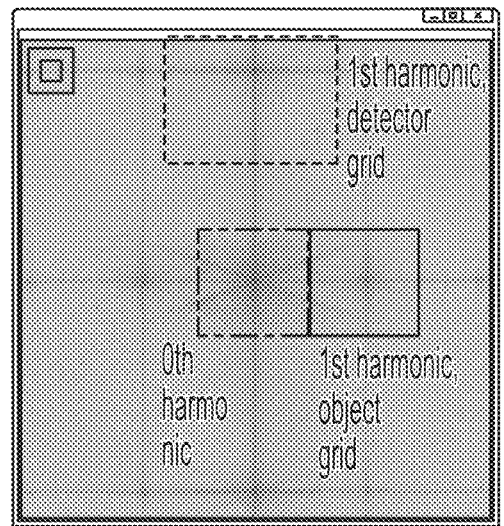
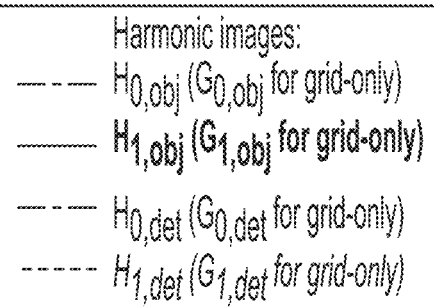
Harmonic images:
$--- \quad H_{0,obj}$ $(G_{0,obj}$ for grid-only)
$--- \quad \mathbf{H_{1,obj}}$ $(\mathbf{G_{1,obj}}$ for grid-only)
$--- \quad H_{0,det}$ $(G_{0,det}$ for grid-only)
$--- \quad H_{1,det}$ $(G_{1,det}$ for grid-only)
Corrected Scatter $(V/V_0)_{object}$ / $(V/V_0)_{detector}$
$$\text{ScatterRatio} = \frac{|iFFT(H_{1,obj})|}{|iFFT(G_{1,obj})|} \cdot \frac{|iFFT(G_{1,det})|}{|iFFT(H_{1,det})|}$$
FIG. 5
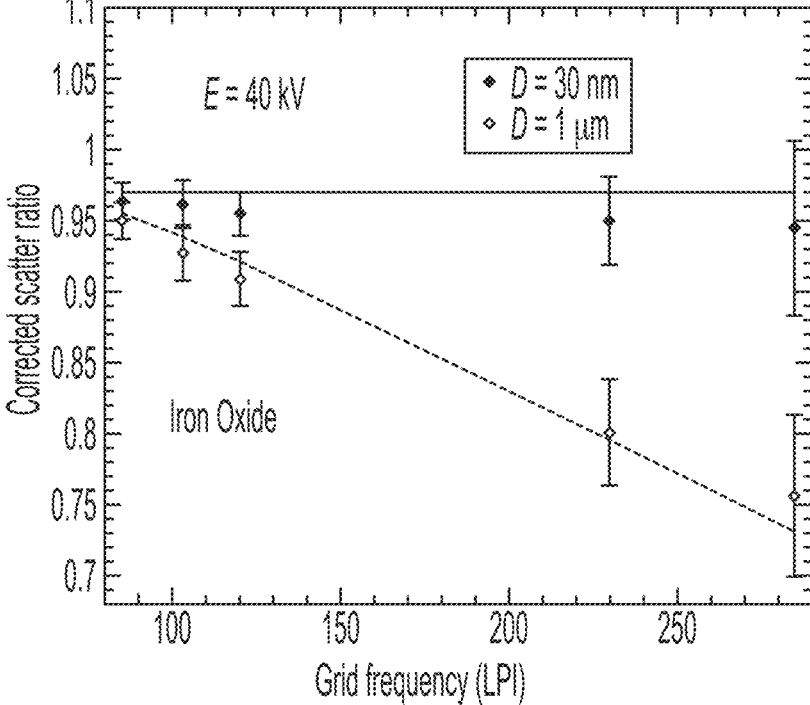
FIG. 6

FIG. 10A                  FIG. 10B

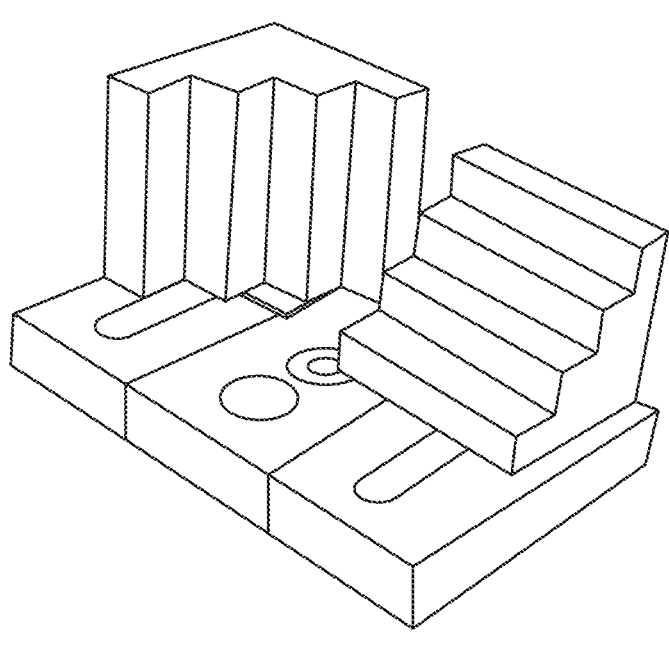
FIG. 11A
Corrected visibility reduction (V/V₀)
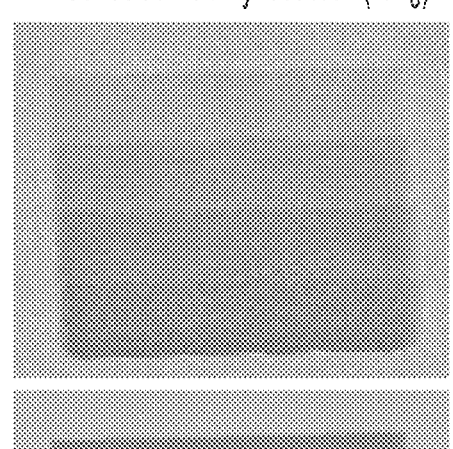
High E
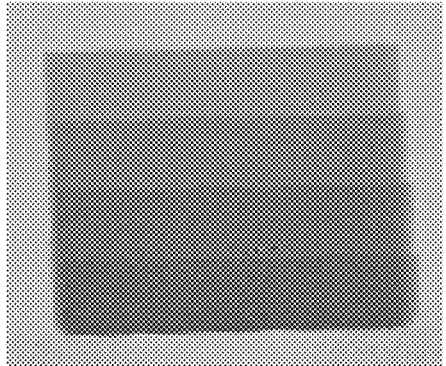
Low E
FIG. 11B

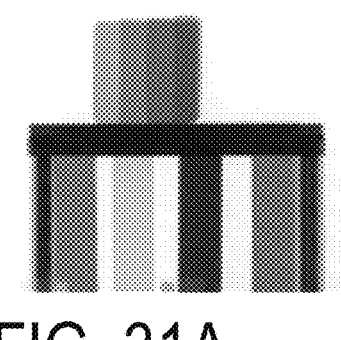
FIG. 31A
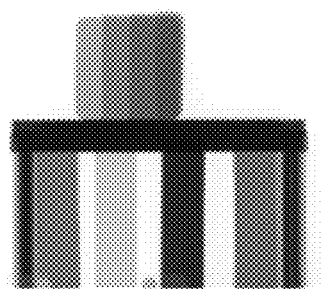
FIG. 31B
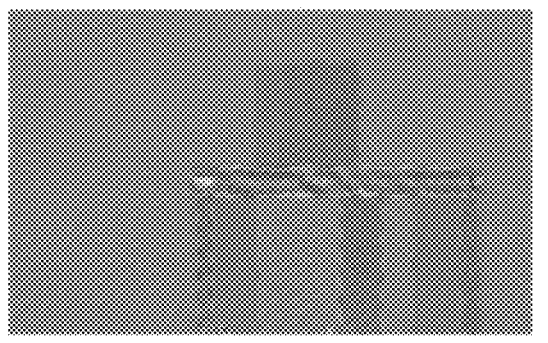
FIG. 32A
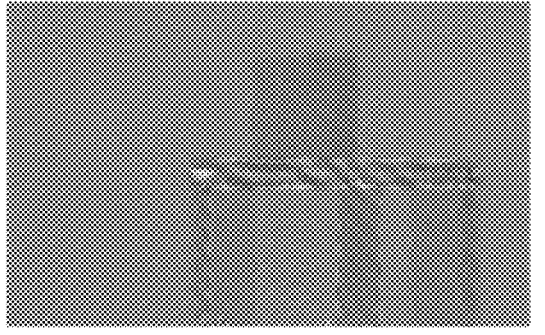
FIG. 32B
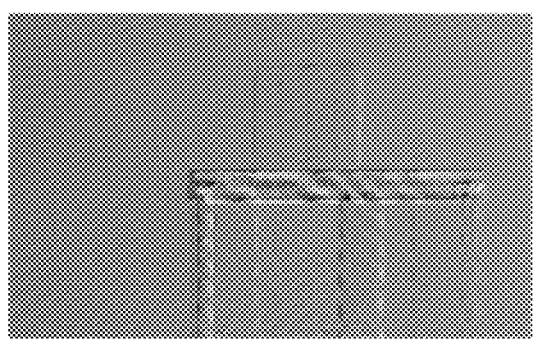
FIG. 33A
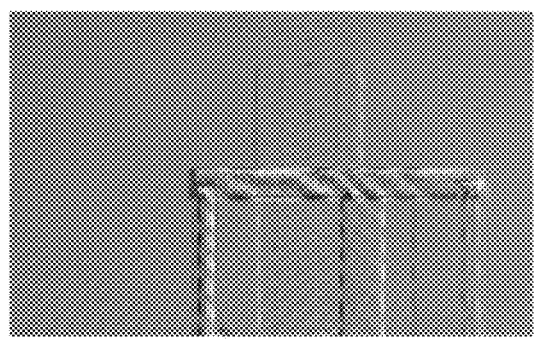
FIG. 33B

METHODS, SYSTEMS, AND COMPUTER-READABLE STORAGE MEDIA FOR ENHANCED PHASE-CONTRAST X-RAY IMAGING

CROSS REFERENCE TO RELATED APPLICATIONS

This is a continuation-in-part of U.S. patent application Ser. No. 18/519,861, filed Nov. 27, 2023, which is a continuation of U.S. patent application Ser. No. 17/442,340, filed Sep. 23, 2021, now issued as U.S. Pat. No. 11,826,187, which is a U.S. National Stage of International Application No. PCT/US2020/023884, filed Mar. 20, 2020, which was published in English under PCT Article 21(2), which is a continuation of U.S. patent application Ser. No. 16/363,989, filed Mar. 25, 2019, now issued as U.S. Pat. No. 11,006,912, all of which are incorporated herein in their entirety.

ACKNOWLEDGEMENT OF GOVERNMENT SUPPORT

This invention was made with Government support under Contract DE-AC0576RL01830 awarded by the U.S. Department of Energy. The Government has certain rights in the invention.

FIELD

The present disclosure relates to phase-contrast x-ray imaging, and more particularly to phase-contrast x-ray imaging having improved quality and material discriminating power.

BACKGROUND

X-ray based imaging is used in a variety of non-destructive examination (NDE) applications. In many of these applications, which can range from medical imaging to security screening, the primary x-ray characteristics are density and effective atomic number derived from multi-spectral x-ray attenuation measurements. The addition of phase contrast as a third imaging characteristic can improve material discrimination by detection of refractive and scattering effects in examined objects. However, unwanted spectral effects, misleading image artifacts, and the demands associated with producing images with increased material penetration required novel solutions in order to improve resultant x-ray images. Such solutions are described herein.

SUMMARY

Disclosed are methods, systems, and non-transitory, computer-readable storage media storing programs for phase-contrast x-ray imaging having improved quality and material discriminating power.

In some embodiments, a method comprises emitting source x-rays from a polychromatic source operating at an endpoint energy greater than or equal to 100 keV and generating a spot size greater than or equal to 0.5 mm; creating a series of periodically repeating apparent sources from the source x-rays using a source grating; patterning the series of periodically repeating apparent sources into a patterned beam using an object grating placed proximal to an object to be imaged and at distances $L_1$ from the source grating and $L_2$ from a detector grating, wherein the periodicities, P, of the source and object grating elements are related by $P_{source} = P_{object} * [(L_1 + L_2)/L_2]$ and wherein the source and object grating elements are substantially parallel; acquiring through the detector grating a first image with the object and a second image without the object, wherein the detector grating is oriented substantially orthogonally relative to the object grating and beam axis and wherein the object grating and the detector grating have a substantially equivalent x-ray attenuating factor; measuring visibilities of the object grating from the first and second images to determine an object grating visibility reduction due to scatter and beam hardening; measuring visibilities of the detector grating from the first and second images to determine a detector grating visibility reduction due to beam hardening; and applying a beam hardening correction based on a comparison of the object grating visibility reduction and the detector grating visibility reduction to generate a corrected scatter image.

In certain embodiments, the method can further comprise operating the polychromatic source at an endpoint energy greater than or equal to 150 keV, 160 keV, 175 keV, 200 keV, or 450 keV. In certain embodiments, the method can further comprise tilting the object grating and detector grating by rotating the gratings about an axis parallel to grating element lines. In certain embodiments, the method can further comprise tilting the source grating by rotating the gratings about an axis parallel to grating element lines.

In certain embodiments, the object grating is approximately equidistant between the source and the detector. In certain embodiments, the detector grating has a periodicity, $P_{detector}$, equivalent to that of the source grating, $P_{source}$. In certain embodiments, the object and detector gratings comprise an equivalent material and have an equivalent thickness. In certain embodiments, the source grating, object grating, detector grating, or combinations thereof have grating elements comprising a parallel line pattern.

In certain embodiments, the object to be imaged is a scatter test object calibration standard and further comprising performing a calibration of x-ray scatter, the scatter test object calibration standard comprising metal or metal oxide particles distributed in a polymer matrix and having a stepped-wedge geometry of at least three different thicknesses. In certain embodiments, the object to be imaged is a beam hardening test object calibration standard and further comprising performing a calibration of beam hardening, the beam hardening test object calibration standard comprising three or more homogeneous materials in a range of atomic numbers, with no large density variations on length scales between 10 nm and 200 microns, and have a thickness such that 10-90% of the x-ray intensity is transmitted through the test object.

In some embodiments, a system comprises a polychromatic x-ray source configured to provide source x-rays at an endpoint energy greater than or equal to 100 keV and a spot size greater than 0.5 mm; a source grating configured to create a series of periodically repeating apparent sources from the source x-ray; an object grating proximal to a position of an object to be imaged and at distances $L_1$ from the source grating and $L_2$ from a detector grating, wherein the periodicities of the source and object gratings are related by $P_{source} = P_{object} * [(L_1 + L_2)/L_2]$, the object grating configured to pattern the series of periodically repeating apparent sources into a patterned beam; and a detector grating having detector grating elements that are oriented orthogonally relative to object grating elements and a beam axis, the detector and object gratings having an equivalent x-ray attenuation factor. The system further comprises processing circuitry operably connected to the detector and configured to execute computer-readable instructions to acquire through the detector grating a first image with the object and a second image without the object; measure visibilities of the object grating from the first and second images to determine an object grating visibility reduction due to scatter and beam hardening; measure visibilities of the detector grating from the first and second images to determine a detector grating visibility reduction due to beam hardening; and apply a beam hardening correction based on a comparison of the object grating visibility reduction and the detector grating visibility reduction to generate a corrected scatter image.

In certain embodiments, the polychromatic source is configured to provide source x-rays at an endpoint energy greater than or equal to 150 keV, 160 keV, 175 keV, 200 keV, or 450 keV. In certain embodiments, the object grating and detector grating are positioned such that object grating elements and detector grating elements are tilted by a rotation of the gratings about an axis parallel to grating element lines. In certain embodiments, the source grating is positioned such that source grating elements are tilted by a rotation of the gratings about an axis parallel to grating element lines. In certain embodiments, the object grating is positioned approximately equidistant between the source and the detector. In certain embodiments, the detector grating has a periodicity, $P_{detector}$, equivalent to that of the source grating, $P_{source}$. In certain embodiments, the detector grating abuts the detector. In certain embodiments, the object and detector gratings comprise an equivalent material and have an equivalent thickness. In certain embodiments, the source grating, object grating, detector grating, or combinations thereof have grating elements comprising a parallel line pattern.

In some embodiments, a non-transitory computer readable storage medium stores one or more programs, the one or more programs comprise instructions, which when executed by one or more processors operably connected to an x-ray imaging system, cause the system to acquire through the detector grating a first image with the object and a second image without the object; measure visibilities of the object grating from the first and second images to determine an object grating visibility reduction due to scatter and beam hardening; measure visibilities of the detector grating from the first and second images to determine a detector grating visibility reduction due to beam hardening; and apply a beam hardening correction based on a comparison of the object grating visibility reduction and the detector grating visibility reduction to generate a corrected scatter image. The x-ray imaging system to which the processor(s) are operably connected comprise a polychromatic x-ray source configured to provide source x-rays at an endpoint energy greater than or equal to 100 keV and a spot size greater than 0.5 mm; a source grating configured to create a series of periodically repeating apparent sources from the source x-ray; an object grating proximal to a position of an object to be imaged band at distances $L_1$ from the source grating and $L_2$ from a detector grating, wherein the periodicities of the source and object gratings are related by $P_{source} = P_{object} * [(L_1 + L_2)/L_2]$, the object grating configured to pattern the series of periodically repeating apparent sources into a patterned beam; and a detector grating having detector grating elements that are oriented orthogonally relative to object grating elements and a beam axis, the detector and object gratings having an equivalent x-ray attenuation factor.

In certain embodiments, the non-transitory computer readable storage medium storing one or more programs, the one or more programs comprising instructions, which when executed by one or more processors operably connected to the x-ray imaging system further cause the x-ray imaging system to perform a calibration, wherein the object to be imaged is a scatter test object, a beam hardening test object, or both.

According to an aspect of the disclosed technology, systems include an x-ray source configured to emit an x-ray beam along a beam path and through an object arranged for inspection in a field of view of the x-ray source; and an object grating, an analyzer grating, a detector grating, and a detector arranged with respect to each other in the field of view; wherein the object grating includes object grating elements arranged in a first pattern, the detector grating includes detector grating elements arranged in a second pattern that is separable from the first pattern, and the analyzer grating includes analyzer grating elements that are arranged to correspond to a combination of the first pattern and second pattern; wherein the analyzer grating, and/or the object grating and detector grating, are configured to move relative to each other to different phase positions, and wherein the detector is configured to collect indirect moiré image data of the object at the different phase positions. In some examples, the wherein the analyzer grating, and/or the object grating and detector grating, are configured to move relative to each other to the different phase positions by translating the analyzer grating transverse to the beam path to the different phase positions while the detector grating and object grating are fixed. In some examples, the object grating and detector grating are configured to move relative to the analyzer grating to the different phase positions by translating the object grating and detector grating transverse to the beam path to the different phase positions while the analyzer grating is fixed. In some examples, the object grating elements include a set of parallel linear object grating elements, the detector grating elements include a set of parallel linear detector grating elements arranged perpendicularly with respect to the parallel linear object grating elements, and the analyzer grating elements include a set of crossed grating elements. Some examples further include one or more movement stages coupled to the analyzer grating and/or the object grating and detector grating to provide the relative movement to the different phase positions. In some examples, the relative movement to different phase positions includes a first set of positions along a first axis aligned with a direction of the first pattern and a second set of positions along a second axis aligned with a direction of the second pattern. In some examples, the relative movement to different phase positions further includes a set of one or more additional off-axis positions configured to average spectral information associated with the object grating and detector grating and thereby reduce moiré artifacts associated with the moiré image data. In some examples, the relative movement to different phase positions further includes a set of positions to define a latticed array of positions. In some examples, the relative movement to the different phase positions includes a third set of positions aligned with the direction of the first pattern and spaced apart from the first set of positions, and a fourth set of positions aligned with the direction of the second pattern and spaced apart from the second set of positions. In some examples, the third set of positions is spaced apart from the first set of positions by a pi-shift and the fourth set of positions is spaced apart from the second set of positions by a pi-shift. Some examples further include a processor and memory configured with processor executable instructions which cause the processor to apply a beam hardening correction to the indirect moiré image data. Some examples further include a source grating situated adjacent to the x-ray source and configured to receive the x-rays from the x-ray source to produce a plurality of source grating x-ray sources. In some examples, the object grating, analyzer grating, and detector gratings are arranged in the field of view along the beam path such that the analyzer grating precedes the detector, the detector grating precedes the analyzer grating, and the position of the object to be inspected precedes the analyzer grating. In some examples, the object grating precedes the position of the object to be inspected.

According to another aspect of the disclosed technology, methods include emitting an x-ray beam from an x-ray source along a beam path and through a position for an object arranged to be inspected in a field of view of the x-ray source, wherein an object grating, an analyzer grating, a detector grating, and a detector are arranged with respect to each other in the field of view, wherein the object grating includes object grating elements arranged in a first pattern, the detector grating includes detector grating elements arranged in a second pattern that is separable from the first pattern, and the analyzer grating includes analyzer grating elements that are arranged to correspond to a combination of the first pattern and second pattern; moving the analyzer grating, and/or the object grating and detector grating, relative to each other to different phase positions; and detecting indirect moiré image data with the detector at the different phase positions. In some examples, the moving comprises translating the analyzer grating transverse to the beam path to the different phase positions while the detector grating and object grating are fixed. In some examples, the moving comprises translating the object grating and detector grating transverse to the beam path to the different phase positions while the analyzer grating is fixed. In some examples, the object grating elements include a set of parallel linear object grating elements, the detector grating elements include a set of parallel linear detector grating elements arranged perpendicularly with respect to the parallel linear object grating elements, and the analyzer grating elements include a set of crossed grating elements. In some examples, the moving comprises moving the analyzer grating, and/or the object grating and detector grating, relative to each other to the different phase positions with one or more movement stages. In some examples, the moving to the different phase positions comprises moving to a first set of positions along a first axis aligned with a direction of the first pattern and moving to a second set of positions along a second axis aligned with a direction of the second pattern. In some examples, the moving to the different phase positions further comprises moving to a third set of positions aligned with the direction of the first pattern and spaced apart from the first set of positions, and to a fourth set of positions aligned with the direction of the second pattern and spaced apart from the second set of positions. In some examples, the third set of positions is spaced apart from the first set of positions by a pi-shift and the fourth axis is spaced apart from the second set of positions by a pi-shift. In some examples, the moving to the different phase positions further includes moving to a set of one or more additional off-axis positions configured to average spectral information associated with the object grating and detector grating and thereby reduce moiré artifacts associated with the moiré image data. In some examples, the moving to the one or more additional off-axis positions includes moving to a set of positions such that the different phase positions comprise a crossed or L-shaped set of positions and a diagonal set of positions. In some examples, the moving to the one or more additional off-axis positions includes moving to a set of positions such that the different phase positions comprise a latticed array of positions. Some examples further include, with a processor and memory configured with processor executable instructions, applying a beam hardening correction to the indirect moiré image data. In some examples, the object grating, analyzer grating, and detector gratings are arranged in the field of view along the beam path such that the analyzer grating precedes the detector, the detector grating precedes the analyzer grating, and the position of the object to be inspected precedes the analyzer grating. In some examples, the object grating precedes the position of the object to be inspected.

According to another aspect of the disclosed technology, non-transitory computer readable storage media are provided, storing one or more programs, the one or more programs comprising instructions, which when executed by one or more processors operably connected to an x-ray imaging system that comprises: an x-ray source configured to emit an x-ray beam along a beam path and through an object arranged for inspection in a field of view of the x-ray source; and an object grating, an analyzer grating, a detector grating, and a detector arranged with respect to each other in the field of view; wherein the object grating includes object grating elements arranged in a first pattern, the detector grating includes detector grating elements arranged in a second pattern that is separable from the first pattern, and the analyzer grating includes analyzer grating elements that are arranged to correspond to a combination of the first pattern and second pattern; wherein the analyzer grating, and/or the object grating and detector grating, are configured to move relative to each other to different phase positions, and wherein the detector is configured to collect indirect moiré image data of the object at the different phase positions; causes the x-ray imaging system to collect the indirect moiré image data at the different phase positions.

The purpose of the foregoing summary and the latter abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. Neither the summary nor the abstract is intended to define the invention of the application, which is measured by the claims, nor is it intended to be limiting as to the scope of the claims in any way.

BRIEF DESCRIPTION OF THE DRAWINGS

FIG. 5 includes an image of a Fourier transform of an image obtained by enhanced phase-contrast x-ray imaging as described herein.

FIG. 6 is a graph showing corrected scatter ratio as a function of grid frequency (in LPI) for two different particle sizes.

FIG. 10A is a conventional attenuation image. FIG. 10B is an attenuation image with corrected scatter overlay according to embodiments described herein. Propellants present in the bag show scatter, as do business cards, a watch band, and tic tac candies. Chapstick next to the model rocket engine looks similar by shape, but does not exhibit scatter.

FIGS. 11A and 11B are images related to one embodiment of a calibration standard. FIG. 11A is a photograph of ZnO scatter step wedge calibration standards. FIG. 11B are beam-hardening corrected scatter images taken at high energy (160 kV with 2 mm Cu and 2 mm Al filtration) and at low energy (100 kV with 2 mm Al filtration).

FIGS. 31A-33B are phase contrast image pairs comparing uncorrected with corrected images of a test object for absorption (31A-31B), contrast ratio (32A-32B), and phase shift (33A-33B).

FIGS. 34A-34H are schematic depictions of unit cells for object, detector, and analyzer gratings along with various overlaps produced by relative movement between them.

DETAILED DESCRIPTION

Figure 1A:
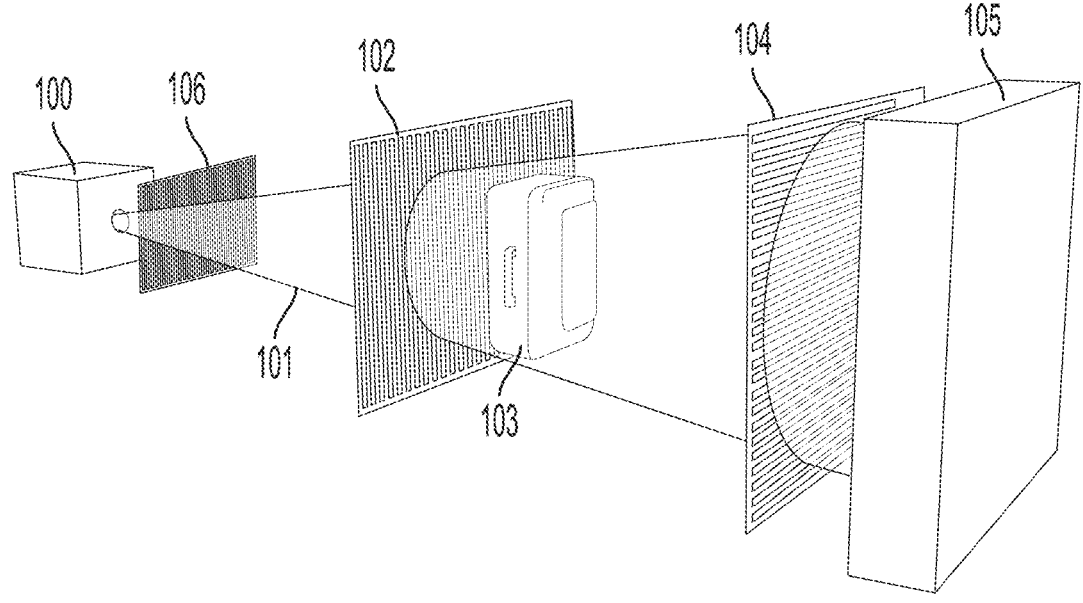
FIGS. 1A and 1B include a schematic diagram and a flow chart, respectively, depicting embodiments described herein.

Phase contrast x-ray imaging or gratings-based phase contrast imaging can allow for detection of small deviations in the direction of an x-ray as it passes through a material. These deflections, specifically scatter, can be used to detect texture in a material, such as a powder or a composite, below the imaging resolution of the system. The inventors have determined that measurements at high energies can provide scatter signatures indicative of sub-resolution texture within a sample in order to help identify materials and that the systems, methods, and storage media described herein can be relevant for applications ranging from medical imaging to materials characterization to security screening.

Embodiments described herein can be utilized for discernment of materials properties, especially in non-destructive examination applications. For example, material wetting or compression could be examined (e.g., concrete, plaster, materials that are formed through compression of powders), as could fiber orientations in materials made from carbon fibers or other fibrous materials. Medical applications are also possible, including diagnostic imaging with either radiography or CT. Scatter has been shown to give enhanced contrast for lung structure and for bones. Finally, additional security screening applications may be possible, such as detecting 3-D fabricated parts based on texture or locating powdered materials in mail screening or vehicle screening. Conventional airport security relies on dual-energy x-ray images that can be used to estimate material density and effective atomic number; these two features are relied upon to discriminate threat objects from benign consumer products. However, the estimation from conventional security scanners is often insufficient to effectively distinguish and identify threat objects. Phase contrast imaging can provide additional materials signatures from x-ray measurements: attenuation, which is similar to a conventional x-ray image; refraction or phase, which is based on electron density variations and can be sensitive to low-Z materials; and scatter, which detects the presence of texture (such as powders or composites) below the imaging resolution of the system. The addition of new signatures increases the number of features which can be used for material discrimination, potentially reducing false alarm rates during security screening. Furthermore, one mode may have a lower detection limit than absorption, enabling the detection/identification of additional items and/or features.

Current phase contrast imaging systems typically rely on a grid which produces an x-ray interference pattern (typically with a period of a few microns) and an analyzer grid matched to the undistorted interference pattern. These systems require sub-micron stability and are very difficult to scale to higher, more penetrating energies; they often operate at energies below 100 kVp. When grid fabrication for energies above 100 kVp is possible, it is difficult and expensive. First, the period should be smaller than the coherence length (which decreases as energy increases). Second, the thickness of the attenuating parts of the grid need to be thick enough to stop the x-rays, and this becomes larger at high energies. The net effect is that fabrication with fine feature sizes but extremely large aspect ratios are required; something that is often impractical to manufacture.

For aviation security, phase contrast imaging is not currently used. Dual energy systems provide estimates of material density and effective atomic number to help discriminate benign materials from threats. Adding phase contrast would allow refraction information and texture information to be measured in addition to dual energy, providing a broader basis of material signatures for discriminating materials, and potentially reducing false alarm rates.

Embodiments described herein can detect sub-resolution texture using an object grid as a patterning object in the beam and at a standoff distance from the detector, where the image of the object grid is projected. If a sample containing sub-resolution density variations (such as a powder) is placed near the object grid, the refractive index variations within the object will cause deflections of the x-ray beam, ultimately causing blurring of the projected object grid pattern. This can be described as a reduction in visibility of the pattern.

Importantly, traditional phase contrast imaging occurs at relatively low energies (<100 kVp). Embodiments described herein measure x-ray refraction and scatter at higher energies, while making corrections for spectral effects which can cause spurious scatter-like signals. The embodiments enable the use of high energies which are relevant for NDE applications including airport screening (e.g. 160 kVp). Indeed, the inventors have measured scatter at energies as high as 450 kVp.

The x-ray energies referred to herein are endpoint energies. An x-ray tube produces a polychromatic spectrum of x-rays, with a peak energy defined by the electron energy impinging upon the anode. As the x-rays pass through the object, some energies are more readily absorbed than others, which means that the spectrum behind the object is different than the original spectrum. This in turn changes the visibility of the grid lines. For most materials in the range of energies described herein for x-ray imaging, higher energies are more penetrating than lower energies, which are more readily absorbed in materials. This means that the original visibility of an object grid will tend to be higher for lower energies. When a polychromatic beam passes through an object, the lower energies in the spectrum are more readily absorbed, an effect referred to as "beam hardening". In this case, the inventors have determined that since the resulting spectrum has more intensity at high energy than the original spectrum, this will cause a reduction in the visibility of the object grid, even in the absence of actual scattering in the object. As the system is run at higher energies and used to interrogate more attenuating objects, the changes in beam spectrum caused by object attenuation also lead to changes in grid pattern visibility, which must be corrected for in order to isolate the visibility reduction due to scatter.

Embodiments described herein differ from other three-grid combination systems and methods at least because some embodiments enable high-energy operation using a polychromatic radiography source (e.g., energies above 100 kVp, 125 kVp, 150 kVp, 160 kVp, 175 kVp, 200 kVp, or 450 kVp, with a spot size, defined as the spatial extent of the region on the x-ray tube anode from which x-rays are emitted, of at least 0.5 mm), in contrast to a synchrotron source or a conventional source operated at lower energies and/or spot sizes. In certain embodiments, the source operates with a current ranging from 0.1 to 1000 milliamps.

In particular, embodiments described herein differ from a three-grid Talbot-Lau interferometer, which uses a source grid to increase spatial coherence, an object grid that forms an interference pattern, and an analyzer grid that detects small changes in the very small interference pattern. In other words, the object grid is a phase element and sets up an interference pattern that impinges on the analyzer grid in order to help detect deviations in the interference pattern without resolving it directly. The source grid in the Talbot-Lau configuration is required to form a sufficiently smooth wave front to establish an interference pattern and the required coherence. In contrast, embodiments described herein utilize large spot sizes (at least 0.5 mm) while retaining the ability to not blur the pattern image and to improve resolution, not coherence. The Talbot-Lau analyzer grating is aligned with the object grating and matches the projected object grating period. Another distinction of present embodiments compared to a Talbot-Lau-style interferometer is the absence of a requirement for gratings which are both fine (period of 5 microns or less) and extremely high aspect ratio (often 10:1, and up to 100:1 for 100 keV), sub-micron alignment and stability, and highly precise (sub-micron) stepping of an analyzer grid placed near the detector. This combination is difficult and impractical for many applications for conventional systems. In contrast, some embodiments described herein utilize gratings having grating elements comprising parallel channels with an aspect ratio less than 10:1, 8:1, 5:1, or 3:1 when the source operates at an energy of at least 100 kVp. In certain embodiments, the gratings can have a scale greater than a 2 micron period, a 5 micron period, a 10 micron period, a 25 micron period, a 50 micron period, or a 100 micron period, which can enable different fabrication methods that are much easier.

In summary, the inventors have determined that the combination of a directly imaged, attenuation-based object grid, the use of a source grid to improve imaging of the object grid using a high-energy polychromatic source with a large spot size, and the use of a stationary detector grid having gratings oriented substantially orthogonally to that of the object grid, addresses the artifacts and beam hardening effects that limit the quality and discriminatory power of high-energy x-ray imaging that includes phase contrast. The object grid is visible on the detected image and is, therefore, sufficiently coarse to be directly visualized on the detector. However, this coarseness can reduce scatter sensitivity. In certain embodiments, the object grid is positioned substantially equidistant between the source and detector in order to optimize contrast for most samples by providing 2× magnification of the grid on the detector. Furthermore, most high energy sources have a large x-ray tube spot size, so their use is enabled by the added source grid. Finally, high energy applications typically involve highly attenuating objects, making the beam hardening correction critical for accurate results, which requires the detector grid. Thus, all three grids operate synergistically to enable embodiments disclosed herein.

The explanations of terms and abbreviations herein are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, distances, energies, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximations unless the word "about" is recited.

Referring to FIG. 1A, a diagram summarizes one embodiment of a system for beam-hardening-corrected, phase-contrast, x-ray imaging. As illustrated, the embodiment comprises three x-ray anti-scatter grids having parallel line grating elements. The source grid 106 is placed at the x-ray source 100, the object grid 102 is in proximity to an object 103 being imaged, and the detector grid 104 abuts the detector 105. The source and detector are placed some distance apart, with an object being imaged located between the source and the detector. The source is operated at high energies and generates a large spot size. The object grid can be on the source or detector side of the object and the object grid lines are spaced at period, $P_{object}$. The source grid is placed near the x-ray source with period, $P_{source}$ substantially equal to $P_{object} \cdot [(L_1 + L_2)/L_1]$, wherein $L_1$ and $L_2$ are distances from the source to the object and from the object to the grid, respectively. In certain embodiments, the distance between the source and the object and the distance between the object and detector are substantially equivalent. In certain embodiments, the detector grating has a periodicity that is equivalent to that of the source grating. The fundamental relationship is between $P_{source}$ and $P_{object}$, to get the patterns to overlay when projected onto the detector. As a matter of convenience, efficiency, and/or optimization to set $P_{detector}$ equal to the projected $P_{object}$ to make the regions around their respective Fourier peaks are about the same size in Fourier space. When $L_1$ and $L_2$ are equal, $P_{source}$ can equal $P_{detector}$.

The source grid can compensate for a large x-ray tube spot size, which can be detrimental to being able to resolve the lines of the object grid. In other words, the source grid can allow the object grid to be imaged on the detector more clearly. The detector grid is placed at the detector and the orientation of the grating elements is substantially 90 degrees rotated relative to those of the object grid. With regard to rotation of the detector grating elements, substantially can refer to an error of ±1, ±2, or ±5 degrees. In certain embodiments, the error in detector grating rotation angle should be less than that which would avoid overlap of the first harmonics in Fourier space.

The object grid and detector grid have substantially the same attenuating factor. With regard to the attenuating factor, substantially refers to an error of ±1%, ±3%, ±5%, or ±10%. For example, the object and detector grids can comprise the same material and same thickness. The detector grid is used to correct for artifacts caused by beam hardening, where the spectrum of the beam is changed by attenuating objects. When the object grid is substantially equidistant from the source and detector, the source and detector gratings can have substantially the same grating element period.

Figure 1B:
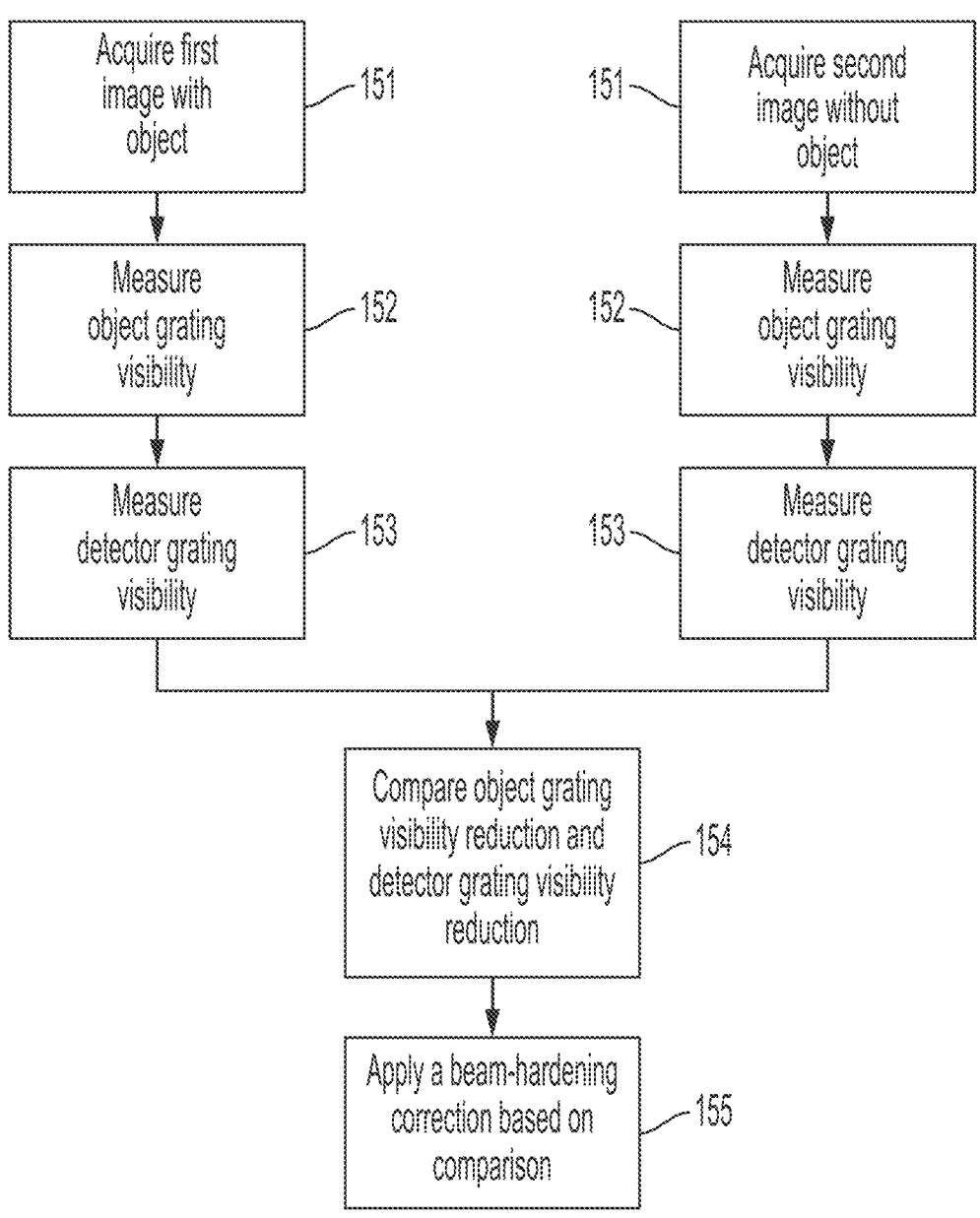

FIG. 1B includes a flowchart summarizing one example of a computer-implemented method of beam-hardening correction of phase-contrast x-ray imaging. The method can be embodied by non-transitory, computer-readable storage media storing instructions that can be executed to perform the method. In the illustrated example, first and second images are acquired with and without the object to be imaged 151. The "first image" and "second image" terms do not refer to chronological sequence; the images can be acquired in any order. The object grating visibilities are measured in both images 152. Similarly, the detector grating visibilities are measured in both images 153. The visibilities are compared 154 to determine the object grating visibility reduction and the detector grating visibility reduction. Based on the comparison of the reductions 154, a beam-hardening correction is applied 155 to yield a corrected phase-contrast x-ray image.

Non-transitory as used herein when referring to a computer-readable storage medium, is a limitation of the medium itself (i.e., tangible, not a propagating electromagnetic signal) as opposed to a limitation on data storage persistency. The term is not intended to otherwise limit the type of physical computer-readable storage device that is encompassed by the phrase computer-accessible medium or memory. For instance, the terms "non-transitory computer readable medium" or "tangible memory" are intended to encompass types of storage devices that do not necessarily store information permanently, including but not limited to, computer-readable media that store data only for short periods of time and/or only in the presence of power, such as register memory, processor cache and Random Access Memory (RAM). Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

Figure 2:
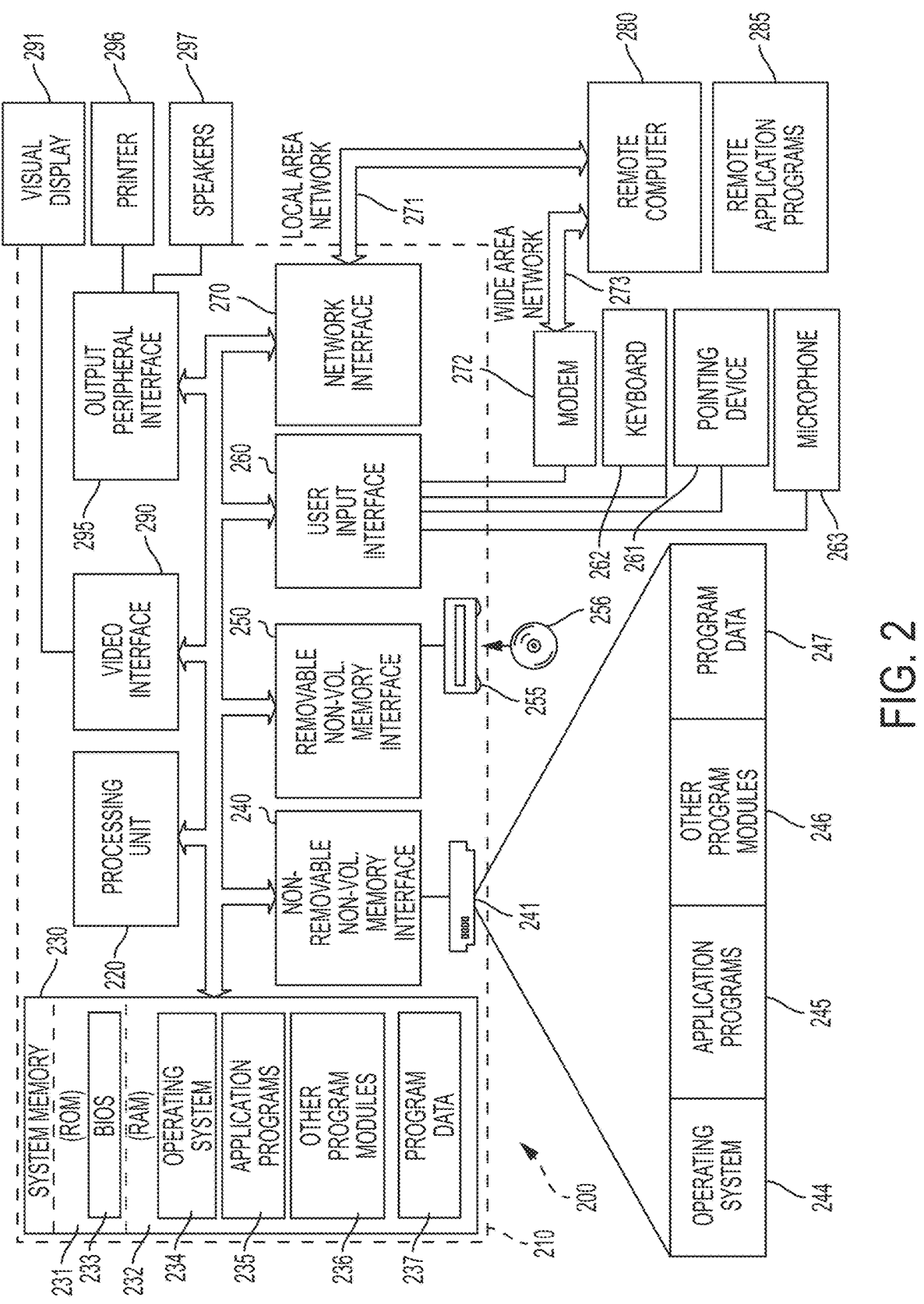
FIG. 2 is a diagram of one embodiment of a computational system for enhanced phase-contrast x-ray imaging and/or beam-hardening correction.

FIG. 2 is one embodiment of a computational system or computing environment to which an enhanced phase-contrast x-ray imaging system can be operably connected. Alternatively, the computational system can be integrated within an enhanced phase-contrast x-ray imaging system. In one example, a computing environment such as shown in FIG. 2 can be used to control operation of the imaging system. The computing environment can further be used to acquire images and to perform beam-hardening corrections as described elsewhere herein.

With reference to FIG. 2, an example system for implementing some embodiments includes a general-purpose computing device in the form of a computer 210. Components of computer 210 may include, but are not limited to, a processing unit 220 (which is not limited to CPUs, but can comprise GPUs), a system memory 230, and a system bus 221 that couples various system components including the system memory to the processing unit 220. The system bus 221 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. Memory and programs described herein be deployed in corresponding portions of FIG. 2.

Computer 210 typically includes a variety of computer readable media. Computer readable media can be any available media that can be accessed by computer 210 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, sash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 210. Communication media typically embodies computer readable instructions, data structures, program modules or other data in a transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

The system memory 230 includes computer storage media in the form of volatile and/or nonvolatile memory such as read only memory (ROM) 231 and random-access memory (RAM) 232. A basic input/output system 233 (BIOS), containing the basic routines that help to transfer information between elements within computer 210, such as during startup, is typically stored in ROM 231. RAM 232 typically contains data and/or program modules that are immediately accessible to and/or presently being operated on by processing unit 220. By way of example, and not limitation, FIG. 2 illustrates operating system 234, application programs 235, other program modules 236, and program data 237.

The computer 210 may also include other removable/nonremovable volatile/nonvolatile computer storage media. By way of example only, FIG. 2 illustrates a hard disk drive 241 that reads from or writes to non-removable, nonvolatile magnetic media, and an optical disk drive 255 that reads from or writes to a removable, nonvolatile optical disk 256 such as a DVD or other optical media. Other removable/non-removable, volatile/nonvolatile computer storage media that can be used in the exemplary operating environment include, but are not limited to, magnetic tape cassettes, sash memory cards, DVDs, digital video tape, solid state RAM, solid state ROM, and the like. The hard disk drive 241 is typically connected to the system bus 221 through a non-removable memory interface such as interface 240, and optical disk drive 255 are typically connected to the system bus 221 by a removable memory interface, such as interface 250.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The drives and their associated computer storage media discussed above and illustrated in FIG. 2, provide storage of computer readable instructions, data structures, program modules and other data for the computer 210. In FIG. 2, for example, hard disk drive 241 is illustrated as storing operating system 244, application programs 245, other program modules 246, and program data 247. Note that these components can either be the same as or different from operating system 234, application programs 235, other program modules 236, and program data 237. Operating system 244, application programs 245, other program modules 246, and program data 247 are given different numbers here to illustrate that, at a minimum, they are different copies.

A user may enter commands and information into the computer 210 through input devices such as a keyboard 262, a microphone 263, and a pointing device 261, such as a mouse, trackball or touch pad. Other input devices (not shown) may include a joystick, game pad, satellite dish, scanner, or the like. These and other input devices are often connected to the processing unit 220 through a user input interface 260 that is coupled to the system bus, but may be connected by other interface and bus structures, such as a parallel port, game port or a universal serial bus (USB). A visual display 291 or other type of display device is also connected to the system bus 221 via an interface, such as a video interface 290. Video interface 290 can comprise a graphics card having a GPU. The GPU be used for computations. In addition to the monitor, computers may also include other peripheral output devices such as speakers 297 and printer 296, which may be connected through an output peripheral interface 295.

The computer 210 is operated in a networked environment using logical connections to one or more remote computers, such as a remote computer 280. The remote computer 280 may be a personal computer, a hand-held device, a server, a router, a network PC, a peer device or other common network node, and typically includes many or all of the elements described above relative to the computer 210. The logical connections depicted in FIG. 2 include a local area network (LAN) 271 and a wide area network (WAN) 273, but may also include other networks. Such networking environments are commonplace in offices, enterprise-wide computer networks, intranets and the Internet.

When used in a LAN networking environment, the computer 210 is connected to the LAN 271 through a network interface or adapter 270. When used in a WAN networking environment, the computer 210 typically includes a modem 272 or other means for establishing communications over the WAN 273, such as the Internet. The modem 272, which may be internal or external, may be connected to the system bus 221 via the user input interface 260, or other appropriate mechanism. In a networked environment, program modules depicted relative to the computer 210, or portions thereof, may be stored in the remote memory storage device. By way of example, and not limitation, FIG. 2 illustrates remote application programs 285 as residing on remote computer 280. It will be appreciated that the network connections shown are exemplary and other means of establishing a communications link between the computers may be used.

Examples and Comparisons

To further illustrate certain embodiments of the disclosed methods, systems, and computer-readable storage media, and to provide various comparative analyses and data, below are some examples with comparison test data.

Figure 3:
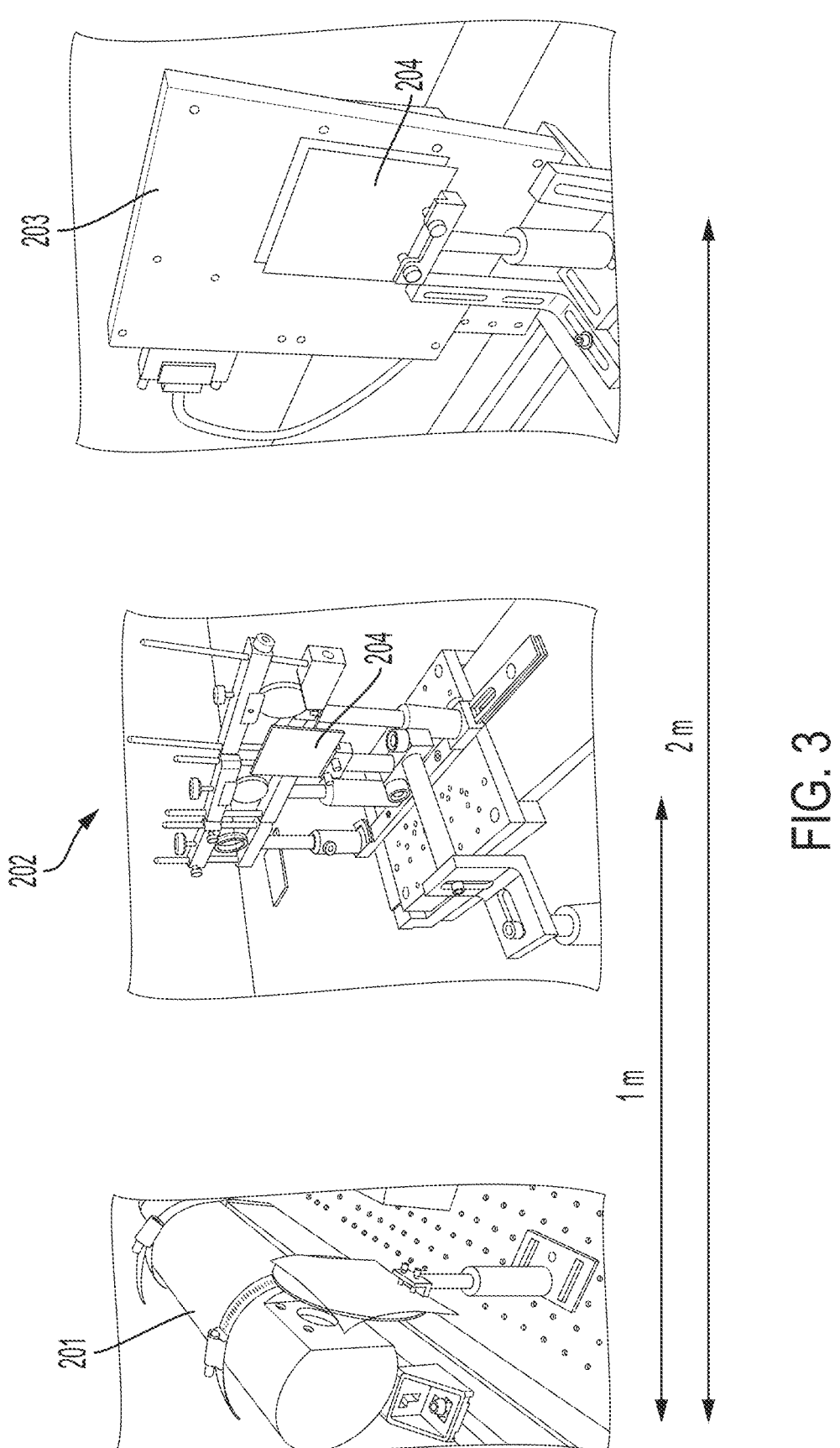
FIG. 3 includes photos of one embodiment of an arrangement of source, object, and detector gratings in an enhanced phase-contrast x-ray imaging system.

Photos of a basic system, including a source, object grid, and detector are shown in FIG. 3. The x-ray source 201 used was a Comet MXR-160HP/11 x-ray tube with a maximum energy of 160 kV. The maximum power was 1800 W with a 1 mm spot size or 800 W with a 0.4 mm spot size. In some embodiments, when the spot size is too large to resolve the object grid on the detector, a source grid is necessary. The relationship describing the spot size above which the ability to resolve the object grating is reduced can be expressed as $W_{source} \geq (L_1 + L_2) * P_{obj} / L_2$, where w is the spot size of the source, $L_1$ is the source-to-object distance, and $L_2$ is the object-to-detector distance. Test data shown below used 1 mm Al and 0.1 mm Cu to filter the spectrum of the beam and reduce the flux at very low photon energies. The working distance from source to detector 203 was set at 2 m, and the detector used initially was a CMOS X-ray detector (e.g., Shad-o-Box® 4k) with a 10 cm×10 cm field of view, 48 μm pixel pitch, and a $Gd_2O_2S$:Tb scintillator (Teledyne DALSA®). The object and object grid 202 were placed halfway between the source and detector, resulting in a two-times magnification and good sensitivity to the small angular deflections by the sample. The beam pattern was created with commercial anti-scatter grids 204 used for medical imaging, consisting of parallel line patterns between 85 and 285 lines per inch (LPI). Typically, the grids are made of lead and aluminum sheets interspersed, but the finest grid was made with carbon fiber between lead sheets. A second grid, approximately half the object grid's spatial frequency, was oriented such that the grid lines were perpendicular to those of the object grid and was placed directly in front of the detector in order to correct for beam hardening, as described elsewhere herein.

Figure 4:
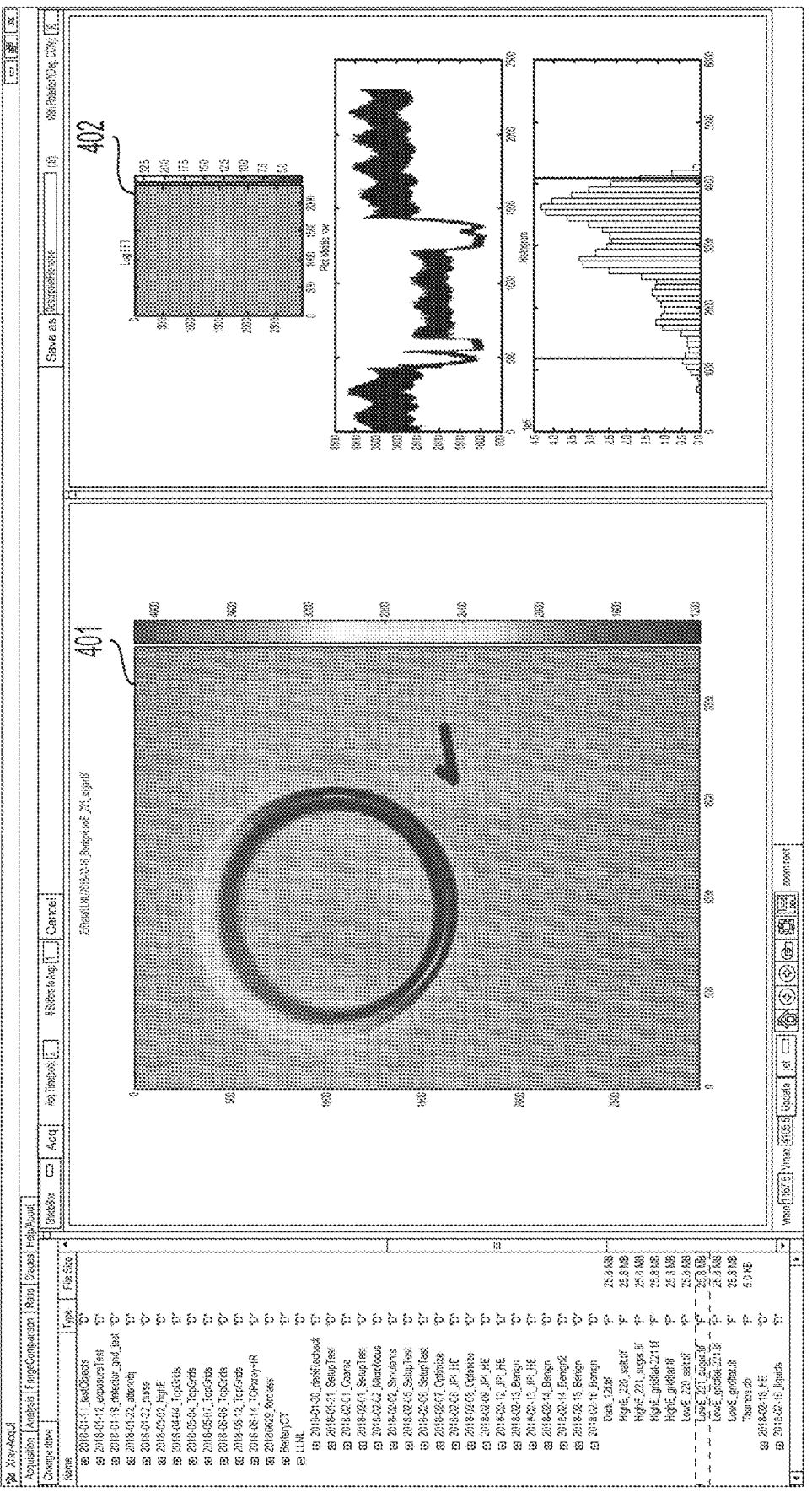
FIG. 4 is a screenshot of one example of image acquisition and processing software.

Custom software was developed to handle both data acquisition and extraction of absorption, phase, and scatter images. Frames were acquired from the detector, summed, and saved as floating-point tiff files; this file type allowed viewing as an image while preserving raw numbers from the detector and the full bit-depth of the detector. The interface to the data acquisition and processing software is shown in FIG. 4.

Raw images 401 resembled a normal attenuation image, but with fine vertical and horizontal lines visible from the object and detector grids. A Fourier-based processing method was used. First, a Fourier transform 402 is taken of the image. For a system with parallel line grids, peaks will be visible in the Fourier transform corresponding to the spatial frequency of the grid. In FIG. 5, peaks to the right and left of center correspond to the first harmonic associated with the object grid (which was oriented with its grid lines vertical), and the peaks at top and bottom are the first harmonic of the detector grid (which was oriented with its lines horizontal. The region around the first harmonic when an object is present is compared with the same region a grid-only image (no sample). Pattern displacements of the object grid were determined based on the phase values in a region of the Fourier transform around the first harmonic. These were interpreted as refraction and formed the differential phase contrast image. Pattern visibility, V, is calculated based on the ratio of the inverse Fourier transform of the region around the first harmonic to the inverse Fourier transform of the region around the zeroth harmonic, but can be more simply understood as the amplitude of the projected grid pattern divided by the mean. Pattern visibility reduction, $V/V_0$, which compares pattern visibility with an object present to pattern visibility without, was interpreted as scatter. Note, visibility can be reduced not only by scattering effects but also by beam hardening, since a harder spectrum may result in less modulation of the object grid. To correct for this, a detector grid was chosen that has similar attenuation properties as the object grid so that it would be similarly affected by beam hardening. This grid was placed as close as possible to the detector to minimize the effects of scatter on the projected pattern. The ratio of the scatter image to the apparent scatter in the detector grid image produced a correction to remove the portion of the visibility loss due to beam hardening.

The first study performed was a test of the system sensitivity to the object grid spatial frequency. Calibration standards were constructed of iron oxide (i.e., $Fe_3O_4$) nanoparticles dispersed in epoxy at a 20% volume fraction. Objects were 6 mm thick and were constructed with two different sizes of particles: 30 nm and 1 μm. A source spectrum with a peak energy of 40 kV was used. Results are shown in FIG. 6, which shows the corrected scatter ratio, which is the visibility reduction at the object grid after correcting for beam hardening as a function of grid frequency (in lines per inch). For the 1 mm particle sample, as the grid frequency was increased, the scatter increased approximately linearly. For the 30 nm particles, the response was independent of grid frequency. This is consistent with theoretical descriptions of the measurement process where the x-ray interactions are due to Small Angle X-ray Scattering (SAXS) and the response of the system is characterized by a parameter known as the correlation length. The correlation length of the measurement at 40 kV ranges between 50 and 300 μm depending on the grid frequency. For particles much larger than the correlation length, scatter signal increases with larger grating spatial frequencies, while for samples much smaller than the correlation length, scatter signal should be independent of gratings frequency.

Figure 7:
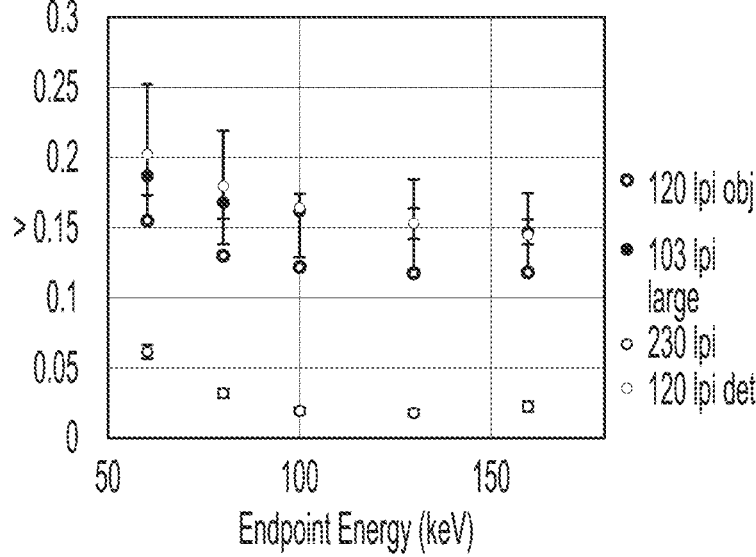
FIG. 7 is a graph showing fringe visibility as a function of endpoint energy and grid spatial frequency.

For explosives detection, particles larger than the correlation length are of primary interest. In certain embodiments, texture is considered to be in the 1-1000 microns for what is defined as a powder. The correlation length is inversely proportional to energy, so increasing the spatial frequency of the object grid as much as possible will improve measurement sensitivity. For signatures of explosive and benign materials that, when textured, typically have variations on length scales ranging from microns to millimeters in size, a finer object grid (higher spatial frequency) is generally advantageous. However, as grid frequency decreases, imaging the projected grid pattern becomes more difficult. This can be caused by the finite size of the x-ray source region in the tube, finite resolution at the detector, and by limited attenuation in a finely patterned grid (as spatial frequencies increase. Therefore, higher aspect ratio fabrication is required in order to retain sufficient thickness to modulate the beam). To examine these effects, we measured the visibility with no object present for several grids and measurement geometries. Higher visibilities indicate a larger fraction of the beam intensity is available for detecting refraction and scatter; lower visibilities will lead to noisier measurements. FIG. 7 is a graph that shows visibility as a function of endpoint energy for 103, 120, and 230 LPI grids placed halfway between source and detector, and a 120 LPI grid placed near the detector. Overall visibility values range from less than 0.05 up to 0.30. Visibility decreases with energy, as the beam becomes more penetrating, but changes relatively slowly at higher energies. The coarsest grid, at 103 LPI, showed the highest visibilities and the finest grid, 230 LPI, showed the lowest. For the 120 LPI grid, measurements were done with the grid halfway between source and detector, where pattern visibility was equally sensitive to resolution limitations due to the source and to the detector, and with the grid near the detector, where resolution was strongly dependent on the detector and independent of the source spot size. The grid showed higher visibility at the detector position, indicating that for grids halfway between source and detector, the source spot size was the dominant factor in reducing visibility.

Figure 8:
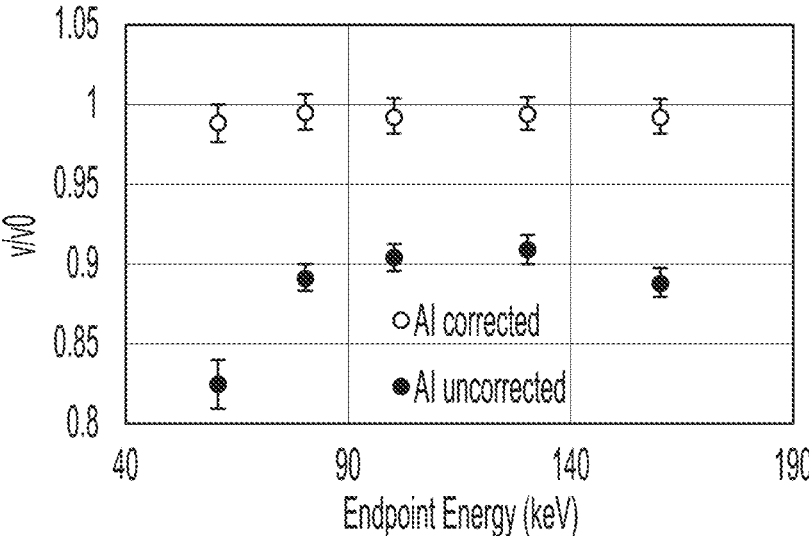
FIG. 8 is a graph showing visibility reduction as a function of endpoint energy, for a 1.26 cm Al sample (shown with and without the beam hardening correction).

The beam hardening correction was tested as a function of energy using a 1.26 cm thick section of aluminum (for reference, the mean free path for attenuation in Al ranges from 0.68 cm at 40 keV to 2.7 cm at 160 keV). This was selected as a material that was expected to be homogeneous over any texture length scales that the measurement would be sensitive to (e.g., nm to μm). Fringe visibility reduction ($V/V_0$, where $V_0$ is the grid visibility without an object present) is plotted in FIG. 8 as a function of endpoint energy, both for the object grid alone (Al uncorrected), and for the object grid after beam-hardening correction by the detector grid (Al corrected). We can verify that, although the raw object grid (uncorrected) shows substantial decreases in fringe visibility, particularly at low energies, the correction by the detector grid results in calculated visibility reduction numbers independent of peak energy and consistent with a ratio of 1, indicating a homogeneous, non-scattering material, as expected.

Figure 9:
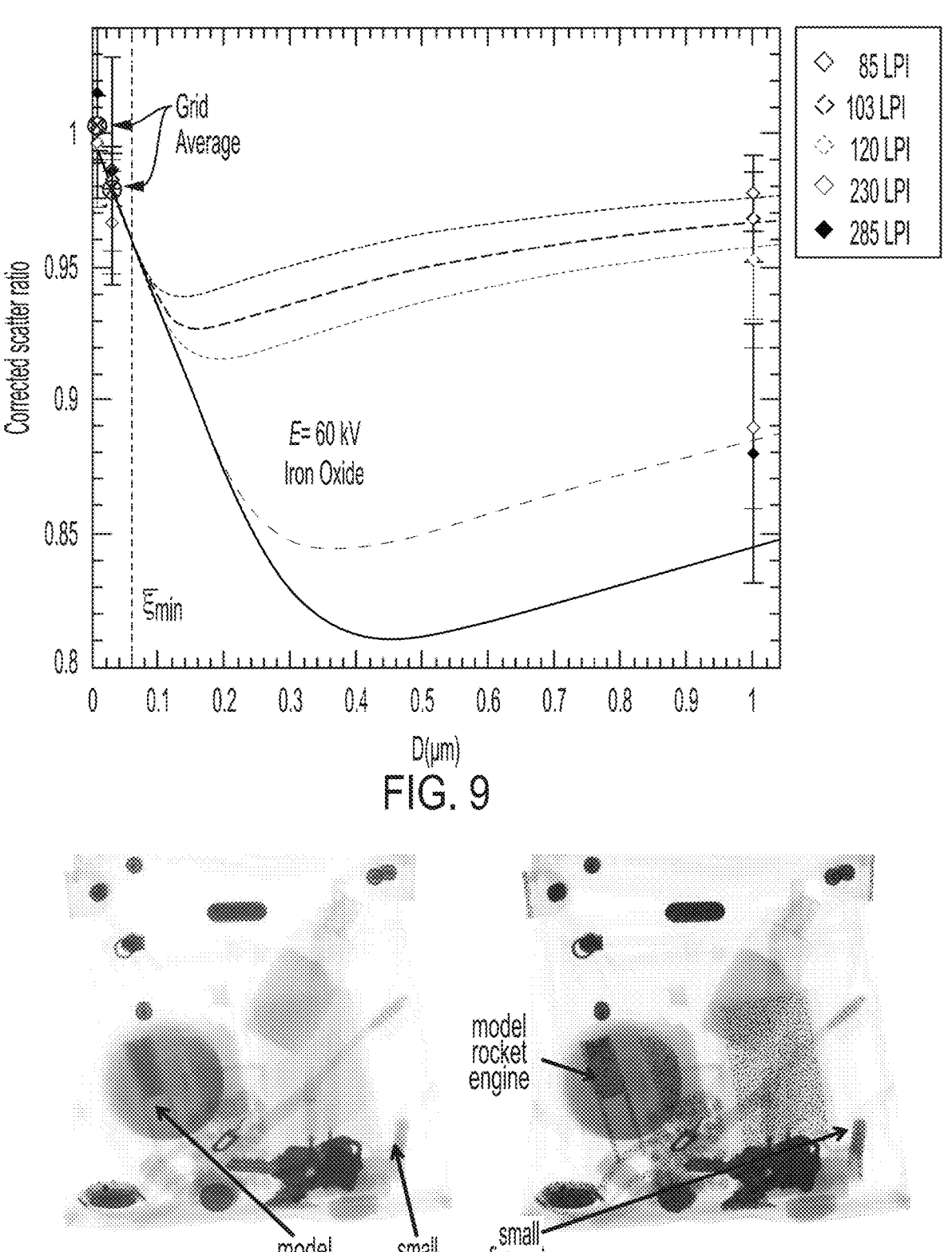
FIG. 9 is a graph showing corrected scatter ratio as a function of particle size, for a 60 kV spectrum. Theoretical predictions are shown as solid lines; measurements are indicated as points with error bars FIGS. 10A and 10B include images of a small bag (8"×9") as in a security screening context.

The scatter for a typical gratings-based setup is expected to be dominated by small angle x-ray scattering (SAXS), a mechanism for elastic scattering that produces a spectrum as a function of a scattering vector reflecting the distribution of spatial features in the sample. For the gratings-based measurement, results are not resolved as a function of scattering vector, but sensitivity is greatest near the scattering angle defined by the object grid-to-detector distance, d, and the size of the projected grid period, $P_{projected}$. The momentum transfer associated with this scattering angle can be related to a correlation length in the material, $\xi_{corr}=d*hc$ ($P_{projected} \cdot E$), where E is the photon energy and E/hc is the photon wavelength; this correlation length is closely related to the particle size that produces peak scatter intensity. In FIG. 9, we plot corrected scatter ratio as a function of particle size for a 60 kV spectrum. Solid lines are theoretical estimates for a range of grating frequencies. As grating frequency was increased, the effects on scatter ratio become larger, and the correlation length increased as well, leading to peak scattering at increasingly large particle size. Measured results are shown for iron oxide nanoparticles at 7 nm, 30 nm, and 1000 nm mean particle size; they were generally consistent with theoretical predictions.

The measurements shown established that fringe visibility is possible at energies up to 160 kV and illustrated the importance of correcting for beam hardening in interpreting fringe visibility reduction as scatter. A tradeoff is demonstrated between increased scatter signal for higher spatial frequency grids and reduced overall visibility as grid frequency is increased, which will lead to lower signal-to-noise.

A source grid can improve the ability to resolve the object grating. The source grid is aligned parallel to the object grid, with half the spatial frequency (when the object grid was placed substantially equidistant between the source and detector); this results in multiple projected images of the object grid that overlay at the detector. For a 160 kVp spectrum and a 1 mm source spot size, adding a source grid with 50% duty cycle and a period of 4.7 lines per mm increased the visibility of a 9 lines per mm object grid placed 1 m downstream of the source and 1 m upstream of the detector by approximately 4×. This approach allows the use of a larger spot size and therefore higher flux.

Referring to FIG. 10, a composite image of a small bag (8"×9"), taken at 160 kV using a large spot size and a source grid to improve object grid visibility is shown according to embodiments described herein. The image was acquired using a system comprising a polychromatic source (e.g., Comet x-ray tube) run with a 1 mm spot size, a 103 LPI source grid, 210 LPI object grid, and 103 LPI detector grid oriented perpendicular to the other two for beam hardening corrections, used with the CMOS detector. The image on the left is an attenuation image. The image on the right is an attenuation image with scatter overlay (color). Propellants present in the bag show scatter, as do business cards, a watch band, and tic tac candies. Chapstick next to the model rocket engine looks similar by shape, but does not exhibit scatter.

In order to characterize the performance and verify consistency of an imaging system, particularly the ability to detect texture, a set of calibration standards was developed. The first type of calibration standard comprises a scatter test object and provides a stable and repeatable means for measuring scatter signal across different systems. The inventors determined that the scatter test object, which was stable and robust with well characterized small-scale structure, was beneficial so that the efficacy of different x-ray systems could be tested. The scatter test object can have sufficient contrast for use at high energies, when the cross section for elastic scatter is relatively small. One embodiment of the scatter test object calibration standard comprises a block of polymer with microparticles or nanoparticles dispersed evenly within it. The particles can comprise metal and/or metal oxide. The particles have a known size distribution. The polymer block can be fabricated with a series of steps or geometric features of different thickness. The resulting object provides a measure of x-ray scattering as a function of thickness, over a wide range of imaging systems and x-ray energies, and which is stable and robust. The testing and calibration can be particularly advantageous for certain applications including explosives detection and medical imaging. In such applications, the scatter test object can comprise a scatter-imaging phantom. The phantom is an object having the same scatter qualities and/or properties as a material in which one is interested in imaging.

In some embodiments, metal or metal oxide microparticles or nanoparticles were fixed in a polymer. Particles with a well-defined size distribution are commercially available. This is important because the scatter signal exhibits sensitivity to the size of the particles or texture. A polymer (e.g., epoxy) is robust and stable over time and adds no additional scatter signal. The metal or metal oxides have a sufficiently high density that the x-ray refractive index change between the particles and the polymer produce a strong scattering signal. After testing numerous metal and metal oxide nanoparticles and microparticles, ZnO was found to disperse evenly in epoxy, and scatter step-wedges were created out of 20 vol % ZnO particles fixed in epoxy. Blocks were created with 1 µm particles, and with a distribution of particles 5 µm and below; steps were cut to be approximately 6 mm thick with a maximum thickness of 25 mm. The scatter step wedges are shown in FIG. 11A, along with scatter images (see FIG. 11B) at two different energies. When transitioning between different gratings-based systems, or different energies, contrast-to-noise was measured on the step wedges and compared. The scatter test object calibration standard is not limited to a step wedge shape. A wedge with graded thickness is an example of an alternative shape. Further still, the scatter test object can comprise one or more shapes having a constant thickness. A plurality of constant thickness calibration standards, each with different thickness, different particle loadings, and/or particle sizes can be used as an alternative.

Another type of calibration standard comprises a beam hardening test object for phase contrast x-ray imaging, which can be used to test for beam hardening artifacts that can adversely affect the scatter measurement and ensure the artifacts have been properly removed. The use of the beam hardening test object calibration standard relies on the fact that it does not have density fluctuations at length scales to which the measurement is sensitive—that the materials in the calibration standard are homogeneous. This provides a baseline expectation that data taken with the test device will, if properly corrected for beam hardening, indicate no additional fringe visibility loss due to texture. For many applications, a beam hardening correction will be applied for multiple materials, spanning much of the periodic table, and for materials with a wide range of attenuation values. The calibration standard is designed to contain multiple homogeneous materials across a range of atomic number, with the thickness of each material selected so that a moderate amount of attenuation (10% to 90% of the original beam) is present.

One embodiment of the beam hardening test object calibration standard can comprise three or more materials that are each homogeneous, with no large density variations on length scales between 10 nm and 200 microns, and represent a range of atomic numbers. The materials are machined to a thickness suited to the energy of the x-rays used, such that 10-90% of the beam intensity is transmitted through the object. A corrected phase contrast measurement, as described elsewhere herein, is performed with corrections for spurious signals due to spectral changes during attenuation, and the resulting scatter image of the calibration standard will be consistent with background if the correction is successful.

In some embodiments, beam hardening test object comprises approximately one mean free path at 160 kV of aluminum (28 mm), stainless steel (7 mm), copper (5.5 mm), and tin (1.0 mm). This gave a range of Z, and substantial attenuation, over which to test the beam hardening correction. The beam hardening correction can correct partially the visibility reduction observed in the calibration standard materials, in contrast with the complete correction observed with the 12.5 mm Al sample. This appears to be related to the relatively high attenuation of the calibration standard. Known homogeneous material samples (such as water) show a corrected scatter value consistent with homogeneity. Accordingly, there is no issue with the calibration standard significantly impacting the measurements of the explosive and benign materials.

Figure 12:
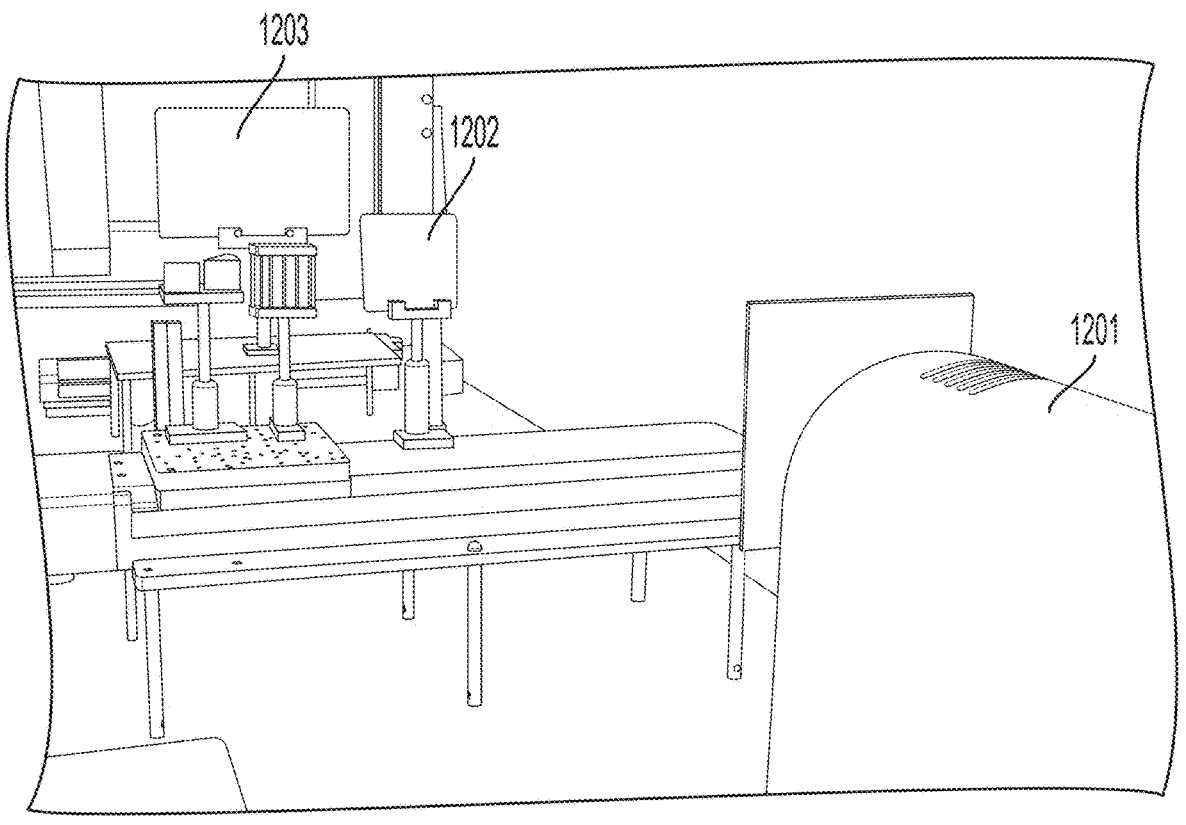
FIG. 12 is a photo of an embodiment of a system described herein (absent a source grid). An X-ray tube is at lower right and the beam direction is from lower right to upper left. Filter materials are immediately in front of the x-ray tube; the standard test objects can be seen halfway down the table at upper left; the object and detector grids are also visible in the upper left quadrant. The detector is obscured by the detector grid.

Measurements of a variety of materials, including threat and non-threat materials, were conducted in collaboration with Chuck Divin, Sabrina De Piero, Larry McMichael, and Harry Martz at Lawrence Livermore National Laboratory. These measurements were performed using a microfocus x-ray tube (Hamamatsu L12161-07). The nominal spot size at max current was 50 µm. The final measurement configuration is shown in FIG. 12 and consisted of the Hamamatsu microfocus tube 1201 operated at 0.5 mA current and 50 µm spot size, an object grid 1202 with 285 LPI (JPI Healthcare), and a detector grid 1203 with 120 LPI (Kiran Medical). Measurement time was necessarily very long—10 minutes, or 300 mA·s. This was selected and verified to be well above the range where noise in the images is dominated by counting statistics, in order to emphasize the physical signatures. The small spot size provided by the microfocus tube necessitated longer measurement times. In some embodiments, high-energy, large spot size measurements described herein have measurement times that are less than 10 minutes, 8 minutes, 6 minutes, 5 minutes, 3 minutes, 2 minutes, 1 minute, or 30 seconds.

Figure 13:
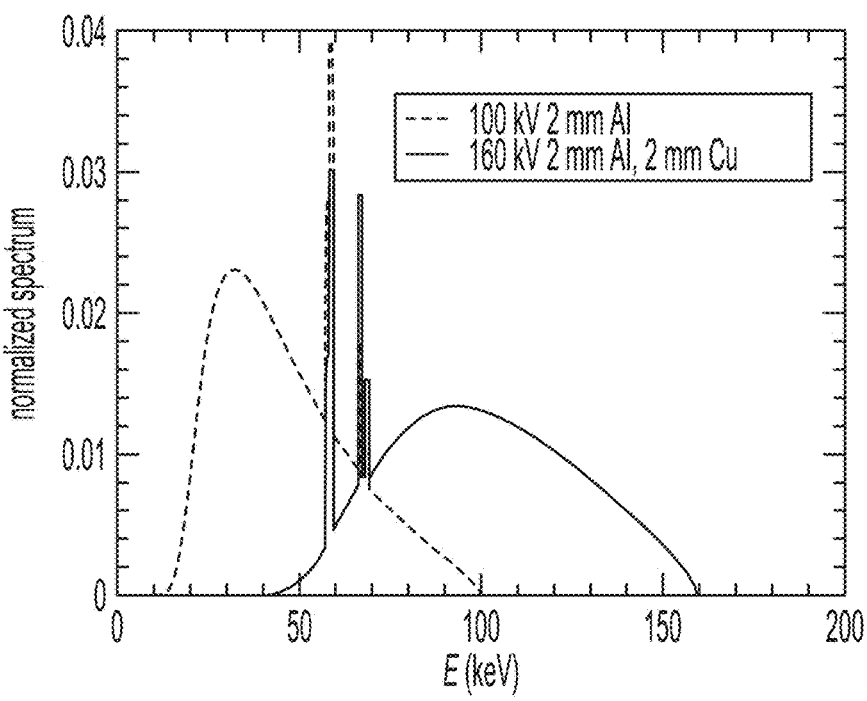
FIG. 13 is a graph showing calculated beam spectra at "high" energy and "low" energy.

Data was acquired for two different spectra, chosen to be similar to spectra used for dual-energy measurements in current checkpoint screening. Calculated spectra are shown in FIG. 13. The high energy spectrum, in blue, had an endpoint energy of 160 kV (but was reduced to 150 kV with the Hamamatsu source), 2 mm of copper and 2 mm of aluminum filtration. The average correlation length for this system, with the 285 LPI grid, was 90 nm. The low energy spectrum, shown in red, had an endpoint energy of 100 kV, 2 mm aluminum filtration, and an average correlation length of 170 nm.

Figure 14:
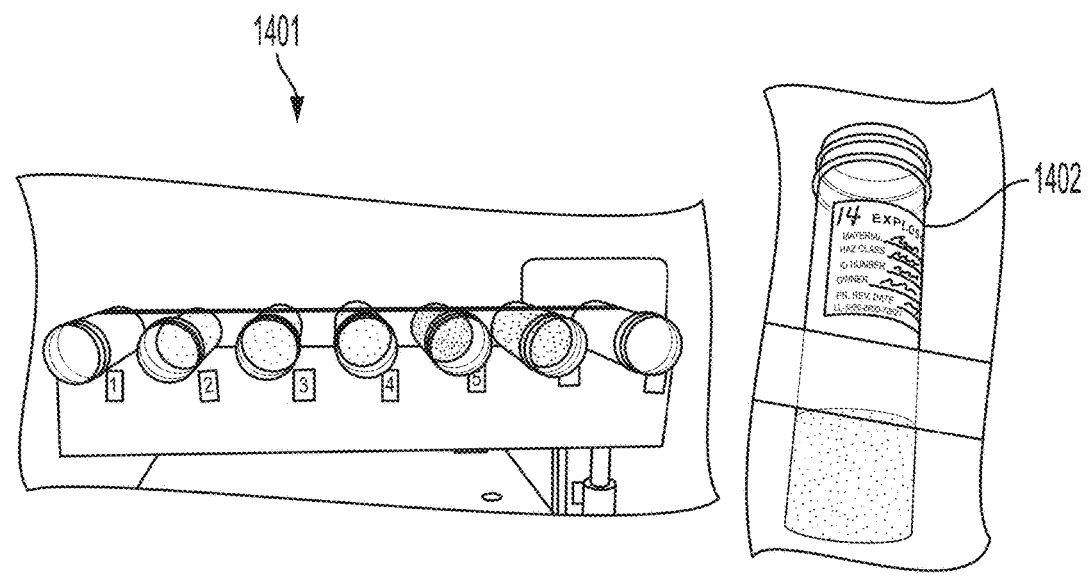
FIG. 14 shows a set of vials containing samples set for end-on imaging and a single vial containing explosive material.

The test dataset consisted of over 20 different benign materials, selected with knowledge of items typically found in baggage, and with a wide range of densities, effective atomic numbers, and including several items which were powdery or had other density variations. Four threat materials were selected, all with some level of mesoscale texture. Three of the materials were powders, with a range of grain sizes and preparation methods, and one was a moldable. Materials were placed in plastic cylinders 3 cm in diameter and 2-3 cm thick, had a total mass of 15-30 g per sample, and were imaged end-on to produce a large area with uniform thickness. An example vial 1402 and set of samples 1401 assembled for imaging are shown in FIG. 14.

implicitly weighted averages over all energies present in the spectrum. The variations observed in both absorption and scatter images were propagated as errors to obtain variation estimates for both quantities. This was performed for both the high and low energy spectra, and the quantitative results are shown in Table I: attenuation coefficient $\mu$ at low and high energy, and scatter coefficient $\nu$ at low and high energy, for each sample measured.

Figure 15:
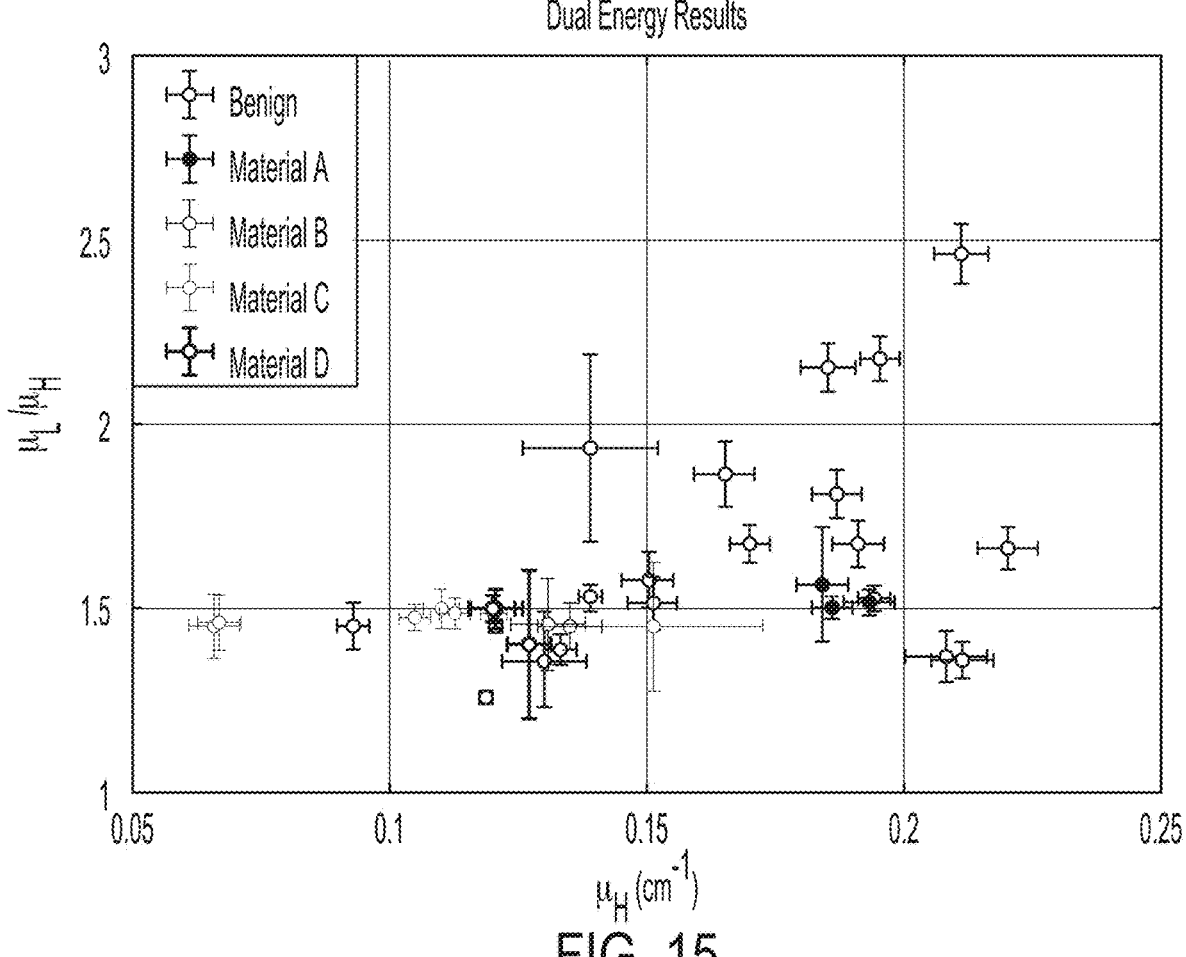
FIG. 15 is a graph showing Dual Energy Results. The y-axis indicates $\mu_L/\mu_H$, which can be related to $Z_{eff}$, and the x-axis is $\mu_H$, which can be related to density. Materials A-D represent four different explosive materials and encompass a number of preparations.

The attenuation coefficients extracted from the phase contrast measurements can be interpreted in the same manner as conventional dual energy measurements, which are analyzed to estimate effective atomic number $Z_{eff}$ and density $\rho$. Here, we examined the ratio of the low energy and high energy attenuation coefficients ($\mu_L/\mu_H$); for a fully calibrated system this quantity can be related to the effective atomic number $Z_{eff}$. In FIG. 15 we plot $\mu_L/\mu_H$ as a function of $\mu_H$, which can be mapped approximately to density. Error bars indicate the variation observed within each sample.

TABLE 1

| Material | $\mu_H$ (cm$^{-1}$) | $\mu_L$ (cm$^{-1}$) | $\mu_L/\mu_H$ | $\nu_H$ (cm$^{-1}$) | $\nu_L$ (cm$^{-1}$) |
|---|---|---|---|---|---|
| raspberry jelly | 0.208 ± 0.008 | 0.285 ± 0.010 | 1.37 | −2.00E−03 ± 1.38E−02 | −2.25E−03 ± 2.49E−03 |
| strawberry jelly | 0.211 ± 0.006 | 0.287 ± 0.007 | 1.36 | −4.44E−05 ± 1.33E−02 | −9.30E−04 ± 2.45E−03 |
| coconut oil | 0.170 ± 0.004 | 0.285 ± 0.005 | 4.67 | 9.20E−05 ± 1.19E−02 | −1.32E−03 ± 2.64E−03 |
| rubber cement | 0.119 ± 0.001 | 0.150 ± 0.001 | 1.27 | −1.86E−04 ± 1.13E−02 | 2.83E−04 ± 2.02E−03 |
| Vaseline | 0.130 ± 0.008 | 0.177 ± 0.013 | 1.36 | 5.21E−04 ± 5.81E−03 | 2.97E−04 ± 2.53E−03 |
| Colgate | 0.191 ± 0.005 | 0.320 ± 0.008 | 1.67 | 3.63E−03 ± 6.45E−03 | 1.46E−02 ± 3.08E−03 |
| Olay sunscreen | 0.165 ± 0.006 | 0.308 ± 0.010 | 1.87 | 9.21E−03 ± 6.44E−03 | 3.33E−02 ± 3.16E−03 |
| pure honey | 0.194 ± 0.003 | 0.297 ± 0.004 | 1.54 | −5.31E−04 ± 6.88E−03 | −9.83E−04 ± 2.60E−03 |
| apricot scrub | 0.150 ± 0.005 | 0.237 ± 0.008 | 1.58 | 2.69E−04 ± 7.31E−03 | 4.84E−03 ± 3.37E−03 |
| kids sunscreen | 0.211 ± 0.005 | 0.520 ± 0.011 | 2.47 | 5.66E−02 ± 1.01E−02 | 1.70E−01 ± 9.20E−03 |
| Old Spice antiperspirant | 0.195 ± 0.004 | 0.425 ± 0.008 | 2.18 | 5.10E−03 ± 7.32E−03 | 1.62E−02 ± 4.40E−03 |
| Mitchum deodorant | 0.187 ± 0.005 | 0.339 ± 0.008 | 1.82 | 2.47E−03 ± 6.72E−03 | 7.62E−03 ± 2.98E−03 |
| Banana sunscreen | 0.151 ± 0.005 | 0.229 ± 0.008 | 1.52 | −1.60E−03 ± 6.28E−03 | −7.49E−03 ± 2.30E−03 |
| Banana kids sunscreen | 0.185 ± 0.005 | 0.399 ± 0.006 | 2.15 | 1.95E−02 ± 6.82E−03 | 6.47E−02 ± 4.34E−03 |
| AW toothpaste | 0.220 ± 0.006 | 0.366 ± 0.008 | 1.67 | 4.27E−03 ± 7.17E−03 | 3.12E−02 ± 4.77E−03 |
| sunflower oil | 0.133 ± 0.003 | 0.185 ± 0.003 | 1.39 | 2.44E−04 ± 5.76E−03 | 5.11E−04 ± 3.06E−03 |
| Nutella | 0.139 ± 0.013 | 0.269 ± 0.025 | 1.94 | 3.55E−03 ± 5.90E−03 | 4.01E−02 ± 4.92E−03 |
| water | 0.139 ± 0.002 | 0.213 ± 0.004 | 1.53 | 6.36E−05 ± 5.77E−03 | −1.08E−03 ± 2.08E−03 |
| flour | 0.121 ± 0.001 | 0.176 ± 0.002 | 1.46 | 6.74E−03 ± 6.55E−03 | 7.03E−02 ± 7.07E−03 |
| powdered sugar | 0.093 ± 0.003 | 0.135 ± 0.004 | 1.45 | 1.44E−02 ± 5.84E−03 | 1.28E−01 ± 5.23E−03 |
| Material A_6 | 0.184 ± 0.018 | 0.289 ± 0.005 | 1.57 | 2.59E−03 ± 6.57E−03 | 3.05E−02 ± 4.01E−03 |
| Material A_7 | 0.186 ± 0.003 | 0.280 ± 0.004 | 1.51 | 4.02E−03 ± 5.64E−03 | 2.92E−02 ± 3.79E−03 |
| Material A_5 | 0.193 ± 0.003 | 0.293 ± 0.005 | 1.52 | 3.84E−03 ± 6.18E−03 | 3.14E−02 ± 3.98E−03 |
| Material B_9 | 0.131 ± 0.010 | 0.191 ± 0.007 | 1.46 | 1.05E−03 ± 7.08E−03 | 2.44E−02 ± 7.07E−03 |
| Material B_121-1A | 0.135 ± 0.004 | 0.196 ± 0.006 | 1.45 | −5.38E−04 ± 6.02E−03 | 2.94E−02 ± 7.36E−03 |
| Material C_11 | 0.113 ± 0.002 | 0.169 ± 0.003 | 1.50 | 1.73E−02 ± 6.54E−03 | 1.15E−01 ± 7.03E−03 |
| Material C_14 | 0.067 ± 0.002 | 0.098 ± 0.004 | 1.46 | 1.62E−02 ± 4.80E−03 | 1.19E−01 ± 4.94E−03 |
| Material C_13 | 0.066 ± 0.002 | 0.096 ± 0.005 | 1.45 | 1.30E−02 ± 5.03E−03 | 1.16E−01 ± 5.52E−03 |
| Material C_10 | 0.110 ± 0.002 | 0.165 ± 0.005 | 1.50 | 1.36E−02 ± 8.81E−03 | 1.15E−01 ± 7.96E−03 |
| Material C_12 | 0.113 ± 0.002 | 0.167 ± 0.003 | 1.49 | 1.49E−02 ± 5.80E−03 | 1.14E−01± 7.25E−03 |
| Material C_18 | 0.105 ± 0.001 | 0.155 ± 0.003 | 1.48 | 3.19E−03 ± 8.05E−03 | 3.92E−02 ± 1.17E−02 |
| Material C_19A | 0.119 ± 0.001 | 0.177 ± 0.001 | 1.49 | 1.77E−02 ± 1.03E−02 | 1.52E−01 ± 8.06E−03 |
| Material C_7A | 0.151 ± 0.011 | 0.219 ± 0.021 | 1.45 | 9.33E−04 ± 7.80E−03 | 3.66E−03 ± 7.30E−03 |
| Material D_2 | 0.127 ± 0.018 | 0.178 ± 0.004 | 1.41 | 1.35E−03 ± 6.99E−03 | 1.91E−02 ± 9.51E−03 |
| Material D_1 | 0.120 ± 0.002 | 0.179 ± 0.004 | 1.49 | 1.89E−03 ± 6.70E−03 | 2.05E−02 ± 1.04E−02 |
| Material D_4 | 0.120 ± 0.003 | 0.180 ± 0.005 | 1.51 | 1.95E−03 ± 6.53E−03 | 1.59E−02 ± 9.95E−03 |
| Material D_3 | 0.121 ± 0.003 | 0.182 ± 0.005 | 1.51 | 1.39E−03 ± 6.70E−03 | 1.90E−02 ± 1.00E−02 |

Once data were acquired, the absorption/refraction/scatter images were extracted and the scatter image corrected for beam hardening. A region of interest was chosen, typically including most of the material, and mean and standard deviation values were extracted for both attenuation (I/I$_0$) and scatter (V/V$_0$). The attenuation was converted into an attenuation coefficient $\mu=-\ln(I/I_0)/t$, where t represents measured sample thickness, and $\mu$ is in units of mean free attenuation paths per cm (cm$^{-1}$). In analogous fashion, we extracted a scatter coefficient $\nu=-\ln(V/V_0)/t$, in units of mean free scatter paths per cm (cm$^{-1}$). Both quantities are Benign materials were shown in black. Water was indicated at $\mu_H=0.139$ and $\mu_L/\mu_H=1.53$; a number of other benign materials had $Z_{eff}$ similar to water, but at higher densities many of the benign materials also exhibited higher $Z_{eff}$. Threat materials were labeled by letters; with each letter signifying a single material, but samples within each group may have different preparation conditions. Material A showed a $Z_{eff}$ similar to water but the density is significantly larger. Materials B and D were close to water in density and $Z_{eff}$, although slightly lower in both. Material C exhibited a wide range of densities corresponding to different preparation conditions, but $Z_{eff}$ still close to that of water. In all four material categories, at least some of the samples exhibited density/$Z_{eff}$ which were consistent with benign materials.

Figure 16:
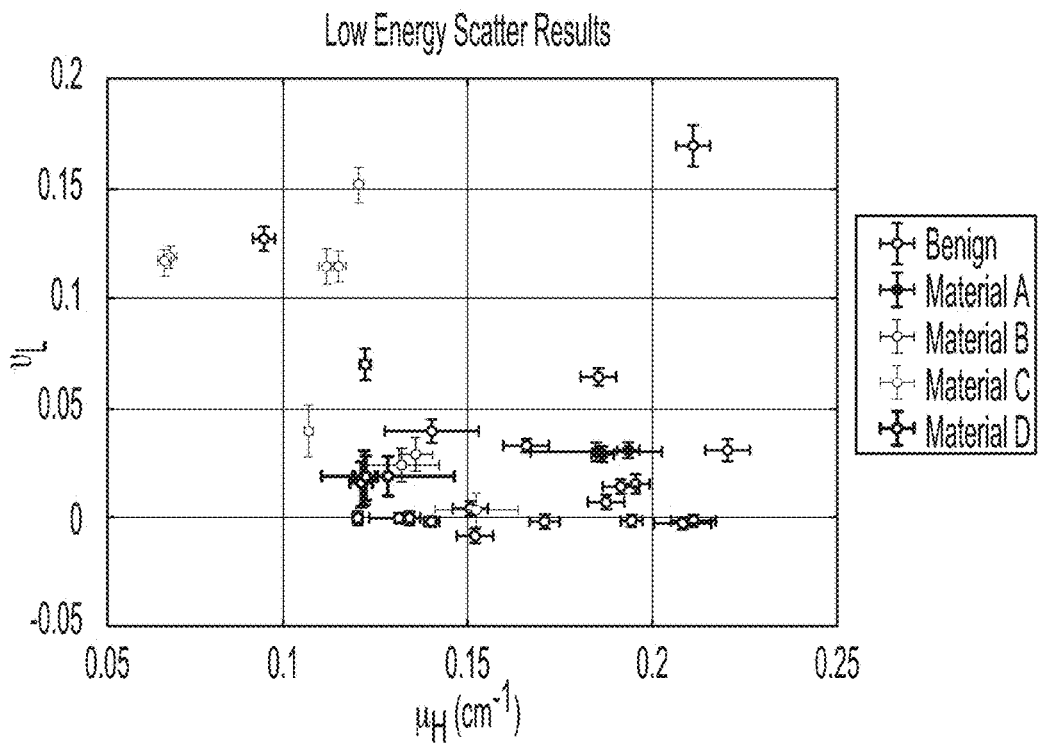
FIG. 16 is a graph showing scatter coefficient at low energy $v_L$ as a function of $\mu_H$ (proportional to density). Explosives are labeled by letters A-D.

Next, we examined material properties revealed by scatter, plotting the scatter coefficient for the lower energy spectrum, $v_L$, as a function of density (approximated as $\mu_H$), shown in FIG. 16. Note that a scatter coefficient of zero indicates no scatter was detected from a given material. The first qualitative observation we can make is that this plot is distinct from the dual energy information, with the distribution of properties clearly different than the previous plot, indicating that unique information is being displayed. For Materials A, B, and D, a small but significant amount of scattering is present. Note that in most cases, this distinguishes them from materials with otherwise similar density and atomic number. Material C covers not only a wide range of densities, but also a wide range of textures, from apparently homogeneous to very highly scattering, depending on the preparation method used.

The range of scatter values in the benign materials can be helpful for discrimination as well. At low density, powdered sugar ($\mu_H$=0.093, $v_L$=0.13) exhibits very high scattering; flour is also fairly highly scattering ($\mu_H$=0.12, $v_L$=0.07). Nutella® exhibits a moderate amount of scattering ($\mu_H$=0.14, $v_L$=0.04). There were four different types of sunscreen, which illustrate an interesting range of scattering properties. One of the sunscreens, Banana Boat® ($\mu_H$=0.15, $v_L$=−0.007), is an organic sunscreen and contains no metals; it is relatively low in density and no significant scatter is observed. Olay® sunscreen ($\mu_H$=0.17, $v_L$=0.033) contains 3% ZnO particles and exhibits some scatter. Banana Boat Kids® contains 6% $TiO_2$ and 4% ZnO and shows higher scatter yet ($\mu_H$=0.19, $v_L$=0.065). The final sunscreen (Badger® brand kids sunscreen) shows high $Z_{eff}$, high density, and high scatter ($\mu_H$=0.21, $v_L$=0.17); it includes 19% ZnO particles, nearly as high of a concentration as our scatter step wedges. Other materials which show a small amount of scatter include deodorants and toothpaste, as can be seen in Table I. Note that materials which are homogeneous, such as water, sunflower oil, honey, and Vaseline®, display scatter values consistent with zero, confirming that the beam hardening correction process is successfully accounting for fringe visibility changes associated with spectral changes.

Figure 17:
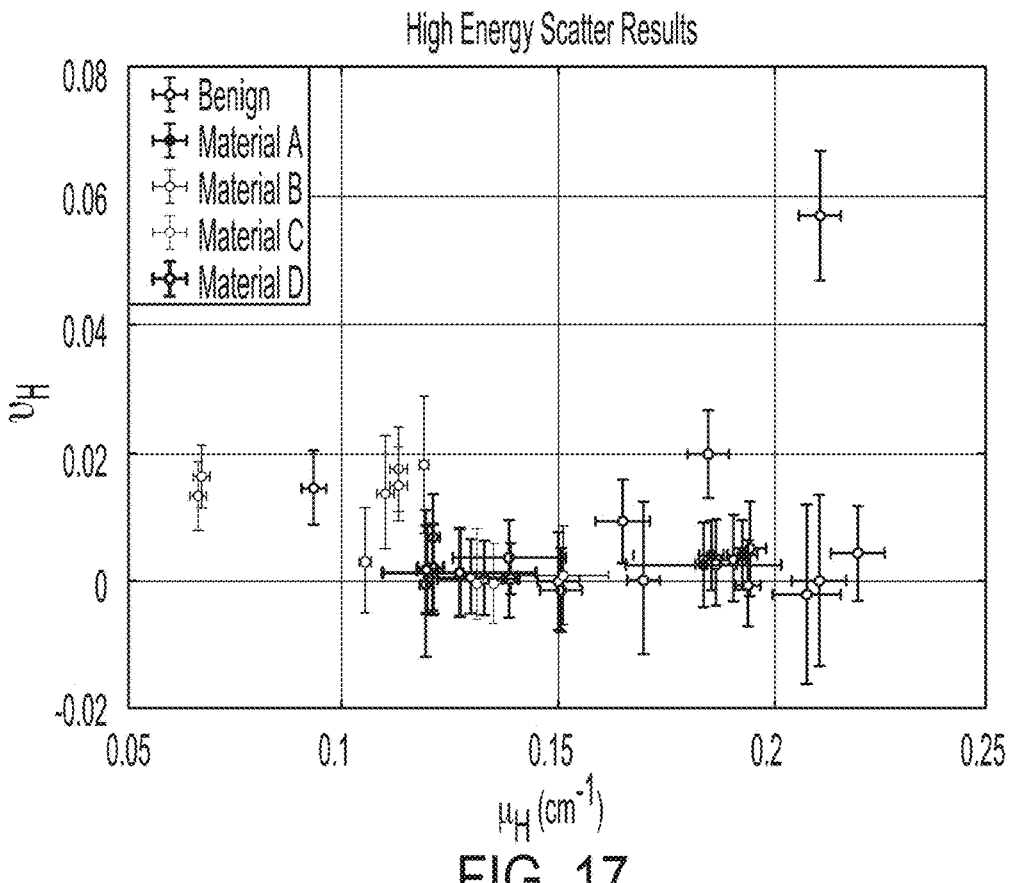
FIG. 17 is a graph showing scatter coefficient at high energy $v_H$ as a function of $\mu_H$ (proportional to density). Explosives are labeled by letters A-D.

For the higher energy spectrum, the absolute values of all the scatter coefficients are reduced, as shown in FIG. 17. Several of the more weakly scattering samples cannot be distinguished from non-scattering materials, but the more strongly scattering materials are still distinguishable. Detailed numerical results can be seen in Table I.

Figure 18A:
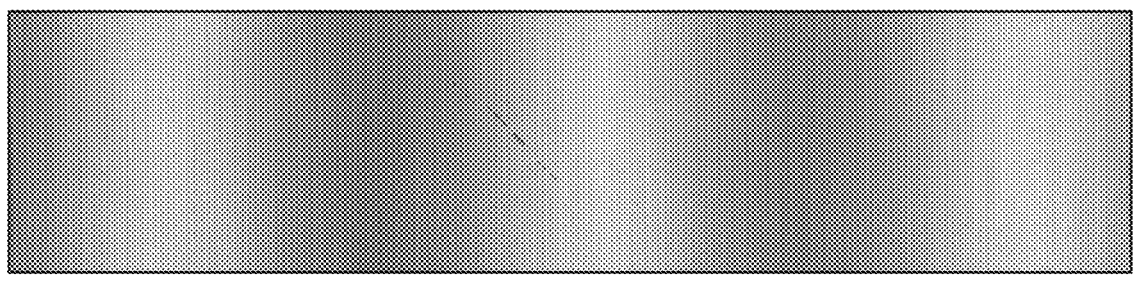
FIGS. 18A and 18B are (18A) close-up of a region of the grating image, showing the vertical grating lines and the longer period Moire pattern. Near the center is a line of bad pixels from a scratch on the detector and (18B) close up of a grating image with both the object and detector gratings, in a section of bad pixels.
Figure 18B:
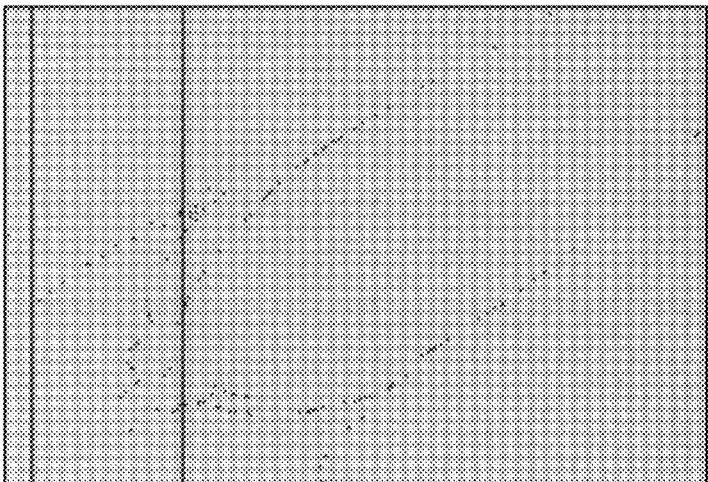

Often, not all pixels on the detector will record x-rays. Scratches or other damage can leave patterns of dead pixels. If not corrected, or if corrected using linear interpolation which is typically used for x-ray imaging, this can introduce artifacts into the reconstructed scatter and phase contrast images. The grating is typically aligned with the detector array, producing a pattern of vertical stripes. The grating period is typically chosen so that its period on the image is a few pixels. The image may show vertical intensity oscillations with a longer period, which might be a Moire pattern between the grating shadows and the pixel boundaries. The value of any given pixel (x, y) of the grating image will be designated g(x, y), and the image size will be $N_x \times N_y$ pixels. FIG. 18A includes an image of a region of the grating image, showing the vertical grating lines and the longer period Moire pattern. Near the center is a line of bad pixels from a scratch on the detector. FIG. 18B is a grating image with both the object and detector gratings in a section of bad pixels.

Figure 19A:
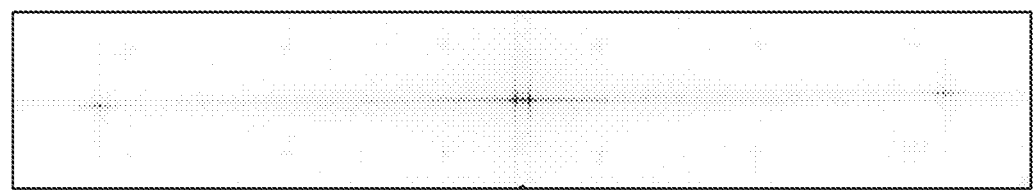
FIGS. 19A-19C are regions of a Fourier transform of a grating image.
Figure 19B:
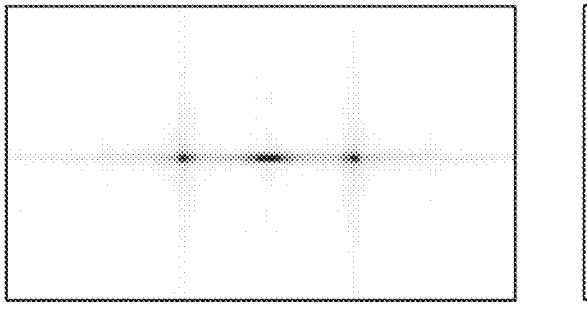
Figure 19C:
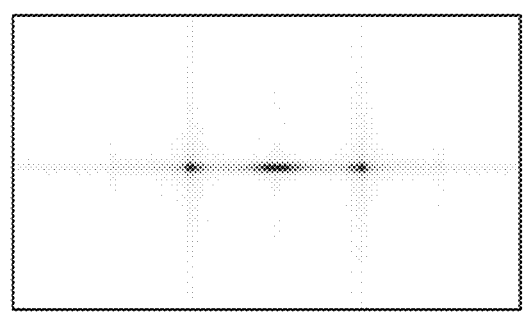

FIGS. 19A-19C include Fourier transforms of grating images. In FIG. 19A, a section of the Fourier transform of the grating image shows the central peak at (0, 0) and the first order harmonic peaks on either side at (±613, ±9). The non-zero y values of the first harmonic peak indicate that the grating was not perfectly aligned with the detector in this image. In FIG. 19B, a close-up of a region of the center of the Fourier Transform of the grating image shows the central peak at (0, 0) and Moire peaks at (±10, 0). In FIG. 19C, a close-up of the region around the first harmonic shows the harmonic peak at (613, −9) and convolutional Moire peaks at (603, −9) and (623, −9).

The Fourier transform of the grating image shows peaks at the origin and near the x-axis representing the Moire period, the grating period, and at intervals of the Moire period on either side of the grating period. If the grating period is long enough, higher harmonics of the grating will show up although typically the grating spacing and placement are chosen so that only the first harmonic appears. If a detector grid is present, peaks will be present at the detector grid period and its harmonics, as well as cross-harmonics between the detector and object grid. The grating Fourier transform will be denoted G(x, y).

After subtracting the dark image, bad pixels typically have values near zero. The grating image, despite its features, is usually relatively low contrast. A simple threshold cut-off on the grating image is usually effective for selecting pixels to fix.

The bad pixel detection can be made even better by reducing major sources of large period variation within the grating image. A copy G'(x, y) is made of the Fourier transform of the grating image, and the regions around the central peak and the grating harmonic peak pairs are removed, making sure to include the Moire satellites around the major peaks. Let $p_M$ be the Moire period in the grating image, $(p_{ox}, p_{oy})$ be the location of the first harmonic peak of the object grid, and $(p_{dx}, p_{dy})$ be the first harmonic peak of the detector grid. An acceptable filter is to choose $r_1$=2 $p_M$ and $r_2$=10 $p_M$, and then use:

$$r(x, y) = \sqrt{x^2 + y^2} \tag{1}$$

$$F(x, y) = \begin{cases} 1 & r(x, y) > r_2 \\ 0 & r(x, y) > r_1 \\ \frac{1}{2}[1 - \cos(\pi(r(x, y) - r_1)/(r_2 - r_1))] & \text{otherwise} \end{cases} \tag{2}$$

$$G'(x, y) = G(x, y) \prod_{j=-n_o}^{n_o} \prod_{k=-n_d}^{n_d} F(x + jp_{ox} + kp_{dz}, y + jp_{oy} + kp_{dy}) \tag{3}$$

where $n_o$ is the number of harmonic peaks of the object grid and $n_d$ is the number of harmonic peaks of the detector grid.

This is then Fourier transformed back to give the image $g_0$ (x, y). The bad pixels, being isolated aperiodic features, are composed primarily of high frequency components so the inverse Fourier transform preserves these structures. Since the zero-period component has been removed, the average value of the image will be zero. With most structure removed, almost all pixels will have values near zero while the dead pixels will have highly negative values. All pixels with values lower than a threshold value will be considered bad and removed. A reasonable threshold is −G(0, 0)/3.

Figure 20:
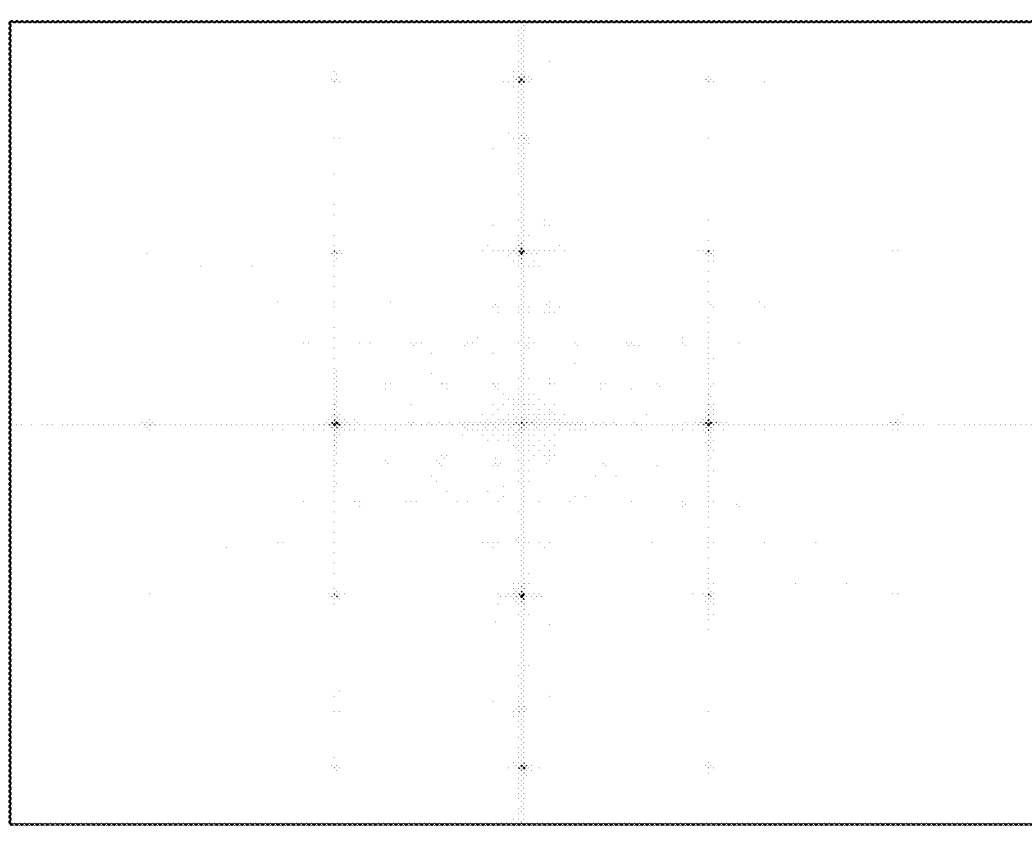
FIG. 20 is a Fourier transform of a grating image with both an object and detector grid, showing first and second harmonics as well as cross-harmonics.

Because Fourier analysis based on convolutional patterns around the harmonic peaks are used for producing the scatter and phase contrast images, simply replacing a bad pixel by the average of its neighbors is insufficient. This neglects the short scale variation on the order of the grid pattern that is crucial to the analysis. Instead, we will use the idea that in the vicinity of any pixel out to a radius of a few pixels, the pixel values can be approximated by contributions from all harmonic and cross-harmonic peaks from the gratings. FIG. 20 includes a Fourier transform of a grating image with both an object and detector grid, showing first and second harmonics as well as cross-harmonics.

$$g(x,y) \approx \sum_{j=-n_o}^{n_o} \sum_{k=-n_d}^{n_d} b_{(jk)} e^{2\pi i \left( (jp_{ox}+kp_{dx})x/N_x + (jp_{oy}+kp_{dy})y/N_y \right)}. \tag{4}$$

The $b_{(jk)}$ are complex fitting parameters. Because $g(x,y)$ is real, $b_{(00)}$ must be real and $b_{(-j-k)}=b^*_{(jk)}$. However, there is no need to include these constraints in the algorithm, since unconstrained linear least squares fitting via singular value decomposition (SVD) is robust, simple, and reliable. Since this fit extends to several pixels around the bad pixel, detailed features within this region can be washed out for the fit. However, the image analysis technique involves a low-pass filter so that these details will be lost anyway. Despite the matrix-like terminology, conceptually in the fitting process b is a vector and the pair (jk) is treated as a single index. This can be accomplished with a mapping of (jk) to an index 1 running from 0 to 1 max=$(1+2n_o)(1+2n_d)$.

Choose a starting fitting step $r_f$ as the number of pixels in x and y to either side of the bad pixel to include in the fit. This should be chosen so that $1+2r_f$ at least covers one grating period. In addition, if entire columns of bad pixels are expected, it should be at least 2 to avoid ill-conditioned fits. For any given bad pixel at $(x_b, y_b)$, scan over all pixels $(x, y)$ such that $x_b-r_f \leq x \leq x_b+r_f$ and $y_b-r_f \leq y \leq y_b+r_f$. If the $n^{th}$ scanned pixel (starting from n=0) is not bad, add its value $g(x_n, y_n)$ to the vector h of nearby good pixel value $$h_i = g(x_n, y_n) \tag{5}$$

and add a row to the matrix of fitting vectors A $$A_{i,l} = e^{2\pi i \left( (jp_{ox}+kp_{dx})x_n/N_x + (jp_{oy}+kp_{dy})y_n/N_y \right)}. \tag{6}$$

Let h have m elements, so that A is m×l max in size. If m<$l_{max}$, the fit will be ill-conditioned—there will be more fit variables $b_j$ than constraints $h_i$. Even m=l max is likely to lead to poor results. A reasonable criterion is to have the problem over-determined by a factor of 2. If m<6, increase $r_f$ by 1 and find h and A again; repeat until m≥2 $l_{max}$.

The problem is now a complex linear fit, h=A·b. This is solved by finding the SVD of A.

$$A = U \cdot W \cdot V$$

where V is a $l_{max} \times l_{max}$ unitary matrix, W is a $l_{max} \times l_{max}$ non-negative real diagonal matrix, and U is a m×$l_{max}$ matrix which is column orthonormal $$u_j \cdot u_k = \delta_{jk},$$

$u_j$ is the $j^{th}$ column of U, and the symbol · indicates the inner product. The elements on the diagonal of W are called the singular values. The condition number of A is the ratio of the largest to the smallest of the singular values. If the condition number of W is more than 10, increase $r_f$ by 1 and find h and A again.

Let $W^{-1}$ be the pseudo-inverse of W; a $l_{max} \times l_{max}$ diagonal matrix such that $$\tilde{W}^{-1}_{ii} = \begin{cases} 0 & \text{if } W_{ii} = 0 \\ 1/W_{ii} & \text{otherwise} \end{cases}$$

The fit vector is then found by $$b = V \cdot \tilde{W}^{-1} \cdot U^\dagger \cdot h.$$

(It is worth noting that since we demand the condition number is finite, all $W_{ii}$ will be non-zero so that $W^{-1}=W^{-1}$.) Finally, set $$g(x_b, y_b) = \sum_{l=0}^{l_{max}} b_{ie} 2\pi i \left( (jp_{ox}+kp_{dx})x_b/N_x + (jp_{oy}+kp_{dy})y_b/N_y \right)$$

Then repeat the procedure where h is filled with pixel values from the grating+object image, replacing the bad pixel in the grating+object image with the fitted value (A does not change between the grating and grating+object image, so it can be re-used and its SVD does not have to be re-computed).

If the grating absorption modulation is low compared to the average value of the image, the cross-harmonic peaks can be neglected. For images with a detector grid, a fairly long grating period (resulting in multiple harmonic peaks) in one or both grids, and many bad pixels, this can potentially result in significant time savings due to the $O(ml_{max}^2)$ scaling of SVD.

Figures 21A, 21B:
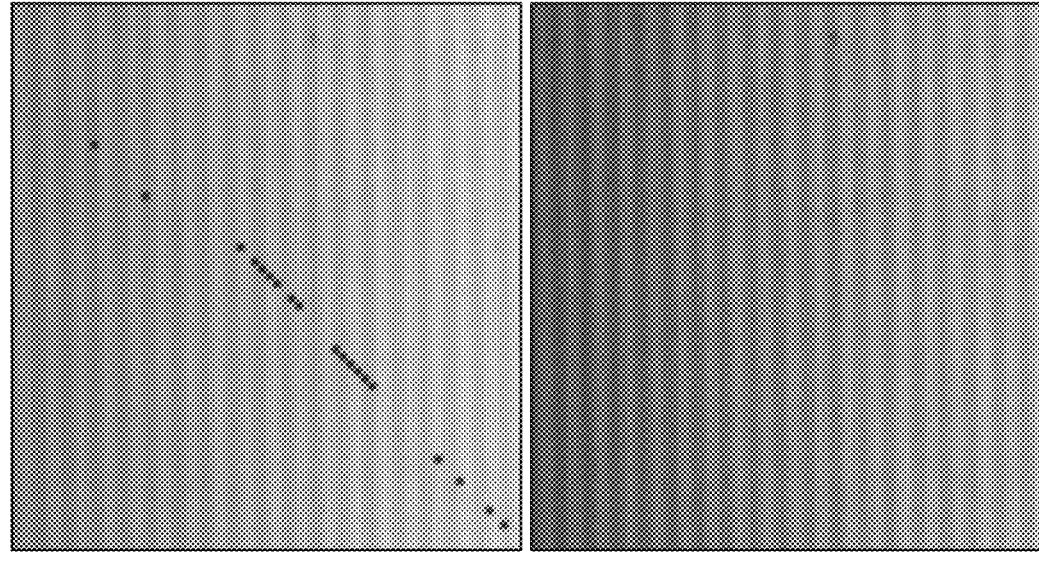
FIGS. 21A and 21B are images before and after bad pixel correction of a line of bad pixels, respectively.
Figures 22A, 22B:
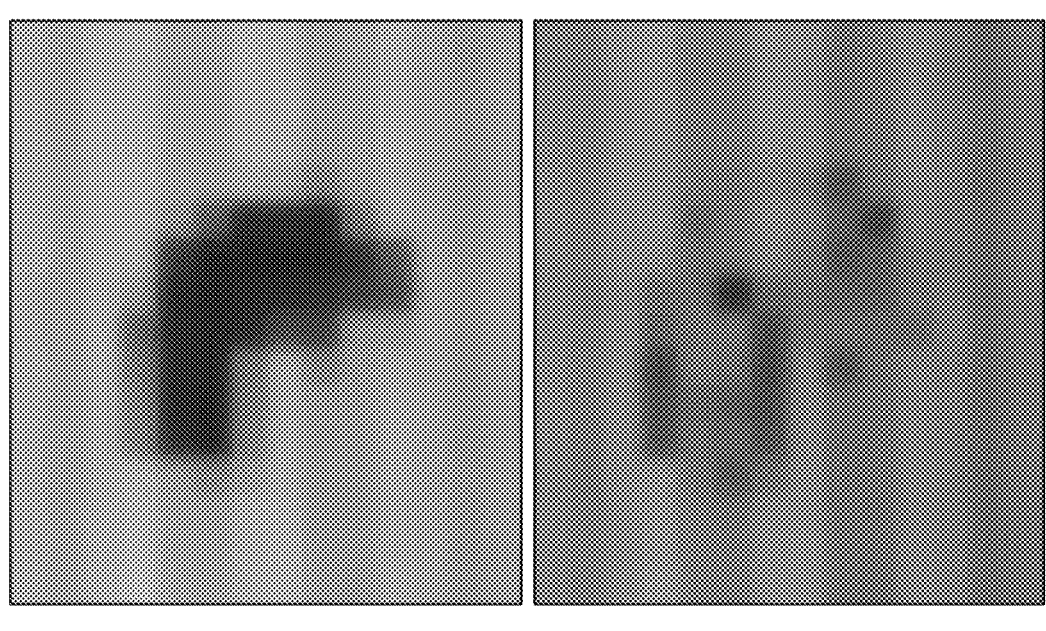
FIGS. 22A and 22B are images before and after bad pixel correction of a blob, respectively.
Figures 23A, 23B:
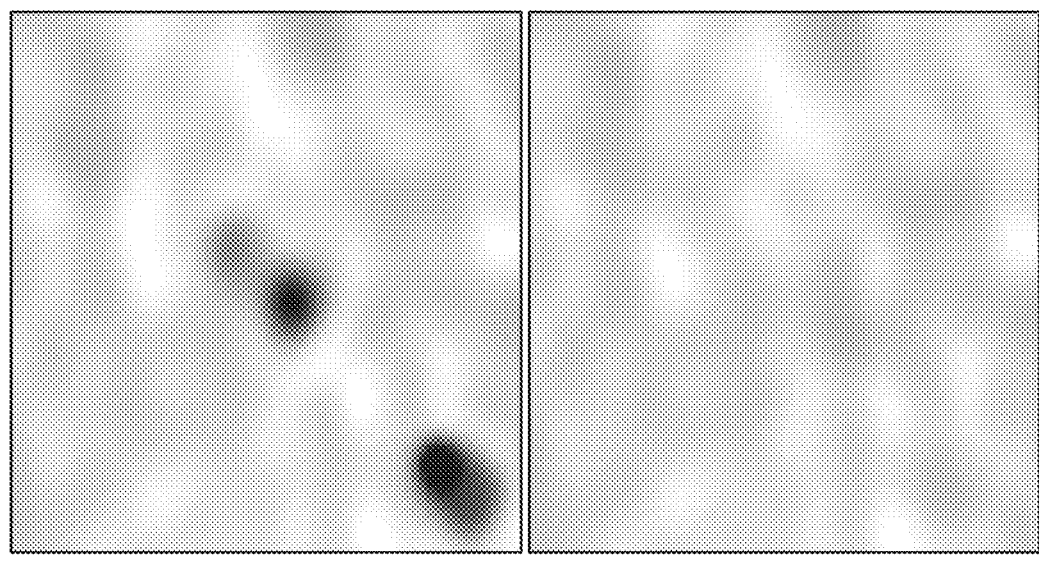
FIGS. 23A and 23B are images before and after bad pixel correction of a scatter image of a region illustrated in FIG. 21A.
Figures 24A, 24B:
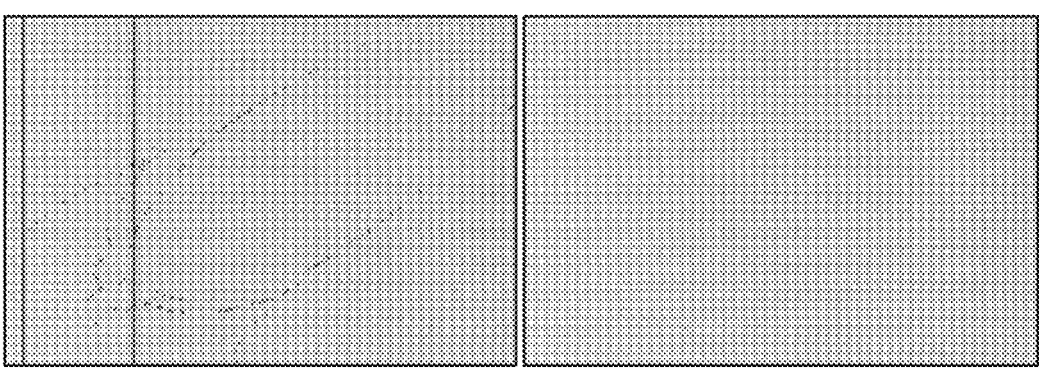
FIGS. 24A and 24B are images of a region of bad pixels with both a detector and an object grid, and with contributions from the second harmonic peaks of both grids before and after bad pixel correction, respectively.
Figure 25:
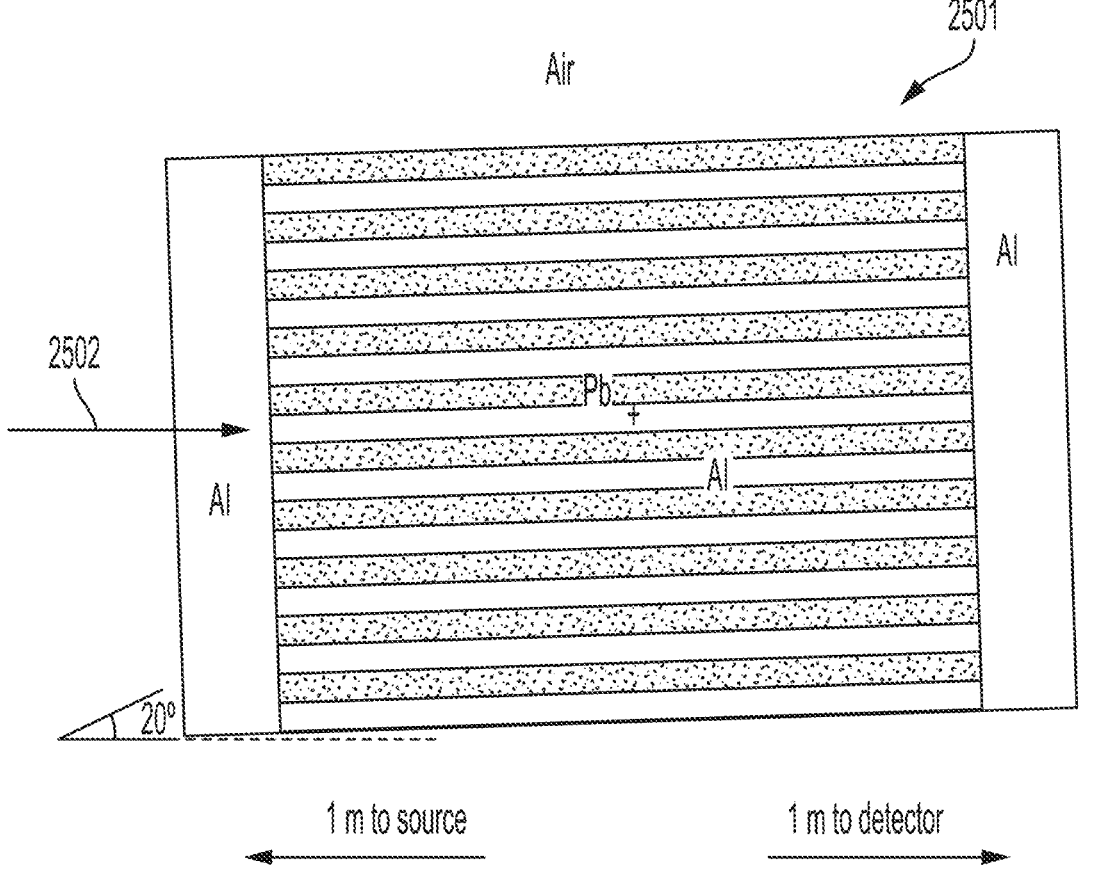
FIG. 25 is a schematic illustrating grid (i.e., grating) tilt. The beam direction is indicated by the arrow 2502.

FIGS. 21 and 22 give examples of the bad pixel detection (FIGS. 21A and 22A) and correction algorithm (FIGS. 21B and 22B). FIGS. 23 and 24 show how fixing bad pixels improves the reconstructed phase and scatter images (FIGS. 23A and 24A are before correction, FIGS. 23B and 24B are after correction), respectively. FIG. 25 is an example of bad pixel correction with both an object and detector grating and with contributions from multiple harmonics from both gratings (FIG. 25B is after bad pixel correction).

In some embodiments, the signal-to-noise ratio in the acquired data can be significantly improved by tilting the source grating, the object grating, the detector grating, or combinations thereof. Tilting can effectively make line sources narrower without the burden of physically manufacturing gratings with extremely narrow grating elements (i.e. parallel channels with high aspect ratios). Tilting can comprise rotating the gratings about an axis parallel to grating element lines. In certain embodiments wherein the grating elements are parallel channels (each channel having a width and a height), the amount of tilt is greater than zero degrees and less than or equal to a maximum angle equivalent to the arctangent of the width of the channel divided by the height.

Referring to FIG. 25, a schematic illustration depicts a grating 2501 having 210 parallel lines per inch and utilizing a 2 degree tilt relative to an incident beam 2502 from an x-ray source. Experimentally observed visibility changes with grid tilt were simulated and the simulation results are discussed herein. The geometry and materials of the measurement conditions were set up in a transport model to calculate the total flux at the detector for various grid tilt (i.e., rotation) angles. The flux in an array of 48 μm pixels is tallied with MCNP 6.1—a Monte Carlo transport code to determine the pixel-based amplitude to average flux ratio. While the physics of the SAXS signal induced by a test object is not included in the purely atomic number-atomic mass (ZAID) based cross section libraries, the no-object visibility (to undergo reduction from object scatter) can be computed. Ideally this quantity should be as large as is obtainable for the greatest sensitivity.

Figures 26A, 26B, 27A, 27B:
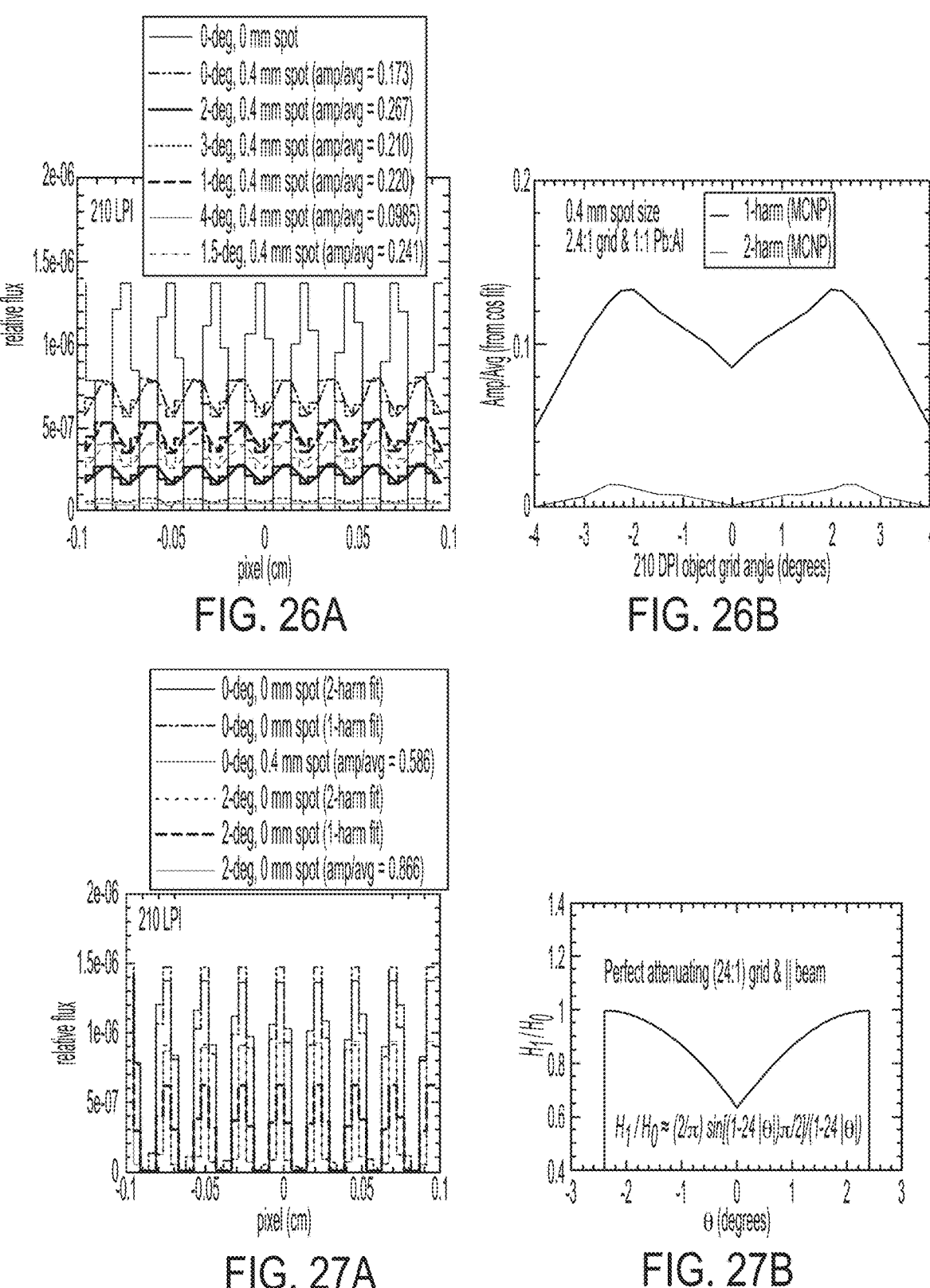
FIGS. 26A and 26B are graphs showing modeled flux at the detector from a 0.4 mm spot size 100 kVp source showing values of fringe visibility fits (26A), and plot of fringe visibility ($H_1/H_0$) along with the second harmonic ratio ($H_2/H_0$) as a function of rotation angle (26B).
FIGS. 27A and 27B are graphs showing modeled flux at the detector from a 0 mm spot size 100 kVp source showing values of fringe visibility fits (27A), and plot of analytical fringe visibility ($H_1/H_0$) for perfect (Pb) attenuation and a parallel beam source (27B).

FIGS. 26A and 26B show modeled flux at the detector from a 0.4 mm spot size 100 kVp source showing values of fringe visibility fits (26A), and plot of fringe visibility ($H_1/H_0$) along with the second harmonic ratio ($H_2/H_0$) as a function of rotation angle (27B). FIG. 26A shows the modeled flux at the detector for various rotation angles. The grid visibility for each angle is determined from a fit to the first two harmonics and is plotted in FIG. 26B. As is in the measurement, a local minimum in visibility appears at zero degrees and increases symmetrically for angular changes from zero with a maximum value just before the fully transmitted grid openings go to zero.

This behavior for x-rays emitted from a 0.4 mm spot at 2 m from the detector is very unexpected. A hint at its underlying origin is revealed by considering an idealized signal from a 0 mm spot (FIG. 27A) or even more strikingly from an idealized parallel beam (FIG. 27B). FIG. 28B shows that an obvious consequence of grid rotation is an effective reduction of transmitted duty-cycle. While a reduction of the fringe amplitude or first harmonic can be seen for increasing $|\theta|$ (smaller effective duty-cycle), the fringe average is reduced by an even greater amount resulting in increased ratio visibility and thus increased scatter sensitivity. Additionally, in the limit of parallel beam and perfect attenuation of the lead, an analytical relationship for harmonic ratios is simply $$\left(\frac{H_n}{H_0}\right)_{\parallel} = \frac{P}{\pi ns}\sin\frac{\pi ns}{P}$$

where s is the effective slit width for the rotated grid. Assuming perfect attenuation for the lead absorber regions the effective slit width as a function of rotation angle is given by $$\frac{s}{P} = \frac{1}{2} - \frac{T}{2s_{1:1}}|\theta|,$$

where P is the grid period, T is the grid thickness, s 1:1 is the width of the transmitting slits for the 1:1 duty-cycle grid and θ is the "small" rotation angle. Also, the effective duty-cycle ($d_c$:1) can then be expressed with $$d_c = \frac{s}{P-s}.$$

In the parallel beam case it is interesting to note that the first harmonic ratio is a maximum when both s/P and the intensity go to zero.

Figure 28:
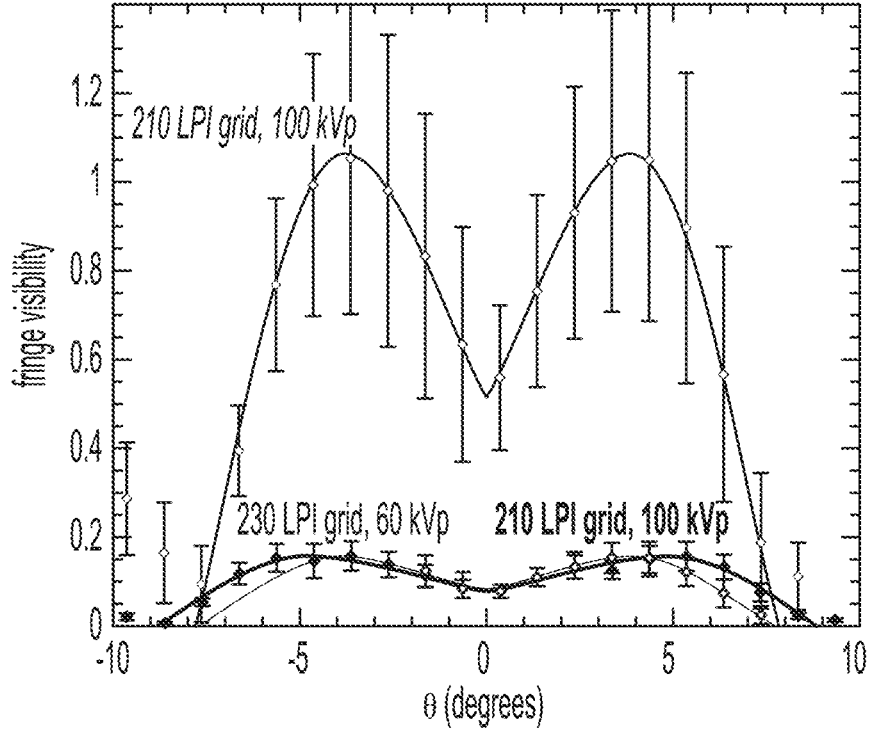
FIG. 28 is a graph showing the modeled fits to fringe visibility measurements with a tilted object grating.

This behavior is relaxed by the more appropriate non-parallel beam and finite spot size physics. The s/P equation above still assumes perfect attenuation, but not a parallel beam and can be used as an approximate mapping from simulated rotation to simulated duty-cycle. A consequence of this mapping is that the analytical relationship for harmonic ratios above can be empirically modified to give a reasonably accurate fit to the non-parallel beam data with $$\frac{H_1}{H_0} = a_0\frac{\sin[a_3(1 - a_1|\theta| + a_2\theta^2)]}{1 - a_1|\theta| + a_2\theta^2}$$

where $a_j$ are four fit parameters. Interpreting $a_1$ as $T/s_{1:1}$ and given θ for the maximum $H_1/H_0$, the equations for s/P and for $d_c$ can be used to infer the grid duty-cycle having maximum sensitivity. FIG. 28 shows that the modified harmonic ratio gives very reasonable fits to rotated object grid measurements indicating that the effect is due to a change in duty-cycle even when the source deviates from a parallel beam. Using the modified harmonic ratio fits, the maximum fringe visibility gives an approximate effective duty-cycle 1:7 for both the 210 LPI grids and 1:4 for the 230 LPI grid.

Additional Cross-Grid Examples

While radiography is an important tool for inspection of objects in many settings, it provides little material information. Phase contrast x-ray imaging provides additional material information compared with commonly used x-ray imaging. With phase contrast x-ray imaging, three images can be obtained: absorption (similar to commonly used x-ray imaging), differential phase, and dark field. Cross-grid moire imaging adapts phase contrast imaging to commonly used x-ray sources with a broad spectrum and possibly large focal spot, and detectors which may have a large field of view but low spatial resolution, while providing a way of distinguishing sample microstructure from the effects of beam hardening. This can be especially beneficial for non-scanning inspection applications involving larger objects such as industrial non-destructive evaluation and use by first responders.

Phase contrast, or multi-contrast x-ray imaging relies on patterning the x-ray beam (using an "object grid") to detect new signatures based on not only attenuation but also directional changes of the x-rays in an object. Herein, "grid" can be used to refer to a grating. In exampled described hereinabove, methods of performing this measurement use penetrating x-rays along with an additional optic such as a detector grid to correct for spectral effects and enable quantitative interpretation of the signal. In some described examples, a high resolution detector can be used to directly image the projections of the object grid and detector grid, with the detector grid rotated 90 degrees relative to the object grid. However, this may not be feasible for use with large field of view detectors, which have larger pixels and cannot resolve the lines. In further described examples, indirect detection may be used, e.g., where an analyzer grid is used to form moire fringes with the object and detector grid regions, but in these examples the object and detector grids cover different locations and the object is scanned across.

In accordance with additional examples, methods involve indirect imaging of crossed object and detector grids, e.g., by using a crosshatched analyzer grid that can be translated in two dimensions. As will be discussed further below, this can enable the use of fine patterning elements with a large detector and a static object.

The crossed analyzer grid forms moiré fringes with both the object and detector grids. By translating the analyzer grid both horizontally and vertically, a series of measurements of the moiré fringes can be made at different phases of the object and detector grid. Translating both directions allows indirect measurements of both patterns, but doing so at each combination can ensure that the patterns are well sampled with different projected spectra. This can allow for the use of arbitrarily fine optics, enabling high sensitivity measurements, with arbitrarily large detectors. This can be important for many applications such as non-destructive examination, medical imaging, and emergency response.

Disclosed additional cross-grid examples relate to the examples described hereinabove (e.g., U.S. application Ser. No. 16/363,989, now issued as U.S. Pat. No. 11,006,912) and moiré scanning examples involving indirect imaging of a moving object described in Ser. No. 17/322,635 (now issued as U.S. Pat. No. 11,639,903 and incorporated by reference herein). While others have used calibration objects to correct for beam hardening influencing a dark field image, that tends to be most effective when the range of materials being inspected is limited. Further other techniques and approaches do not make this type of correction and cannot directly distinguish spectral effects from structural effects when viewing a dark field image. With phase contrast an x-ray beam can be patterned and a detector can be spaced further along the beam axis so that distortions in that pattern can be detected. The detected image can provide information regarding how the x-rays change direction, due to refraction or small angle x-ray scattering. Finer patterns provide the ability to detect smaller angular changes and higher sensitivity to texture and electron density gradients but may not be directly visible on a detector with low spatial resolution. With a large field of view but low spatial resolution detector, a fine pattern can be detected using an additional grating positioned near the detector that matches the projected pattern and then the detector grating can be translated and so that moiré fringes can be detected instead of the directly viewing the pattern.

As discussed above, it has been found that it can be desirable to use a loss of contrast in a projected pattern as a fingerprint for small-angle scattering. However, for x-ray sources with a broad spectrum of energies, it has been further found that objects can preferentially attenuate the more easily attenuated parts of the beam. This can result in the projected pattern having a lower contrast or reduced visibility because the spectrum that is being used to interrogate the object is now different. In Ser. No. 16/363,989, examples described the addition of a grating proximate the detector which would not be sensitive to angular changes given its positioning. This detector grating could then be used to detect the spectral changes and separate the changes from the spectral angular changes associated with the object grating that was positioned proximate the object. However, many of such arrangements correspond to direct imaging, with many being limited to situations in which the pattern is sufficiently large, or the field of view was sufficiently small to allow for direct imaging.

In additional cross-grid examples, radiography can be performed for emergency response, such as where an unknown or threatening object is observed in a public setting and its desirable to image the contents of the object, as well as for medical imaging and non-destructive evaluation. Such examples can use phase contrast to achieve indirect imaging to avoid the requirement of a large detector for direct imaging. For example, larger detectors have pixels that tend to be correspondingly bigger. If direct imaging is to be performed, then an available sensitivity to angular changes would be lower because the patterns used would be coarse. Thus, direct imaging can be impractical or produce images with insufficient resolution. Disclosed cross-grid examples can incorporate both object and detector gratings while leveraging indirect imaging with moiré fringes. In various disclosed examples, an arrangement of object and detector gratings included respective sets of elements that complement each other, e.g., by forming a crossed pattern. An analyzer grating having a pattern matching the projected pattern of the object and detector gratings (e.g., crossed) can then be positioned in the beam path and stepped in relation to the two object and detector grating patterns.

Movement of the analyzer grating (or object and detector gratings), e.g., with a coordinated translation to periodic positions associated with the elements of the projected pattern, can allow for the collection of a set of images that can produce improved images in the application of moiré indirect imaging techniques. Example movements are generally transverse to the direction of propagation of the x-rays, e.g., a beam axis. In many examples herein, transverse refers to perpendicular, approximately perpendicular (e.g., within 5 degrees), within 10 degrees, or within 30 degrees. With such movement, different pattern overlaps between the object, detector, and analyzer gratings can be obtained. For example, where an object grating contains vertical grating elements and a detector grating contains horizontal elements, movement of a crossed analyzer grating horizontally can provide information relating to the object grating, and movement of the crossed analyzer vertically can provide information relating the detector grating.

Accurate extraction of absorption, phase, and scatter information using cross-grid indirect moiré imaging techniques requires careful measurements and data analysis, or image artifacts may result. As will be discussed further, disclosed examples can reduce or eliminate many undesirable artifacts. For example, it can be seen that if the analyzer grating is moved along two separate directions, i.e., one line in one direction (vertical), one line in the other direction (horizontal), as the analyzer grating is moved in the horizontal direction the object and detector gratings are positioned at one particular condition in the vertical direction. Thus, the analyzer grating can be positioned to interrogate a particular voxel of material that is positioned on a horizontal stripe, and the analyzer grating can be translated horizontally to reveal information related to changes in the vertically oriented grating pattern. Errors in alignment can result in patterns which are not perpendicular can be addressed during data analysis, as can errors in phase stepping. Also, the patterns could be positioned on an attenuating portion of the patterns, a transmitting portion, or somewhere in between. Each can provide somewhat different information due to the complexity of the spectral portion of the image data and the fact that even though grating patterns may have orthogonal characteristics, the patterns are not necessarily uncoupled due to coupling through spectral changes that are occurring.

In selected examples, artifact reduction can be achieved with additional scan points being collected along more than a single vertical translation and a single horizontal translation of the analyzer grating. In some examples, a vertical, horizontal, and a diagonal set of scan positions can be used to collect images. In further examples, a more complete array of scan positions can be imaged (e.g., a 6×6 array, 9×9 array, etc.). That a benefit can be obtained from the additional scan positions is non-trivial, and it has been found that it can be used to effectively average spectral information in a way to represent the changes that are occurring with both object and detector grating patterns. As discussed further below, this can be used reduce artifacts in phase contrast images. Various scan paths can be used, such as a snake-like raster pattern, an L-shaped pattern, a triangular pattern, etc. Scan steps can have various amounts and can depend on the grating and projected pattern periodicities. In some examples, 40 micron steps are used though other steps can be suitable, such as 10 micron, 20 micron, 80 micron, 200 micron, etc. In many examples, at least three steps/period are used in scan sequences, though other periodic increments can be suitable (e.g., 4 steps/period, 6, 8, 12, etc.). Micron steps are typically a suitable order of magnitude, but it will be appreciated that other steps and increments can be suitable.

As stated, a 2-d pattern of scan positions can be applied to cross-grid pattern arrangements of object, detector, and analyzer gratings. By using a relative movement of the gratings to define the 2-d pattern, the analyzer grid can distinguish information relating to the object and detector gratings. Further, there can be a subtlety with respect to how the scanning is performed, e.g., by scanning in more than a set of a single horizontal scan line and a single vertical scan line. In comparison to other existing approaches, it should be noted that detector grids are not typically used for spectral corrections, with most avoiding spectral corrections or doing them empirically for only a single material. Thus, disclosed examples can uniquely perform moiré-based techniques by using object and detector gratings and an analyzer grating with a pattern related to the object and detector grating patterns.

Thus, disclosed additional cross-grid examples advantageously can be used for inspection of large objects, as referenced above, e.g., in industrial radiography, medical imaging, and emergency response. In combination with examples in U.S. application Ser. No. 16/363,989 described above (and related beam hardening techniques) and in U.S. application Ser. No. 17/322,635 in which methods of doing phase contrast imaging with penetrating x-rays are described, such additional examples can enable the application of phase contrast imaging for large objects. This can beneficially provide additional material information (density, effective atomic number, and microstructure) relative to conventional x-ray imaging. In contrast to techniques described in Ser. No. 17/322,635, many disclosed cross-grid examples can be applied to a static object. Further, while being able to inspect a static object using indirect imaging while also applying beam hardening correction, disclosed cross-grid examples can address the complexity that exists in which the object and detector gratings are both projecting over the whole image of the object. In other words, rather than separating the field of view into spaced-apart object and detector portions, the analyzer grating can be used (through movement of one or more of the gratings) to reveal information associated with both the object and detector gratings without requiring a movement of the object.

Figure 29:
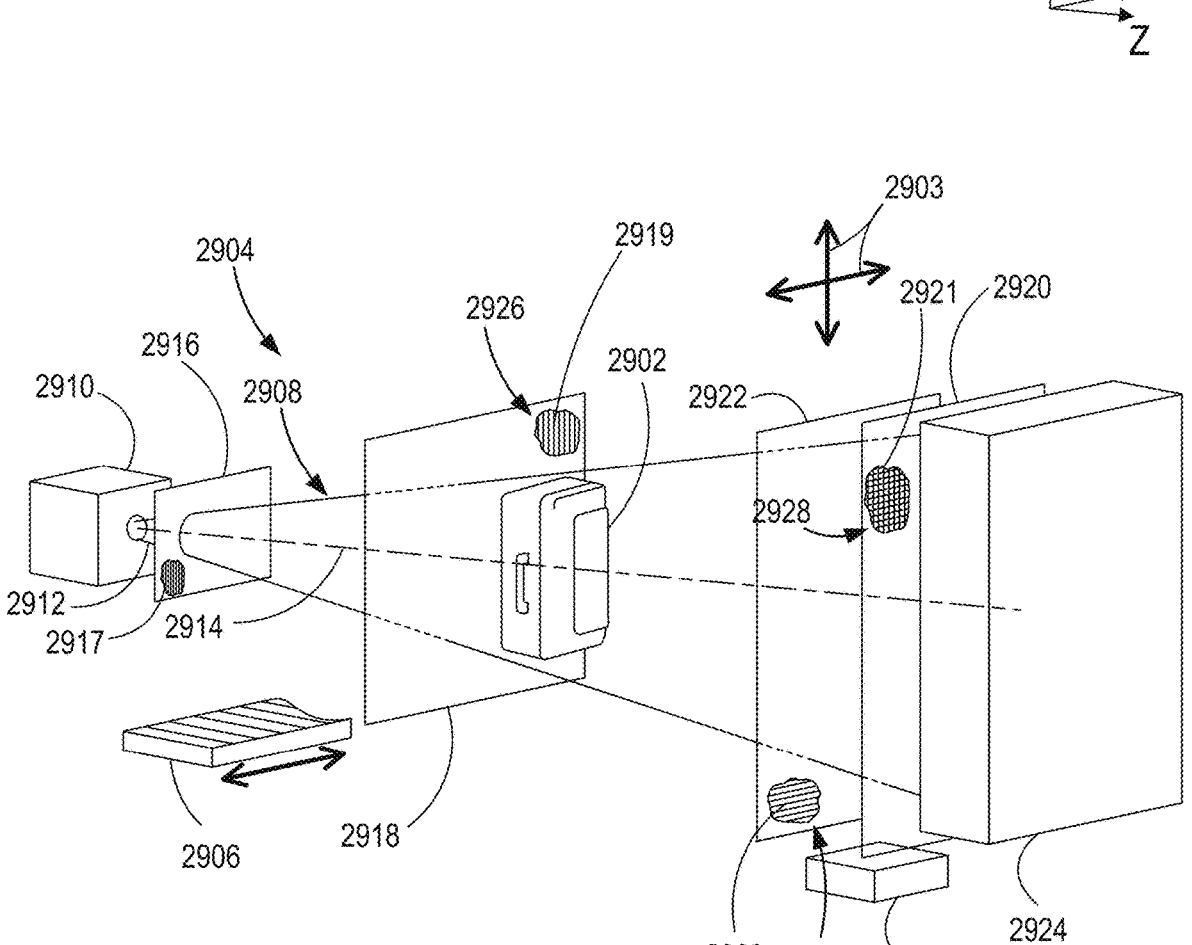
FIG. 29 is a perspective schematic of an example x-ray system that can be used for indirect moiré imaging of objects.

FIG. 29 is an example x-ray system 2900 that can produce indirect moiré images of an object 2902 rather than direct images. The object 2902 can be complete or whole (such as an entire suitcase, container, backpack, device, etc.) or can be a portion of a larger object. In representative examples, the object 2902 can be statically positioned in relation to an x-ray optical arrangement 2904, e.g., by moving the object 2902 with a conveyor 2906 or other movement mechanism into a field of view 2908 of the x-ray optical arrangement 2904, where it remains stationary during the measurement, or by placing the imaging equipment around a static object. The x-ray optical arrangement 2904 can include an x-ray source 2910 situated to produce and direct an x-ray beam 2912 along a beam axis 2914. The x-ray beam 2912 can be directed through a source grating 2916 situated in proximity to the x-ray source 2910. The source grating 2916 can be configured to break up the source x-rays of the x-ray beam 2912 into a plurality of spaced apart x-ray line sources with an arrangement of linear grid elements 2917 (shown vertically arranged in the figure). The line sources can be used to obtain increased resolution for projecting through an object grating 2918. In some examples of the system 2900, the source grating 2916 is not present, such as where the x-ray source 2910 produces spot sizes that are sufficiently small, as discussed previously hereinabove.

The object grating 2918 can be situated near the object 2902 along the beam axis 2914, such as immediately before or after the object 2902. In representative examples, the entirety of a region of interest of the object 2902 receives the x-ray beam 2912. For example, the region of interest can correspond to extend across the entire field of view 2908 or a portion of the field of view 2908. The x-ray beam 2912 continues to propagate through an analyzer grating 2920 and a detector grating 2922 before being detected with an x-ray detector 2924. The analyzer grating 2920 and detector grating 2922 can be situated near the detector 2924, typically with the analyzer grating 2920 situated immediately before the detector 2924 along the beam axis 2914 and the detector grating 2922 preceding the analyzer grating 2920, although the analyzer grating 2920 can also precede the detector grating 2922. In representative examples, the entirety of the x-ray beam 2912 that propagates through the object 2902 also propagates through the analyzer grating 2920 and detector grating 2922.

The object grating 2918 has a set of grating elements 2919 arranged in an object grating element pattern 2926 and the detector grating 2922 has a set of grating elements 2923 arranged in a detector grating element pattern 2927 which is different from the object grating element pattern 2926. In some examples, the object grating element pattern 2926 and the detector grating element pattern 2927 differ at least by or only by a rotation angle, typically 90 degrees. For example, in many arrangements, the grating elements 2919 can be a set of linear grating elements perpendicularly arranged with respect to the beam axis 2914 (e.g., vertical, or in the 'y' direction in FIG. 29) and the grating elements 2921 can be a set of linear grating elements also perpendicularly with respect to the beam axis 2914 but further perpendicularly arranged with respect to the grating elements 2919 (e.g., horizontal, or in the 'x' direction in FIG. 29).

The analyzer grating 2920 has a set of grating elements 2921 arranged in an analyzer grating element pattern 2928. In representative examples, the analyzer grating element pattern 2928 is configured to have significant correspondence to a projected image of the object grating element pattern 2926 and the detector grating element pattern 2927. Thus, in examples in which the linear grating elements 2919 define the object grating element pattern 2926 as a set of stripes extending in a first direction perpendicular to the beam axis 2914 and the linear grating elements 2923 define the detector grating element pattern 2927 as a set stripes extending in a second direction perpendicular to both the beam axis 2914 and the first direction, the analyzer grating element pattern 2928 can be arranged in a crossed-grid pattern. Such an analyzer grating can also be referred to as a crossed-line analyzer grid, crosshatched analyzer grid, etc. Perpendicular linear grating elements can be convenient because they are separable from each other, but other sets of elements defining respective patterns can be suitable provided they can be separable. Other separable patterns typically include some orthogonality characteristic, but other non-orthogonal patterns might be used provided they can be disentangled from each other, which in some examples can be done after detection through mathematical analysis. In general, patterns are separable where they are different from each other such that a grating movement can allow detection of changes associated with one pattern over the other.

The degree of significant correspondence results in a moiré pattern formed between the object grating and analyzer grating, as well as a moiré pattern formed by the detector grating and analyzer grating. One or more the gratings 2918, 2920, 2922 can be moved relative to the other(s) and multiple images can be collected to perform moiré phase contrast imaging, extracting absorption, differential phase, and dark field images. To achieve such movement, in many examples, the analyzer grating 2920 is translated in directions 2903 with a movement stage 2930 while the object and detector gratings 2918, 2922 remain fixed. The degree of significant correspondence need not be defined by a perfect overlap in every example, as such an overlap may be impractical to achieve. However, in many examples, such an enhanced correspondence can be advantageous. In general, the greater the correspondence between the object grating 2918 and analyzer grating 2920, or between the detector grating 2922 and analyzer grating 2920, the greater contrast will be present in the resulting moiré fringes, resulting in increased signal-to-noise when extracting absorption, differential phase, and dark field images. Where there is an insufficient matching between the patterns 2926, 2927 to the pattern 2928, beat frequencies can occur within a pixel with successive translations resulting moiré fringes which are too fine to detect, making it impossible to extract absorption, differential phase, and dark field images. By way of example, where the object and detector gratings having grating elements defining respective patterns of dots (i.e., rather than stripes or other patterns), the analyzer grating pattern (which contains an additive combination of both patterns) should be able to be moved across the projection of the object and detector grating patterns in order to have knowledge as to which set of dots is being sampled. In other words, the pattern from which phase information is being obtained should be able to be selectable, while at the same time the patterns should have the same or sufficiently similar response to a change in spectrum. For an object placed in the path of the beam 2912, the beam 2912 should affect the detected spectra in the same or similar way.

Object and detector gratings 2918, 2922 with orthogonally arranged lines (or stripes) as respective grating elements 2919, 2923 can be particularly suitable. Such a pattern set can afford an explicit direction to probe either set with an analyzer grating 2920 containing a crossed grid pattern of grating elements 2921. This probing is allowed because a relative movement of the aligned patterns 2926, 2927, 2928 can be provided, e.g., through movement of the analyzer grating 2920 with the movement stage 2930 along directions 2903, movement of the object and detector gratings 2918, 2922 to achieve a similar effect, or a combination of movements. In some examples, grating elements 2919, 2921, 2923 of one or more of the object, analyzer, and detector gratings 2918, 2920, 2922 are not continuous elements, e.g., they can be dashed, dots (square or with roundedness), or include other discontinuities or shape variations, such as periodic variations associated with any periodicity associated with the grating elements 2919, 2921, 2923. In general, differences between grating patterns amongst one or more of the gratings are sufficient to provide separability, such as to discern movement of one relative to another.

In some examples, enhancement in phase contrast moiré imaging can be achieved by collecting x-ray image data with the detector 2924 at multiple movement positions of the gratings 2918, 2920, 2922 relative to each other. In particular, it has been found that the varied movement positions result in different samples of the incident x-ray spectrum due to beam hardening, and improper averaging can result in undesirable artifacts. These artifacts can be removed from produced phase contrast images in part by translating to more positions than an "L" shaped set of scan positions of the analyzer grating 2920 relative to the object and detector gratings 2918, 2922. For example, the movement of gratings can be rastered or painted to collect a set of scan positions that extends to form a 2-d array of collected images. It has also been found that a significant benefit with respect to image sampling can be obtained without a full 2-d array, e.g., by collecting a set of images along an "L" shaped set of scan positions and a diagonal set of scan positions. The data collected from the additional scan positions allows for averaging over different spectra, and can be used to produce an improved phase contrast image in which artifacts are removed that would otherwise obscure attenuation characteristics in the image. Such characteristics can be associated with material specific identifications. Careful selection of scan and image collection positions can provide artifact reduction with the minimal number of images collected, reducing the duration of scanning and image collection processes, thereby enhancing time-critical image collection and analysis.

2-D Phase Scanning

As discussed above, analyzer gratings can include a combination of object and detector grating patterns and a relative movement between gratings can be used to produce moiré patterns and phase contrast images. For convenience in describing 2-D phase scanning techniques that can be used in accordance with additional cross-grid examples, an analyzer grating (e.g., grating 2920) that includes a 2-dimensional rectangular grid of holes can be used, though it will be appreciated that other patterns may be used as discussed herein.

The hole pattern of the analyzer grating can be used to phase scan moiré patterns of both an object grating and a perpendicularly arranged detector grating (e.g., object grating 2918 and detector grating 2922). The phase scan can occur in the same section of the field of view of a detector (e.g., detector 2924) without replacing any of the gratings. Automated phase steps can be performed on the analyzer grating with a motorized translation stage (e.g., movement stage 2930). Alternatively, the object and detector gratings may be translated or another translational arrangement may be provided.

At multiple positions provided by x- and y-translations of the grating and/or gratings, the x-ray beam can be directed through the object and gratings and x-ray phase scan images can be collected with the detector. Each of the collected images associated with the x- and y-direction translation step sequences can be analyzed. For example, the Fourier transforms (FT) can be taken of the phase scan images, and the peaks of the x- and y-analyzer grid patterns can be located on the FT image. The phase of the FT at the pixel corresponding to a peak can provide a measurement of the phase displacement of the analyzer grid relative to the object and detector grids. For each pixel in the untransformed images, the sequence of phase step images gives a sinusoidal pattern with measured intensity on the vertical axis and the phase of the step on the horizontal axis. The first two terms of the Fourier transform of this sequence gives the mean value, amplitude, and phase for the pixel. The contrast of the sequence for that pixel is the ratio of the amplitude to the mean. The absorption is the ratio of the mean values of an object image and a flatfield image; the phase shift is the difference in phase between the object and flatfield images; and the contrast reduction (related to the scatter) is the ratio of the contrasts of the object and flatfield images.

Figure 30:
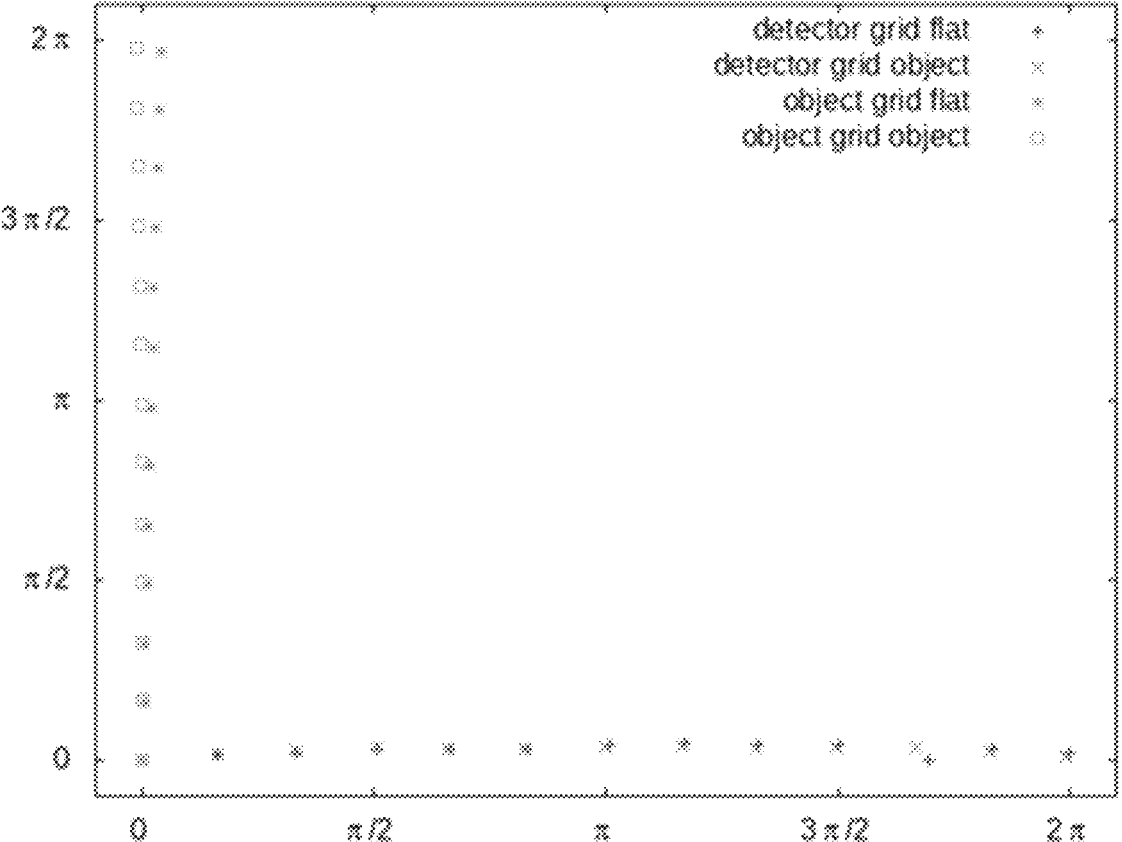
FIG. 30 is a graph showing horizontal and vertical phase positions where indirect moiré images are collected.

A cross-talk between the x- and y-stepping directions can be present. A stepping sequence along the x-direction, for example, might not be purely constant in y-, thereby allowing phase from the perpendicular grid to influence the signal intended to be measured. Such a cross-talk can be seen in FIG. 30, which shows horizontal and vertical phases during a scan and image collection at 13 positions in the x- and y-directions. Small excursions in the transverse direction are seen. While these are reproducible for the detector grating sequence for the object and flatfield image, a drift is present in the transverse direction phase for the object grating scan.

To correct for this, the horizontal phase can be denoted by μ and the vertical phase by v. Because only the lowest order terms (first and second) in the Fourier transform are generally of interest, every pixel (x,y) can be expressed as the following function of μ and v:

$$I(x, y; \mu, v) =$$

$$M(x, y) + A_d(x, y)\cos[-\mu - \phi_d(x, y)] + A_o(x, y)\cos[-v - \phi_o(x, y)]$$

with M the mean value of the pixel, $A_d$, the amplitude of the detector grid, $A_o$ the amplitude of the object grid, $\phi_d$ the detector grid phase shift, and $\phi_o$ the object grid phase shift. The minus signs in the cosine function are due to the code for determining the 1-D parameters being originally coded as:

$$\sum_i I_{d,i}\cos[\mu_i]$$

(and similarly for the object grid), and so integrating over cos[μ] picks out the cos[−μ] Fourier component. From the 1-D Fourier transforms, we have a good first estimate of all five parameters. The phase step sequence with N steps in each direction gives 2N data points $I_m$ (x, y; μ, v) at known (μ, v) as described earlier. This allows us to solve for the 2-D case including drift by minimizing:

$$\chi^2 = \sum_{m=1}^{2N} (I_m(x, y; \mu, v) - I(x, y; \mu, v))^2.$$

This can be achieved with a Levenberg-Marquardt minimizer algorithm.

FIGS. 31A-33B show phase contrast images comparing an uncorrected and phase drift corrected images for a test object. More specifically, FIG. 31A shows an absorption image and FIG. 31B shows a drift corrected absorption image. FIG. 32A shows a contrast ratio image for the same image in FIG. 31A and FIG. 32B shows a contrast ratio image for the same drift corrected image from FIG. 31B. FIG. 33A shows a phase shift image for the same image in FIG. 31A and FIG. 33B shows a phase shift image for the same drift corrected image from FIG. 31B.

Spectral Effects in Moiré Scanning

Figures 34A, 34B, 34C, 34D, 34E, 34F, 34G, 34H:
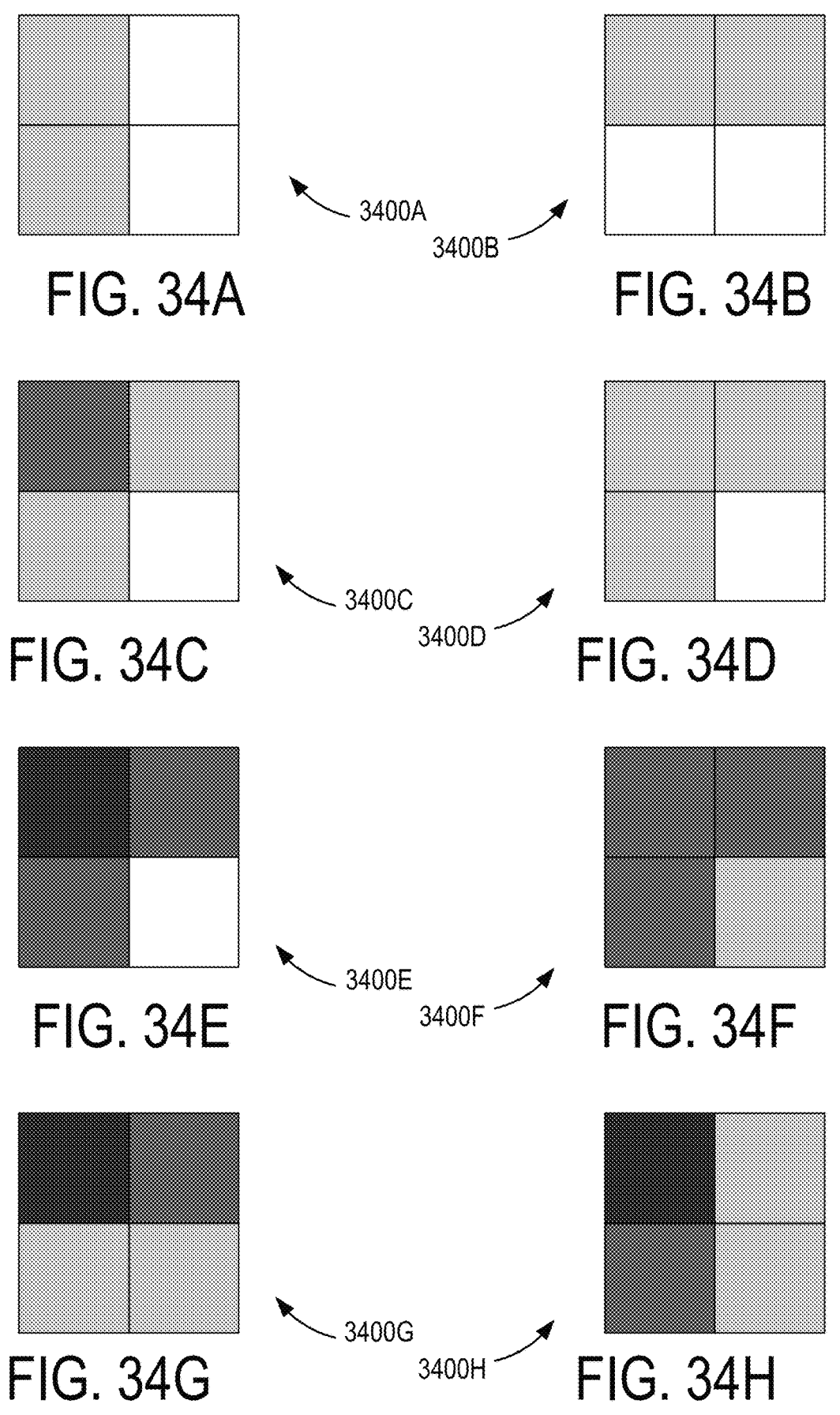

FIGS. 34A-34H show a set of grating unit cell representations for object, detector, and analyzer gratings having vertical, horizontal, and crossed grating elements, respectively. More particularly, FIG. 34A shows a tiled set defining a unit cell 3400A of an object grating having a repeating set of vertically arranging grating elements. Similarly, FIG. 34B shows a tiled set defining a unit cell 3400B of a detector grating having a repeating set of horizontally arranging grating elements. A shown in FIG. 34C, when the unit cells 3400A, 3400B are overlayed, a unit cell pattern 3400C is produced. Similarly, FIG. 34D shows a tiled set defining a unit cell pattern 3400D of an analyzer grating having a repeating set of vertical and horizontal elements. As can be seen, a geometry of the pattern 3400D matches a geometry of the pattern 3400C. While the analyzer grating can be shifted in any direction to arbitrarily position the open element in its lower right, it is useful to examine extreme positions. For the high part of the object and detector grating fringe, the white squares can be allowed to overlap, forming the unit cell 3400E shown in FIG. 34E. For the low parts of the fringes of both gratings, the unit cell 3400F in FIG. 34F is seen. This can be achieved by positioning the white square of the analyzer grating unit cell 3400D in the upper left. Where the detector grating is positioned high and the object grating is positioned low, the unit cell 3400G can be obtained, as shown in FIG. 34G. Where the detector grating is low and the object grating is high, the unit cell 3400H can be obtained, as shown in FIG. 34H. As shown, FIGS. 34A-34H show a specific simplified example in which each grating provides a uniform 50% attenuation.

A mathematical analysis of the spectral effects proceeds as follows. Integrated signals can be defined:

| $S_{hh}$ | Integrated signal of one cell in detector grid high, object grid high case |
|---|---|
| $S_{lh}$ | Integrated signal of one cell in detector grid low, object grid high case |
| $S_{hl}$ | Integrated signal of one cell in detector grid high, object grid low case |
| $S_{ll}$ | Integrated signal of one cell in detector grid low, object grid low case |

Visibilities can then be formed as:

| $V_{oh} = \dfrac{S_{hh} - S_{hl}}{S_{hh} + S_{hl}}$ | Object grid visibility in the high signal region of the detector grid fringe. |
|---|---|

$$V_{dh} = \frac{S_{hh} - S_{lh}}{S_{hh} + S_{lh}}$$   Object grid visibility in the low signal region of the detector grid fringe.

$$V_{ol} = \frac{S_{lh} - S_{ll}}{S_h + S}$$   Detector grid visibility in the high signal region of the object grid fringe.

$$V_{dl} = \frac{S_{hl} - S_{ll}}{S_{hl} + S_{ll}}$$   Detector grid visibility in the low signal region of the object grid fringe.

For the case where an object is partially attenuating the beam:

$\tilde{S}_{hh}$  Integrated signal of one cell in detector grid high, object grid high, object present
$\tilde{S}_{lh}$  Integrated signal of one cell in detector grid low, object grid high, object present
$\tilde{S}_{hl}$  Integrated signal of one cell in detector grid high, object grid low, object present
$\tilde{S}_{ll}$  Integrated signal of one cell in detector grid low, object grid low, object present $$\tilde{V}_{oh} = \frac{\tilde{S}_{hh} - \tilde{S}_{hl}}{\tilde{S}_{hh} + \tilde{S}_{hl}}$$   Object grid visibility in the high signal region of the detector grid fringe in the object's shadow.

$$\tilde{V}_{ol} = \frac{\tilde{S}_{lh} - \tilde{S}_{ll}}{\tilde{S}_{lh} + \tilde{S}_{ll}}$$   Object grid visibility in the low signal region of the detector grid fringe in the object's shadow.

$$\tilde{V}_{dh} = \frac{\tilde{S}_{hh} - \tilde{S}_{lh}}{\tilde{S}_{hh} + \tilde{S}_{lh}}$$   Detector grid visibility in the high signal region of the object grid fringe in the object's shadow.

$$\tilde{V}_{dl} = \frac{\tilde{S}_{hl} - \tilde{S}_{ll}}{\tilde{S}_{hl} + \tilde{S}_{ll}}$$   Detector grid visibility in the low signal region of the object grid fringe in the object's shadow.

The response usually can be envisioned as a ratio of the grid visibilities with and without the object present, to quantify how the object changes the visibility:

$$\rho_{oh} = \frac{\tilde{V}_{ol}}{V_{oh}}$$   Object grid visibility ratio with and without object present in high region of detector grid fringe.

$$\rho_{ol} = \frac{\tilde{V}_{ol}}{V_{ol}}$$   Object grid visibility ratio with and without object present in low region of detector grid fringe.

$$\rho_{dh} = \frac{\tilde{V}_{dh}}{V_{dh}}$$   Detector grid visibility ratio with and without object present in high region of object grid fringe.

$$\rho_{dl} = \frac{\tilde{V}_{dl}}{V_{dl}}$$   Detector grid visibility ratio with and without object present in low region of object grid fringe.

Then, to correct for spectral changes due to wavelength-dependent absorption by the object altering the transmissivity of the grids (also referred to as beam hardening), the object grid visibility ratio is divided by the detector grid visibility ratio:

$$R_{hh} = \frac{\rho_{oh}}{\rho_{dh}}$$   Beam hardened corrected visibility ratio, object grid fringe high, detector grid fringe high region.

$$R_{lh} = \frac{\rho_{oh}}{\rho_{dl}}$$   Beam hardened corrected visibility ratio, object grid fringe high, detector grid fringe low region.

$$R_{hl} = \frac{\rho_{ol}}{\rho_{dh}}$$   Beam hardened corrected visibility ratio, object grid fringe low, detector grid fringe high region.

$$R_{ll} = \frac{\rho_{ol}}{\rho_{dl}}$$   Beam hardened corrected visibility ratio, object grid fringe low, detector grid fringe low region.

Thus, a necessary condition for, e.g., $R_{hh}=1$ and $R_{lh}=1$ (as one might expect for a non-scattering object), is that $\rho_{dh}=\rho_{dl}$. Requiring R=1 for all combinations of fringe locations implies that all $\rho$ must be equal. Conversely, all $\rho$ being equal is sufficient to ensure that R=1.

$$\rho_{oh} = \frac{\tilde{S}_{hh} - \tilde{S}_{hl}}{\tilde{S}_{hh} + \tilde{S}_{hl}} \frac{S_{hh} + S_{hl}}{S_{hh} - S_{hl}}$$

$$\rho_{ol} = \frac{\tilde{S}_{lh} - \tilde{S}_{ll}}{\tilde{S}_{lh} + \tilde{S}_{ll}} \frac{S_{lh} + S_{ll}}{S_{lh} - S_{ll}}$$

$$\rho_{dh} = \frac{\tilde{S}_{hh} - \tilde{S}_{lh}}{\tilde{S}_{hh} + \tilde{S}_{lh}} \frac{S_{hh} + S_{lh}}{S_{hh} - S_{lh}}$$

$$\rho_{dl} = \frac{\tilde{S}_{hl} - \tilde{S}_{ll}}{\tilde{S}_{hl} + \tilde{S}_{ll}} \frac{S_{hl} + S_{ll}}{S_{hl} - S_{ll}}$$

Therefore, a uniform reduction in visibility signal due to the presence of the object will result in all $\rho=1$, and thus result in no artifacts.

It can be immediately seen that in regions where the object casts no shadow, R remains unity; with $\tilde{V}=V$, $\rho=1$ for both detector and object grating, and thus R=1. So, if there are spectral effects causing artifacts, they will not be present in regions of no attenuation. Further, the spectral effects can be observed to increase with increasing attenuation, making such artifacts more prominent in the high attenuation regions.

The conditions necessary for $\rho$ to remain equal as the beam is hardened can be established by taking the total derivative with respect to the $\tilde{S}$'s:

$$\delta\rho_{oh} =$$

$$\frac{S_{hh} + S_{hl}}{S_{hh} - S_{hl}} \left[ \left( \frac{1}{\tilde{S}_{hh} + \tilde{S}_{hl}} - \frac{\tilde{S}_{hh} - \tilde{S}_{hl}}{(\tilde{S}_{hh} + \tilde{S}_{hl})^2} \right) \delta\tilde{S}_{hh} - \left( \frac{1}{\tilde{S}_{hl} + \tilde{S}_{ll}} + \frac{\tilde{S}_{hl} - \tilde{S}_{ll}}{(\tilde{S}_{hh} + \tilde{S}_{hl})^2} \right) \delta\tilde{S}_{hl} \right]$$

$$\delta\rho_{ol} =$$

$$\frac{S_{lh} + S_{ll}}{S_{lh} - S_{ll}} \left[ \left( \frac{1}{\tilde{S}_{lh} + \tilde{S}_{ll}} - \frac{\tilde{S}_{lh} - \tilde{S}_{ll}}{(\tilde{S}_{lh} + \tilde{S}_{ll})^2} \right) \delta\tilde{S}_{lh} - \left( \frac{1}{\tilde{S}_{lh} + \tilde{S}_{ll}} + \frac{\tilde{S}_{lh} - \tilde{S}_{ll}}{(\tilde{S}_{lh} + \tilde{S}_{ll})^2} \right) \delta\tilde{S}_{ll} \right]$$

$$\delta\rho_{dh} =$$

$$\frac{S_{hh} + S_{lh}}{S_{hh} - S_{lh}} \left[ \left( \frac{1}{\tilde{S}_{hh} + \tilde{S}_{lh}} - \frac{\tilde{S}_{hh} - \tilde{S}_{lh}}{(\tilde{S}_{hh} + \tilde{S}_{lh})^2} \right) \delta\tilde{S}_{hh} - \left( \frac{1}{\tilde{S}_{hh} + \tilde{S}_{lh}} + \frac{\tilde{S}_{hh} - \tilde{S}_{lh}}{(\tilde{S}_{hh} + \tilde{S}_{lh})^2} \right) \delta\tilde{S}_{lh} \right]$$

$$\delta\rho_{dl} =$$

-continued $$\frac{S_{hl} + S_{ll}}{S_{hl} - S_{ll}}\left[\left(\frac{1}{\tilde{S}_{hl} + \tilde{S}_{ll}} - \frac{\tilde{S}_{hl} - \tilde{S}_{ll}}{(\tilde{S}_{hl} + \tilde{S}_{ll})^2}\right)\delta\tilde{S}_{hl} - \left(\frac{1}{\tilde{S}_{hl} + \tilde{S}_{ll}} + \frac{\tilde{S}_{hl} - \tilde{S}_{ll}}{(\tilde{S}_{hl} + \tilde{S}_{ll})^2}\right)\delta\tilde{S}_{ll}\right]$$

If we start from the no-object condition, then $S=\tilde{S}\,\forall S$ and:

$$\rho_{oh} = \left(\frac{1}{S_{hh} - S_{hl}} - \frac{1}{S_{hh} + S_{hl}}\right)\delta\tilde{S}_{hh} - \left(\frac{1}{S_{hh} - S_{hl}} + \frac{1}{S_{hh} + S_{hl}}\right)\delta\tilde{S}_{hl}$$

$$\delta\rho_{ol} = \left(\frac{1}{S_{lh} - S_{ll}} - \frac{1}{S_{lh} + S_{ll}}\right)\delta\tilde{S}_{lh} - \left(\frac{1}{S_{lh} - S_{ll}} + \frac{1}{S_{lh} + S_{ll}}\right)\delta\tilde{S}_{ll}$$

$$\delta\rho_{dh} = \left(\frac{1}{S_{hh} - S_{lh}} - \frac{1}{S_{hh} + S_{lh}}\right)\delta\tilde{S}_{hh} - \left(\frac{1}{S_{hh} - S_{lh}} + \frac{1}{S_{hh} + S_{lh}}\right)\delta\tilde{S}_{lh}$$

$$\delta\rho_{dl} = \left(\frac{1}{S_{hl} - S_{ll}} - \frac{1}{S_{hl} + S_{ll}}\right)\delta\tilde{S}_{hl} - \left(\frac{1}{S_{hl} - S_{ll}} + \frac{1}{S_{hl} + S_{ll}}\right)\delta\tilde{S}_{ll}$$

or:

$$\delta\rho_{oh} = \frac{2S_{hl}\delta\tilde{S}_{hh} - 2S_{hh}\delta\tilde{S}_{hl}}{S_{hh}^2 - S_{hl}^2}$$

$$\delta\rho_{ol} = \frac{2S_{ll}\delta\tilde{S}_{lh} - 2S_{lh}\delta\tilde{S}_{ll}}{S_{lh}^2 - S_{ll}^2}$$

$$\delta\rho_{dh} = \frac{2S_{lh}\delta\tilde{S}_{hh} - 2S_{hh}\delta\tilde{S}_{lh}}{S_{hh}^2 - S_{lh}^2}$$

$$\delta\rho_{dl} = \frac{2S_{ll}\delta\tilde{S}_{hl} - 2S_{hl}\delta\tilde{S}_{ll}}{S_{hl}^2 - S_{ll}^2}$$

which can be written as a matrix equation:

$$\overrightarrow{\delta\rho} = \overleftrightarrow{A}\,\overrightarrow{\delta\tilde{S}}.$$

The condition that all $\rho$ remain the same means $\overrightarrow{\delta\rho}=\delta\rho\,\overrightarrow{1}$. Thus, the necessary condition of the lack of artifacts can be solved for:

$$\overrightarrow{\delta\tilde{S}} = \delta\rho\,\overleftrightarrow{A}^{-1}\overrightarrow{1}.$$

For the special case of $\rho$ remaining unchanged, $\overleftrightarrow{A}$ must be singular and $\overrightarrow{\delta\tilde{S}}$ within its null space. At first it appears unpromising for avoiding spectral artifacts, as it requires a highly cooperative target material that attenuates the spectrum in a certain way. Also, the signals are expected to be attenuated rather than amplified, so that every $\delta\tilde{S}<0$.

Special cases can exist for identical object and detector gratings. For example, while it might not always be possible to choose the object being imaged, the gratings and associated characteristics can be chosen. In many examples, the thickness, composition, and projected periods of the object and detector grids can be matched as closely as possible. Where this is achieved, $S_{lh}=S_{hl}$ and $\tilde{S}_{lh}=\tilde{S}_{hl}$. Consequently, $V_{oh}=V_{dh}\equiv V_h$, $V_{ol}=V_{dl}\equiv V_l$, $\tilde{V}_{oh}=\tilde{V}_{dh}\equiv\tilde{V}_h$, and $\tilde{V}_{ol}=\tilde{V}_{dl}\equiv\tilde{V}_l$. This leads to $\rho_{oh}=\rho_{dh}$ and $\rho_{ol}=\rho_{dl}$. Thus $R_{hh}=1$, $R_{lh}=1/R_{hl}$, and $R_{ll}=1$. It is now the mixed high/low fringe regions between the two gratings that give rise to the beam hardening fringe artifacts, while the high/high and low/low regions correct out as desired.

Special cases can also exist for blurred object gratings. The finite size of the x-ray spot and imperfect source grating corrections will, in practice, lead to lower visibility of the object grating compared to the detector grating. To estimate the effect of grid blurring, it can be assumed that for perfect resolution the detector grating and object grating are identical except for a reflection and 90-degree rotation, but due to blurring a fraction f of the object grating shadow signal spills over into the unshaded region and vice versa. The subscript u is used to signify the unblurred quantity, so for example $S_{hh,u}$, $S_{hl,u}$, $S_{ll,u}$, and $S_{ll,u}$ are the unblurred signals. If identical unblurred shadows of object and detector grid ($S_{hl,u}=S_{lh,u}$) are assumed:

$$S_{hh} = (1-f)S_{hh,u} + fS_{hl,u}$$

$$S_{hl} = (1-f)S_{hl,u} + fS_{hh,u}$$

$$S_{lh} = (1-f)S_{lh,u} + fS_{ll,u}$$

$$S_{ll} = (1-f)S_{ll,u} + fS_{hl,u}$$

The blurring in this case is geometrical, and thus spectrum independent. Therefore, the shadowed signals have the same relationship to the corresponding unblurred signals as do the unshaded signals.

$$V_{oh} = \frac{(1-f)S_{hh,u} + fS_{hl,u} - (1-f)S_{hl,u} - fS_{hh,u}}{(1-f)S_{hh,u} + fS_{hl,u} + (1-f)S_{hl,u} + fS_{hh,u}} =$$

$$\frac{(1-2f)S_{hh,u} - (1-2f)S_{hl,u}}{S_{hh,u} + S_{hl,u}} = (1-2f)V_{oh,u}.$$

$$V_{dh} = \frac{(1-f)S_{hh,u} + fS_{hl,u} - (1-f)S_{ll,u} - fS_{ll,u}}{(1-f)S_{hh,u} + fS_{hl,u} + (1-f)S_{ll,u} + fS_{ll,u}} =$$

$$\frac{(1-f)S_{hh,u} - (1-2f)S_{hl,u} - fS_{ll,u}}{(1-f)S_{hh,u} + S_{hl,u} + fS_{ll,u}}$$

Similarly:

$$V_{ol} = (1-2f)V_{ol,u}$$

$$V_{dl} = \frac{fS_{hh,u} + (1-2f)S_{hl,u} - (1-f)S_{ll,u}}{fS_{hh,u} + S_{hl,u} + (1-f)S_{ll,u}}$$

Because (1–2f) factors out of the object grating visibilities, it cancels when taking the $\rho$ ratios for the object grating. Consequently, $\rho_{oh}=\rho_{oh,u}$ and $\rho_{ol}=\rho_{ol,u}$. The same does not apply for the detector grating $\rho$ ratios. This breaks the symmetry that was had in the perfect resolution case, so the assurance that $R_{hh}=R_{ll}=1$ is lacking.

Figure 35A:
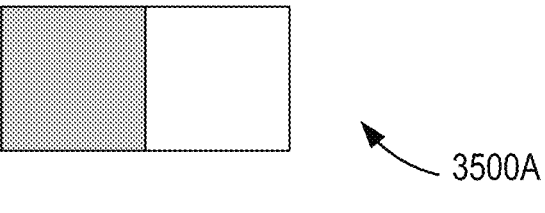
FIGS. 35A-35C are schematic depictions of unit cells object, detector, and analyzer gratings, according to some examples.
Figure 35B:
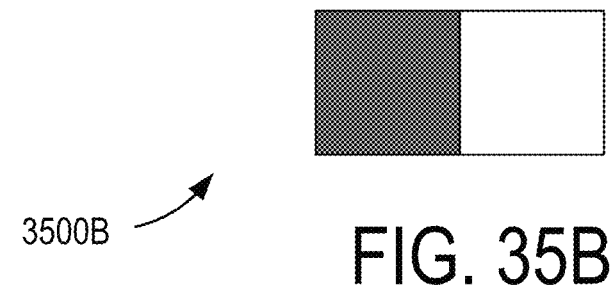
Figure 35C:
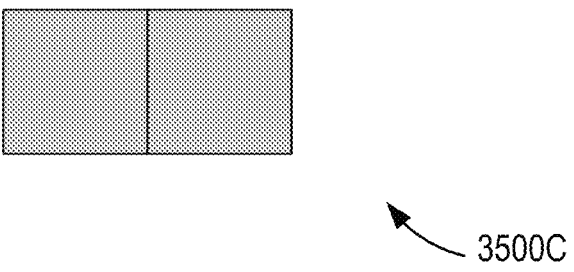

For many sequential moiré imaging examples, only a two-square cell for tiling need be considered. The detector, object, and analyzer grating all have a tiling cell like cell pattern 3500A shown in FIG. 35A. The maximum transmission regions of the moiré fringes can look similar to the cell pattern 3500B in FIG. 35B while the minimum transmission regions can look similar to the cell pattern 3500C in FIG. 35C.

Integrated signals can be defined:

$S_{oh}$  Integrated signal of one cell in the object grid image in a high signal part of the fringe.
$S_{ol}$  Integrated signal of one cell in the object grid image in a low signal part of the fringe.

-continued $S_{dh}$    Integrated signal of one cell in the detector grid image in a high signal part of the fringe.
$S_{dl}$    Integrated signal of one cell in the detector grid image in a low signal part of the fringe.

The visibilities are:

| | |
|---|---|
| $$V_o = \dfrac{S_{oh} - S_{ol}}{S_{oh} + S_{ol}}$$ | Object grid visibility. |
| $$V_d = \dfrac{S_{dh} - S_{dl}}{S_{dh} + S_{dl}}$$ | Detector grid visibility. |

And for the attenuated beam:

$\tilde{S}_{oh}$   Signal of a cell in the object grid image in a high part of the fringe with object present. present.
$\tilde{S}_{ol}$   Signal of a cell in the object grid image in a low part of the fringe with object
$\tilde{S}_{dh}$   Signal of a cell in the detector grid image in a high part of the fringe with object present.
$\tilde{S}_{dl}$   Signal of a cell in the detector grid image in a low part of the fringe with object present.

| | |
|---|---|
| $$\tilde{V}_o = \dfrac{\tilde{S}_{oh} - \tilde{S}_{ol}}{\tilde{S}_{oh} + \tilde{S}_{ol}}$$ | Object grid visibility with object present. |
| $$\tilde{V}_d = \dfrac{\tilde{S}_{dh} - \tilde{S}_{dl}}{\tilde{S}_{dh} + \tilde{S}_{dl}}$$ | Detector grid visibility with object present. |

Again, the response can be envisioned as ratios of the grating visibilities with and without the object present, to quantify how the object changes the visibility.

| | |
|---|---|
| $$\rho_o = \dfrac{\tilde{V}_o}{V_o}$$ | Object grid visibility ratio with and without object present. |
| $$\rho_d = \dfrac{\tilde{V}_d}{V_d}$$ | Detector grid visibility ratio with and without object present. |

This leads to a single beam hardened corrected visibility ratio:

| | |
|---|---|
| $$R = \dfrac{\rho_o}{\rho_d}$$ | Beam hardened corrected visibility ratio. |

The same fringe-dependent beam hardening artifacts seen with the cross grid moiré set-up are not seen with only one ratio. In many examples, the detector grating and object grating are provided with the same thickness and material composition. In this case, for an ideal point source, the detector grid attenuation will be the same as that of the object grid so that $S_{oh} = S_{dh}$, $S_{ol} = S_{dl}$, $\tilde{S}_{oh} = \tilde{S}_{dh}$, and $\tilde{S}_{ol} = \tilde{S}_{dl}$. For this case, $V_o = V_d$ and $\tilde{V}_o = \tilde{V}_d$ so that $\rho_o = \rho_d$ and, in the absence of scattering, R=1. In practice, it can be seen that the object grating visibility is usually significantly less than that for the detector grating, which may be due to the blurring from a finite sized x-ray source and imperfect corrections with the source grating.

To estimate the effect of grid blurring, a fraction f of the object grating shadow signal can be assumed to spill over into the unshaded region and vice versa. For the unblurred signal as above, the blurred object grid signal is:

$$S_{oh} = (1 - f)S_{dh} + fS_{dl}$$

$$S_{ol} = (1 - f)S_{dl} + fS_{dh}$$

$$V_o = \frac{(1 - f)S_{dh} + fS_{dl} - (1 - f)S_{dl} - fS_{dh}}{(1 - f)S_{dh} + fS_{dl} + (1 - f)S_{dl} + fS_{dh}} =$$

-continued $$\frac{(1 - 2f)S_{dh} - (1 - 2f)S_{dl}}{S_{dh} + S_{dl}} = (1 - 2f)V_d.$$

The blurring in this case is geometrical, and thus spectrum independent. Therefore:

$$\tilde{V}_o = (1 - 2f)\tilde{V}_d.$$

Under this assumption, $\rho_o$ is unchanged and, again R corrects to 1.

Figure 36A:
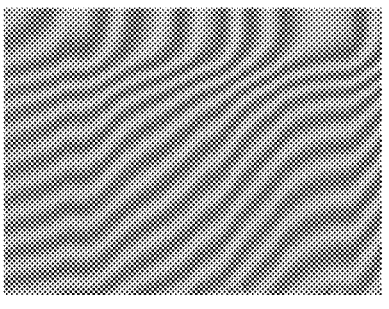
FIGS. 36A-36E are indirect moiré images obtained with cross-grid examples.
Figure 36B:
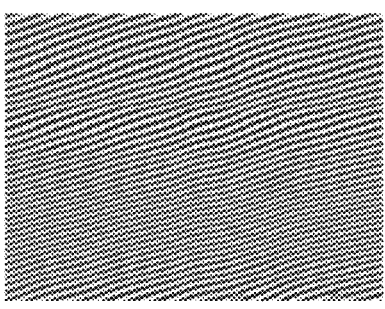
Figure 36C:
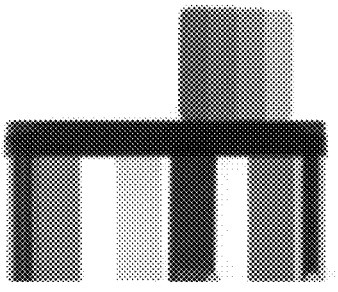
Figure 36D:
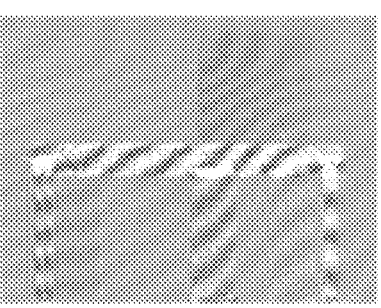
Figure 36E:
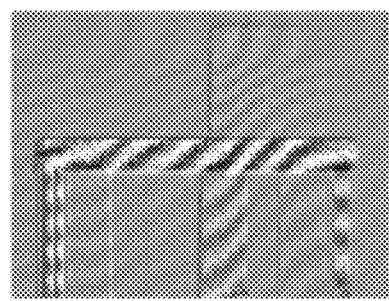

However, as discussed hereinabove, it has been found that the fringe artifacts that can occur in cross-moiré scanning can be reduced. As discussed previously, in cross-moiré scanning, a rectilinearly periodic perforated analyzer grating can be used to form moiré fringes together with both an object grating and a detector grating. By stepping the analyzer grating (or the detector and object gratings, or both) across one or more periods in both x and y Cartesian directions, the phase, contrast, and absorption can be measured for both detector and object gratings. However, when processing these data sets, artifacts appear in the final images that tend to follow the paths of the moiré fringes for the object grating or superimposed fringes of object and detector ratings. These artifacts can be seen more prominently in high attenuation regions. Examples of such artifacts obtained from cross-grid scanning can be seen in FIGS. 36A-36E. For example, FIG. 36A shows object grating moiré fringes, FIG. 36B shows detector grating moiré fringes, and FIGS. 36C-36E show absorption, visibility ratio, and phase images, respectively.

Figure 37:
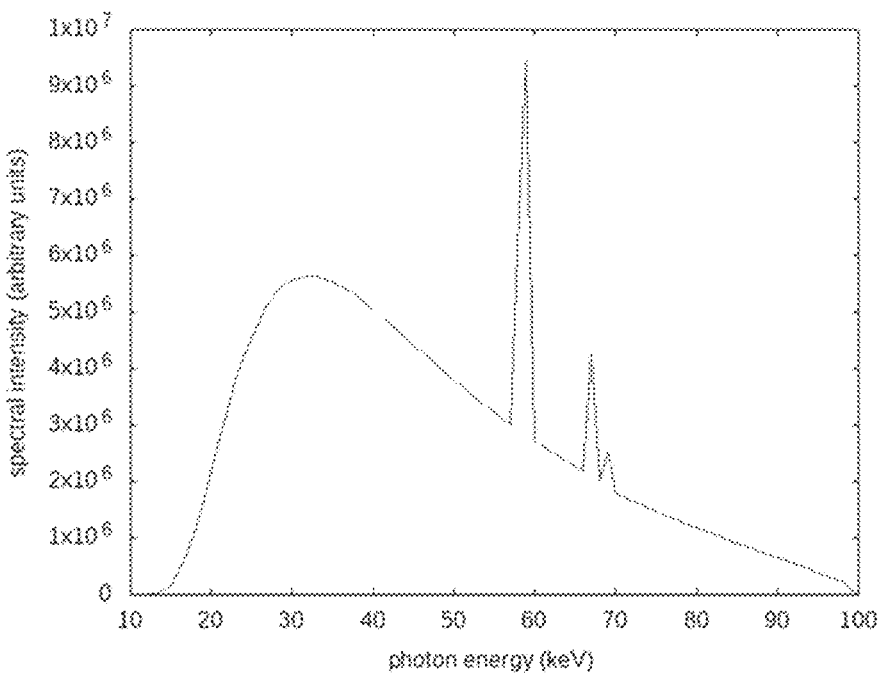
FIG. 37 is a graph of a spectrum of a x-ray beam after transmission through an aluminum filter.
Figure 38:
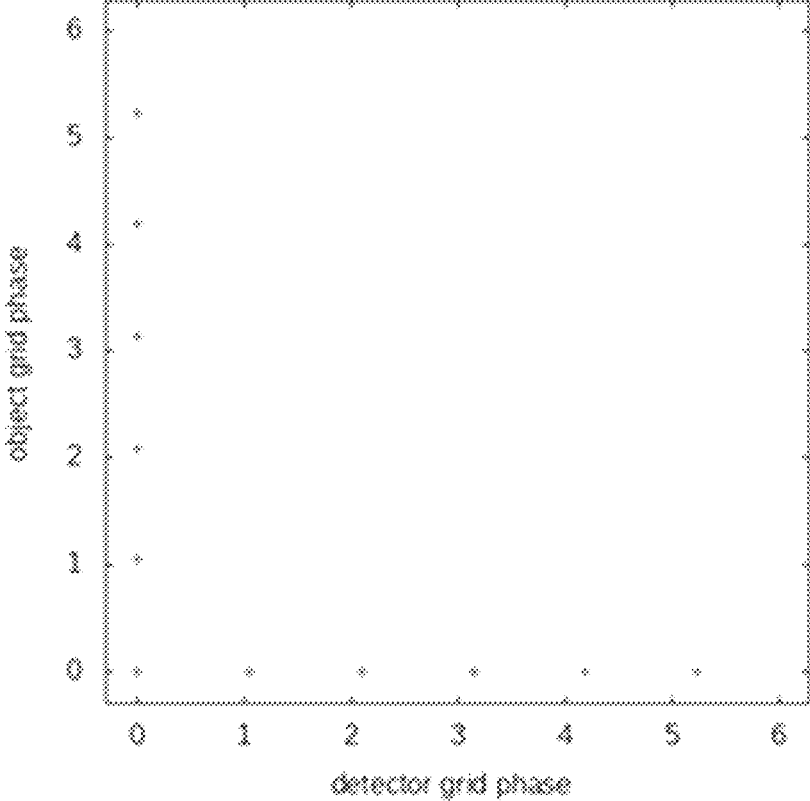
FIG. 38 is a graph of an example L-shaped set of phase position combinations for an object grating and a detector grating arranged along a beam path.

Cross grid fringe artifacts were investigated through simulation. A spectral calculator (SpekCalc) was used to generate a spectrum for an x-ray source based on a 100 kV end point energy, which is a typical x-ray source spectrum filtered by 2 mm Al. Such a spectrum is shown in FIG. 37. A grating thickness was specified for the object, detector, and analyzer gratings. The material used for the gratings was assumed to be lead. An aluminum slab with thickness chosen to reduce the x-ray intensity by a factor of $e^{-2}$ (two effective mean free paths for this spectrum) was chosen for the object, and positioned to occupy a right half of the detector. The attenuation coefficients for lead and aluminum were taken from the NIST (National Institute of Standards and Technology) x-ray attenuation database. The spectrum was propagated through every combination of gratings and object, and the integrated resulting spectrum was used for the detector signal behind that set of obstructing devices. For every pixel, an average was taken over the signals weighted by the fraction of the geometry occupied by the combination of obstructing devices in that pixel. This gives an x-ray image for the particular geometry chosen. The analyzer grating was then phase stepped with respect to the detector and object gratings (e.g., translated perpendicularly with respect to the beam path at selected increments) in order to obtain a sequence of phase step images that were processed using available software for extracting absorption, visibility ratio, and phase images from moiré scanning measurements. For the base simulation, the phase with respect to the object grating was held fixed at zero while the detector grating phase was stepped by $\pi/3$ for six phase steps; then the detector grating phase was held at zero while the object grating phase was stepped by $\pi/3$ for six phase steps. FIG. 38 shows a 2-D plot of the phase combinations used for the base phase scanning simulation. These phase steps can correspond to phase steps that are taken in current 2-D moiré scanning measurements.

Analysis methods for collected scanned moiré measurements are now discussed. Consider the intensity $I(x, y; \mu, \nu)$ at pixel $(x, y)$, with horizontal phase $\mu$ and the vertical phase $\nu$ of the analyzer grating with respect to the detector and object gratings, respectively. At this pixel, the x-rays must pass through a thickness of material $T(x, y; \mu, \nu)$. If $\tau$ is the attenuation length for x-rays in the material, then:

$$I(x, y; \mu, \nu) = I_0 \exp\left[-\frac{T(x, y; \mu, \nu)}{\tau}\right].$$

$T(x, y; \mu, \nu)$ is the sum of the thicknesses of the object grating $T_o(x, y; \nu)$ and detector grating $T_d(x, y; \mu)$. As the lowest order terms (zeroth and first) are of interest in the Fourier transform with respect to the phase, each of these can be decomposed into a mean value for the grid $\overline{T}(x, y)$ and an oscillatory term $\delta T_o(x, y) \cos[\nu + \phi_o(x, y)]$ or $\delta T_d(x, y) \cos[\mu + \phi_d(x, y)]$:

$$I(x, y; \mu, \nu) = I_0 \exp\left[-\frac{1}{\tau}\left(\overline{T}_d(x, y) + \right.\right.$$
$$\left.\left. \delta T_d(x, y) \cos[\mu + \phi_d(x, y)] + \overline{T}_o(x, y) + \delta T_o(x, y) \cos[\nu + \phi_o(x, y)]\right)\right]$$

The x-rays traverse a mean free path of:

$$\alpha(x, y; \mu, \nu) =$$
$$-\ln[I(x, y; \mu, \nu)] = \ln[I_0] - \frac{1}{\tau}\left(\overline{T}_d(x, y) + \delta T_d(x, y)\cos[\mu + \phi_d(x, y)] + \right.$$

-continued
$$\overline{T}_o(x, y) + \delta T_o(x, y)\cos[\nu + \phi_o(x, y)]\right) =$$
$$\overline{\alpha}(x, y) + V_d(x, y)\cos[\mu + \phi_d(x, y)] + V_o(x, y)\cos[\nu + \phi_o(x, y)]$$

The Fourier decomposition can then be performed on $\alpha(x, y; \mu, \nu)$. For the detector grating this returns the phase $\phi_d(x, y)$, amplitude $V_d(x, y)$, and mean $M_d(x, y) = \overline{\alpha}(x, y) + \delta\alpha_0(x, y) \cos[\langle\nu\rangle + \phi_o(x, y)]$. For the object grating, the phase $\phi_o(x, y)$, amplitude $V_o(x, y)$, and mean of $M_o(x, y) = \overline{\alpha}(x, y) + V_d(x, y) \cos[\langle\mu\rangle + \phi_d(x, y)]$ can be obtained. This provides sufficient information to solve directly for $\alpha(x, y)$. In fact, two separate solutions for $\alpha(x, y)$ are:

$$\overline{\alpha}_d(x, y) = (M_d(x, y) - V_o(x, y)\cos[\langle\nu\rangle + \phi_o(x, y)])$$

and $$\overline{\alpha}_o(x, y) = (M_o(x, y) - V_d(x, y)\cos[\langle\mu\rangle + \phi_d(x, y)]).$$

Thus, $\overline{\alpha}(x, y)$ can be estimated as the average of these two:

$$\overline{\alpha}(x, y) = \frac{1}{2}[(M_d(x, y) - V_o(x, y)\cos[\langle\nu\rangle + \phi_o(x, y)]) +$$
$$(M_o(x, y) - V_d(x, y)\cos[\langle\mu\rangle + \phi_d(x, y)])]$$

Now, with:

$$I(x, y; \mu, \nu) = \exp[-\alpha(x, y; \mu, \nu)] =$$
$$\exp[-\overline{\alpha}(x, y)]\exp[-V_d(x, y)\cos[\mu + \phi_d(x, y)]]\exp[-V_o(x, y)\cos[\nu + \phi_o(x, y)]]$$

and assuming the Vs are small:

$$\exp[-V_d(x, y)\cos[\mu + \phi_d(x, y)]] \approx 1 - V_d(x, y)\cos[\mu + \phi_d(x, y)]$$
$$\exp[-\delta\alpha_0(x, y)\cos[\nu + \phi_o(x, y)]] \approx 1 - V_o(x, y)\cos[\nu + \phi_o(x, y)]$$

the first order in $\delta\alpha$ can be found:

$$I(x, y; \mu, \nu) \approx$$
$$\exp[-\overline{\alpha}(x, y)](1 - V_d(x, y)\cos[\mu + \phi_d(x, y)] - V_o(x, y)\cos[\nu + \phi_o(x, y)]).$$

In other words, the Vs are the grid visibilities, and the phase shift function of the grid image will have an additional $\pi$ to cancel out that minus sign. This $\pi$ is removed when subtracting the flat field phase shift, and is unobservable.

There are several methods that can be used to correct out certain effects that may have occurred during data collection. A region of the phase step images that ideally does not have the analyzer grating in it can be integrated to obtain the relative exposure of each phase step, the phase steps can then all be normalized or otherwise corrected for variations in exposure.

In experimental arrangements, the actual phase of the analyzer grating with respect to the detector and object gratings can be measured to within approximately 0.01 radians (depending on noise, stage accuracy, and number of steps) by Fourier transforming the phase step images, selecting the pixel corresponding to the analyzer grid first harmonic—or, alternately, to the corresponding moiré fringe. The phase of this pixel gives the phase of the analyzer grating in that image. For example, if the translation stage has worse accuracy than about 0.0016 of a period (corresponding to 0.01 radians of phase), this can help to determine the actual phase value. However, it will be appreciated that other measurement accuracies are possible in various systems and arrangements.

To correct for differences between the measured phase and assumed phase, for each pixel (x, y) the values $\overline{\alpha}(x, y)$, $V_d(x, y)$, $V_o(x, y)$, $\phi_d(x, y)$, and $\phi_o(x, y)$ can be found using the assumed phase of two step sequences, where each sequence has one grid with which it remains at zero phase and is stepped in N equal intervals with respect to the other grid, giving the analysis from the beginning of this section. This produces 2N data points $I_m(x, y; \mu, v)$ at known $(\mu, v)$. The correction for the known $(\mu, v)$ can be performed by minimizing:

$$\chi^2 = \sum_{m=1}^{2N} (I_m(x, y; \mu, v) - I(x, y; \mu, v))^2.$$

by varying $\overline{\alpha}(x, y)$, $V_d(x, y)$, $V_o(x, y)$, $\phi_d(x, y)$, and $\phi_o(x, y)$ with a Levenberg-Marquardt algorithm.

Figure 39A:
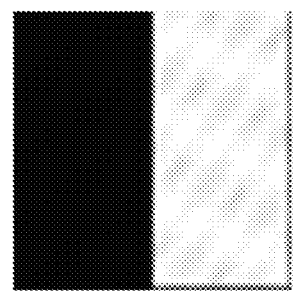
FIGS. 39A-39C are images of absorption coefficient, visibility ratio, and phase shift produced from simulated data for the broad spectrum source shown in FIG. 37.
Figure 39B:
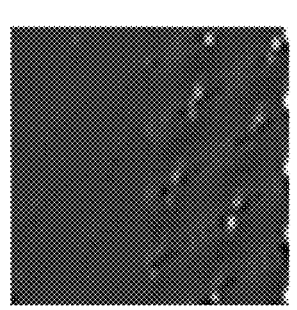
Figure 39C:
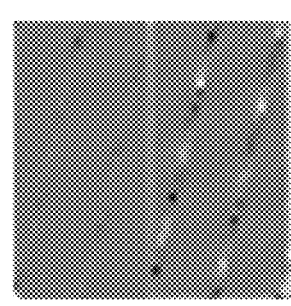
Figure 40A:
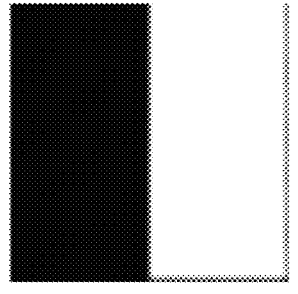
FIGS. 40A-40C are images of absorption coefficient, visibility ratio, and phase shift produced from simulated data for a monochromatic (narrow) spectrum source.
Figure 40B:
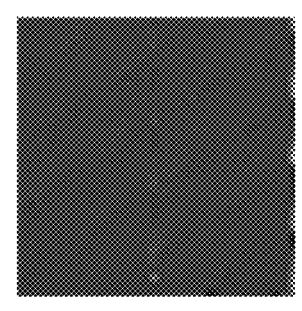
Figure 40C:
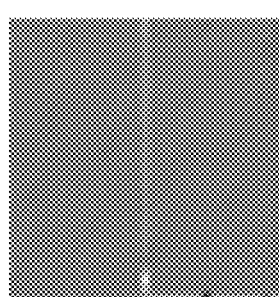

A standard analysis was performed on the simulated data and the results are shown in FIGS. 39A-39C, which correspond to images of absorption coefficient, visibility ratio, and phase shift, respectively. Clear moiré fringe artifacts can be seen, indicating that the simulation method captures a physics that can reproduce these artifacts. The simulation was repeated with a monochromatic 50 keV spectrum and the corresponding results are shown in FIG. 40A-40C. The results correspond to images of absorption coefficient, visibility ratio, and phase shift, respectively. The fringe artifacts are significantly reduced with a monochromatic spectrum, indicating that the main source of the artifacts is spectral. The presence of less prominent fringe artifacts remaining in the monochromatic simulation results suggests there are also other, non-spectral contributions of lesser importance.

Figure 41A:
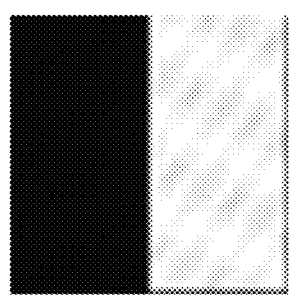
FIGS. 41A-41C are images of absorption coefficient, visibility ratio, and phase shift for a set of phase positions.
Figure 41B:
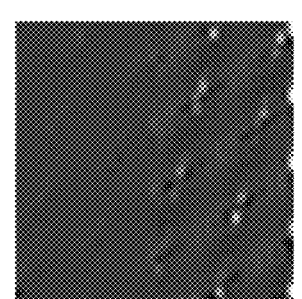
Figure 41C:
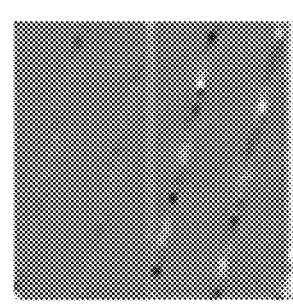
Figure 42A:
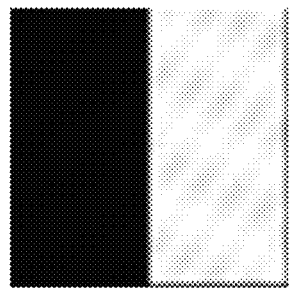
FIGS. 42A-42C are images of absorption coefficient, visibility ratio, and phase shift after averaging zero phase shift and π-shift analyses.
Figure 42B:
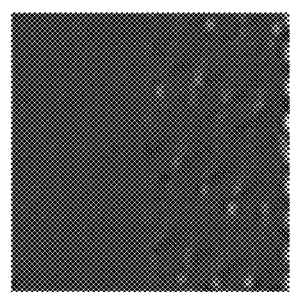
Figure 42C:
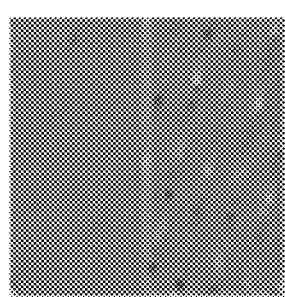

Various techniques can be employed to reduce artifacts due to spectral averaging. If a set of two orthogonal phase scans produces artifacts corresponding to the moiré fringes, then it can follow that shifting the phase of the static grid during the scan by π radians will produce artifacts with the opposite sense of the fringe artifacts—e.g., regions that were once darker become brighter, and vice versa. Taking the average of the standard and π-shifted images can help to average out the artifacts. FIGS. 41A-42C illustrate the effect of an averaging of the zero phase shift analysis with the π-shifted analysis. More specifically, FIGS. 41A-41C show the uncorrected base analysis of images of absorption coefficient, visibility ratio, and phase shift, respectively. FIGS. 42A-42C show the corrected base analysis of images of absorption coefficient, visibility ratio, and phase shift, respectively. Thus, as can be seen by comparing the uncorrected and corrected images, in practice, the artifacts are reduced but the improvement is often not complete or not necessarily substantial.

Another way to correct the artifacts due to spectral averaging is to acquire additional data in additional parts of the phase plane to fill in information missing from the two phase step measurement sets with fixed zero phase of the stationary grid that are shown in FIG. 38. These additional measurements are included directly as data into the $\chi^2$ minimization step in addition to the original sets of orthogonal steps used for the initial parameter estimates. In many examples, the additional measurements are not used for the initial parameter estimates and instead only for the final minimization step. As such, they can have arbitrary phase coordinates within the [0: 2π] range.

Figure 43:
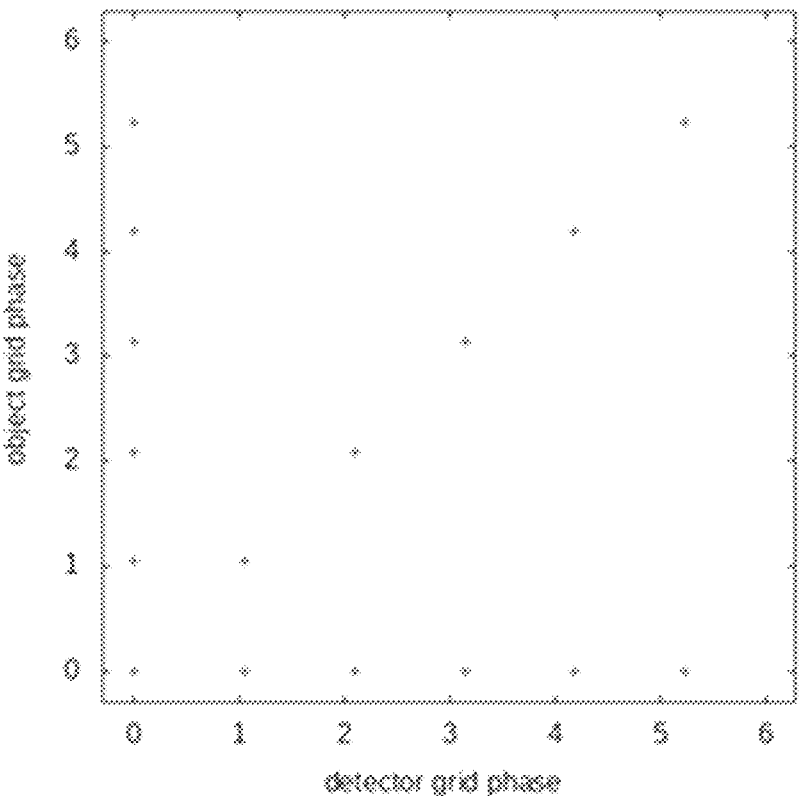
FIG. 43 is a graph of a set of phase positions including an L-shaped set and a diagonal set.
Figure 44:
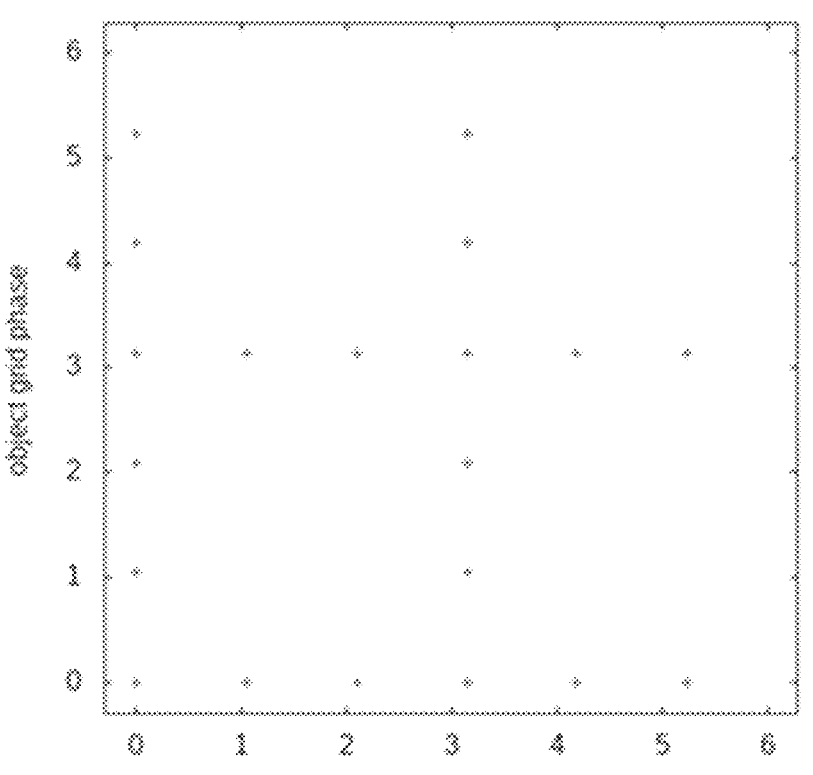
FIG. 44 is a graph of a set of phase positions including an L-shaped set and a cross-shaped π-shifted set.
Figure 45:
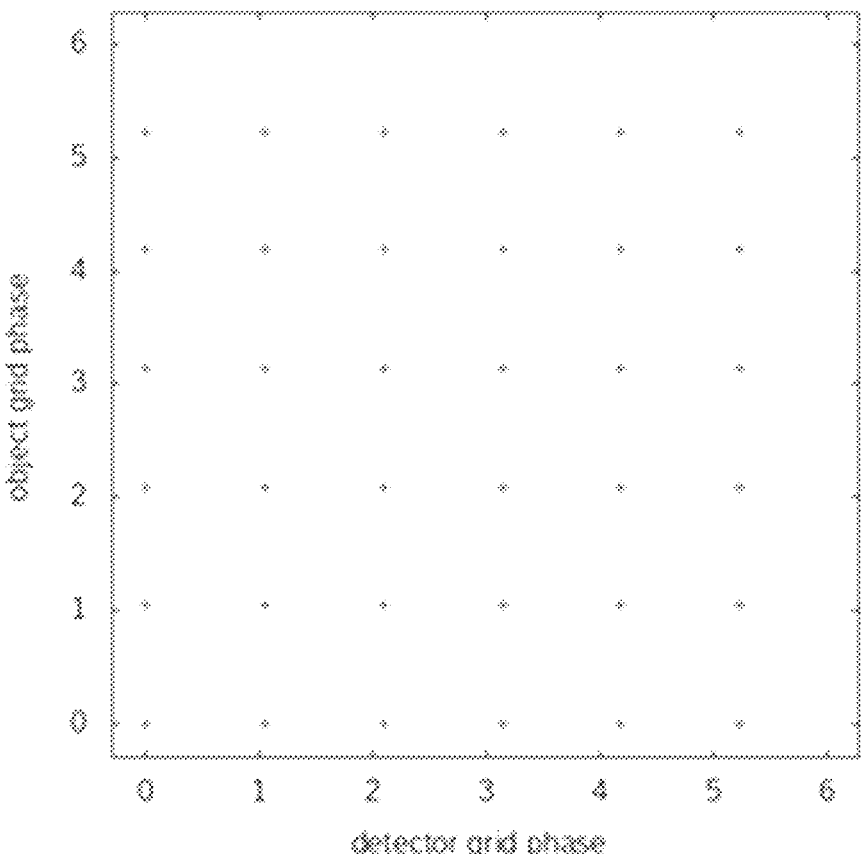
FIG. 45 is a graph of a latticed set of phase positions.
Figures 46A, 46B, 46C, 46D:
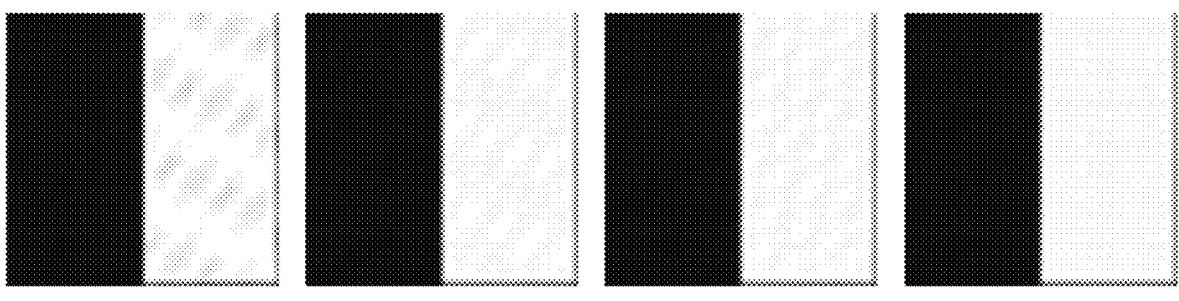
FIGS. 46A-46D are absorption coefficient images for different sets of phase positions corresponding to base phase steps, base+diagonal phase steps, base+pi-shift phase steps, and a latticed sequence, respectively.
Figures 47A, 47B, 47C, 47D:
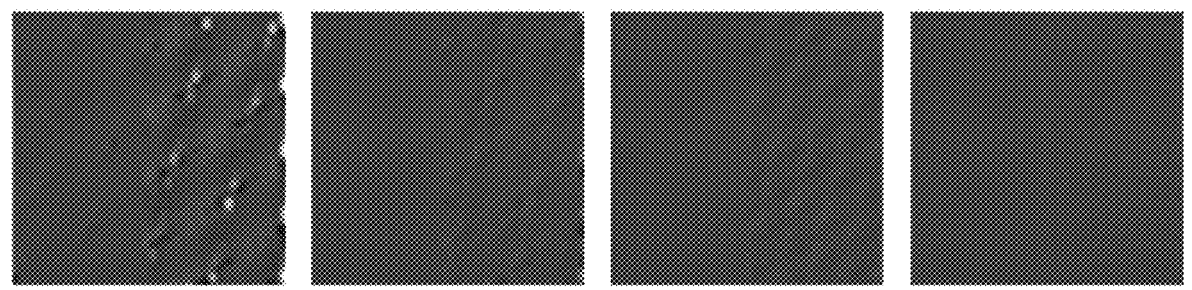
FIGS. 47A-47D are visibility images for the same sets of phase positions used in FIGS. 46A-46D.
Figures 48A, 48B, 48C, 48D:
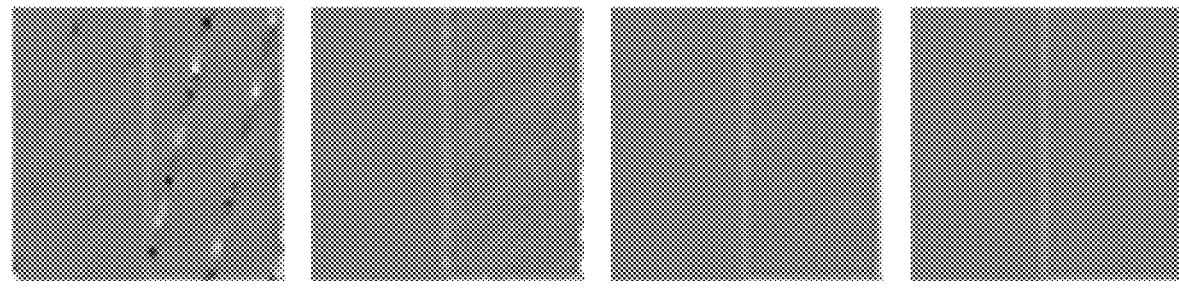
FIGS. 48A-48D are phase shift images for the same sets of phase positions used in FIGS. 46A-46D.

Three sequences of phase step measurements that provided additional phase information were selected and examined, though it will be appreciated that other sequences may be used. FIG. 43 shows an example of a "diagonal" phase scanning sequence, i.e., in addition to the original orthogonal sets (e.g., forming an "L" shape) an additional set of measurements is taken where the analyzer grid has the same phase with respect to both detector and object gratings. FIG. 44 shows an example of a π-shift phase scanning sequence in which two additional sets are taken with the analyzer grid set to π radians of phase relative to one stationary grid while stepping relative to the other, and vice versa, which can efficiently average over spectral effects. FIG. 45 shows an example of a lattice phase scanning sequence, where a phase measurement is taken for every combination m, n∈{0, 1, 2, 3, 4, 5} with phase (2πm/6, 2πn/6).

Image results from adding the additional phase step sets into the final fit are shown in FIG. 46A-48D. In particular, FIGS. 46A-46D show images for the absorption coefficient for base phase steps, base+diagonal phase steps, base+pi-shift phase steps, and a latticed sequence, respectively. FIGS. 47A-47D show images for the visibility for base phase steps, base+diagonal phase steps, base+pi-shift phase steps, and a latticed sequence, respectively. FIGS. 48A-48D show images for the phase shift for base phase steps, base+diagonal phase steps, base+pi-shift phase steps, and a latticed sequence, respectively. It can be seen from the image results that adding additional phase step sets can significantly reduce the artifacts. Also, the magnitude of the residual artifacts reduces with increasing numbers of data sets to fill in the unsampled region of the phase plane.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A system, comprising:
an x-ray source configured to emit an x-ray beam along a beam path and through an object arranged for inspection in a field of view of the x-ray source; and
an object grating, an analyzer grating, a detector grating, and a detector arranged with respect to each other in the field of view;
wherein the object grating includes object grating elements arranged in a first pattern, the detector grating includes detector grating elements arranged in a second pattern that is separable from the first pattern, and the analyzer grating includes analyzer grating elements that are arranged to correspond to a combination of the first pattern and second pattern;
wherein the analyzer grating, and/or the object grating and detector grating, are configured to move relative to each other to different phase positions, and wherein the detector is configured to collect indirect moiré image data of the object at the different phase positions.

2. The system of claim 1, wherein the analyzer grating, and/or the object grating and detector grating, are configured to move relative to each other to the different phase positions by translating the analyzer grating transverse to the beam path to the different phase positions while the detector grating and object grating are fixed.

3. The system of claim 1, wherein the object grating and detector grating are configured to move relative to the analyzer grating to the different phase positions by translating the object grating and detector grating transverse to the beam path to the different phase positions while the analyzer grating is fixed.

4. The system of claim 1, wherein the object grating elements include a set of parallel linear object grating elements, the detector grating elements include a set of parallel linear detector grating elements arranged perpendicularly with respect to the parallel linear object grating elements, and the analyzer grating elements include a set of crossed grating elements.

5. The system of claim 1, further comprising one or more movement stages coupled to the analyzer grating and/or the object grating and detector grating to provide the relative movement to the different phase positions.

6. The system of claim 1, wherein the relative movement to different phase positions includes a first set of positions along a first axis aligned with a direction of the first pattern and a second set of positions along a second axis aligned with a direction of the second pattern.

7. The system of claim 6, wherein the relative movement to different phase positions further includes a set of one or more additional off-axis positions configured to average spectral information associated with the object grating and detector grating and thereby reduce moiré artifacts associated with the moiré image data.

8. The system of claim 6, wherein the relative movement to different phase positions further includes a set of positions to define a latticed array of positions.

9. The system of claim 6, wherein the relative movement to the different phase positions includes a third set of positions aligned with the direction of the first pattern and spaced apart from the first set of positions, and a fourth set of positions aligned with the direction of the second pattern and spaced apart from the second set of positions.

10. The system of claim 9, wherein the third set of positions is spaced apart from the first set of positions by a pi-shift and the fourth set of positions is spaced apart from the second set of positions by a pi-shift.

11. The system of claim 1, further comprising a processor and memory configured with processor executable instructions which cause the processor to apply a beam hardening correction to the indirect moiré image data.

12. The system of claim 1, further comprising a source grating situated adjacent to the x-ray source and configured to receive the x-rays from the x-ray source to produce a plurality of source grating x-ray sources.

13. The system of claim 1, wherein the object grating, analyzer grating, and detector gratings are arranged in the field of view along the beam path such that the analyzer grating precedes the detector, the detector grating precedes the analyzer grating, and the position of the object to be inspected precedes the analyzer grating.

14. The system of claim 13, wherein the object grating precedes the position of the object to be inspected.

15. A method, comprising:
emitting an x-ray beam from an x-ray source along a beam path and through a position for an object arranged to be inspected in a field of view of the x-ray source, wherein an object grating, an analyzer grating, a detector grating, and a detector are arranged with respect to each other in the field of view, wherein the object grating includes object grating elements arranged in a first pattern, the detector grating includes detector grating elements arranged in a second pattern that is separable from the first pattern, and the analyzer grating includes analyzer grating elements that are arranged to correspond to a combination of the first pattern and second pattern;
moving the analyzer grating, and/or the object grating and detector grating, relative to each other to different phase positions; and
detecting indirect moiré image data with the detector at the different phase positions.

16. The method of claim 15, wherein the moving comprises translating the analyzer grating transverse to the beam path to the different phase positions while the detector grating and object grating are fixed.

17. The method of claim 15, wherein the moving comprises translating the object grating and detector grating transverse to the beam path to the different phase positions while the analyzer grating is fixed.

18. The method of claim 15, wherein the object grating elements include a set of parallel linear object grating elements, the detector grating elements include a set of parallel linear detector grating elements arranged perpendicularly with respect to the parallel linear object grating elements, and the analyzer grating elements include a set of crossed grating elements.

19. The method of claim 15, wherein the moving comprises moving the analyzer grating, and/or the object grating and detector grating, relative to each other to the different phase positions with one or more movement stages.

20. The method of claim 19, wherein the moving to the different phase positions further includes moving to a set of one or more additional off-axis positions configured to average spectral information associated with the object grating and detector grating and thereby reduce moiré artifacts associated with the moiré image data.

21. The method of claim 20, wherein the moving to the one or more additional off-axis positions includes moving to a set of positions such that the different phase positions comprise a crossed or L-shaped set of positions and a diagonal set of positions.

22. The method of claim 20, wherein the moving to the one or more additional off-axis positions includes moving to a set of positions such that the different phase positions comprise a latticed array of positions.

23. The method of claim 15, wherein the moving to the different phase positions comprises moving to a first set of positions along a first axis aligned with a direction of the first pattern and moving to a second set of positions along a second axis aligned with a direction of the second pattern.

24. The method of claim 23, wherein the moving to the different phase positions further comprises moving to a third set of positions aligned with the direction of the first pattern and spaced apart from the first set of positions, and to a fourth set of positions aligned with the direction of the second pattern and spaced apart from the second set of positions.

25. The method of claim 24, wherein the third set of positions is spaced apart from the first set of positions by a pi-shift and the fourth set of positions is spaced apart from the second set of positions by a pi-shift.

26. The method of claim 15, further comprising, with a processor and memory configured with processor executable instructions, applying a beam hardening correction to the indirect moiré image data.

27. The method of claim 15, wherein the object grating, analyzer grating, and detector gratings are arranged in the field of view along the beam path such that the analyzer grating precedes the detector, the detector grating precedes the analyzer grating, and the position of the object to be inspected precedes the analyzer grating.

28. The method of claim 27, wherein the object grating precedes the position of the object to be inspected.

29. A non-transitory computer readable storage medium storing one or more programs, the one or more programs comprising instructions, which when executed by one or more processors operably connected to an x-ray imaging system that comprises:

an x-ray source configured to emit an x-ray beam along a beam path and through an object arranged for inspection in a field of view of the x-ray source; and an object grating, an analyzer grating, a detector grating, and a detector arranged with respect to each other in the field of view;

wherein the object grating includes object grating elements arranged in a first pattern, the detector grating includes detector grating elements arranged in a second pattern that is separable from the first pattern, and the analyzer grating includes analyzer grating elements that are arranged to correspond to a combination of the first pattern and second pattern; wherein the analyzer grating, and/or the object grating and detector grating, are configured to move relative to each other to different phase positions, and wherein the detector is configured to collect indirect moiré image data of the object at the different phase positions;

causes the x-ray imaging system to collect the indirect moiré image data at the different phase positions.

\* \* \* \* \*